(12) United States Patent
O'Hehir et al.

(10) Patent No.: US 11,266,737 B2
(45) Date of Patent: Mar. 8, 2022

(54) IMMUNOTHERAPEUTIC COMPOSITION AND USES THEREOF

(71) Applicant: ARAVAX PTY LTD, Victoria (AU)

(72) Inventors: Robyn Elizabeth O'Hehir, Victoria (AU); Sara Rachel Prickett, Victoria (AU); Jennifer May Rolland, Victoria (AU)

(73) Assignee: ARAVAX PTY LTD, Melbourne (AU)

( * ) Notice: Subject to any disclaimer, the term of this patent is extended or adjusted under 35 U.S.C. 154(b) by 767 days.

(21) Appl. No.: 15/024,666

(22) PCT Filed: Sep. 25, 2014

(86) PCT No.: PCT/AU2014/050249
§ 371 (c)(1),
(2) Date: Mar. 24, 2016

(87) PCT Pub. No.: WO2015/042664
PCT Pub. Date: Apr. 2, 2015

(65) Prior Publication Data
US 2016/0375130 A1   Dec. 29, 2016

(30) Foreign Application Priority Data
Sep. 25, 2013 (AU) ............... 2013903686

(51) Int. Cl.
| A61K 39/35 | (2006.01) |
| A61K 39/00 | (2006.01) |
| A61P 37/08 | (2006.01) |
| A61K 38/08 | (2019.01) |
| A61K 38/10 | (2006.01) |
| A61P 37/00 | (2006.01) |
| A61K 31/7088 | (2006.01) |

(52) U.S. Cl.
CPC .......... *A61K 39/35* (2013.01); *A61K 31/7088* (2013.01); *A61K 38/08* (2013.01); *A61K 38/10* (2013.01); *A61P 37/00* (2018.01); *A61P 37/08* (2018.01); *A61K 2039/54* (2013.01); *A61K 2039/577* (2013.01)

(58) Field of Classification Search
None
See application file for complete search history.

(56) References Cited

U.S. PATENT DOCUMENTS

| 5,558,869 | A | 9/1996 | Burks, Jr. et al. |
| 5,973,121 | A | 10/1999 | Burks, Jr. et al. |
| 6,835,824 | B1 | 12/2004 | Burks, Jr. et al. |
| 7,179,645 | B2 | 2/2007 | Humphreys et al. |
| 7,923,209 | B2 * | 4/2011 | Spertini ............ A61K 39/35 435/7.1 |
| 8,815,249 | B2 | 8/2014 | Humphreys et al. |
| 9,289,487 | B2 | 3/2016 | Humphreys et al. |
| 2002/0147140 | A1 | 10/2002 | Rosen et al. |
| 2003/0202980 | A1 | 10/2003 | Caplan et al. |
| 2003/0235594 | A1 | 12/2003 | Humphreys et al. |
| 2004/0058881 | A1 | 3/2004 | Humphreys et al. |
| 2006/0002947 | A1 | 1/2006 | Humphreys et al. |
| 2006/0292138 | A1 | 12/2006 | Chen |
| 2008/0305122 | A1 | 12/2008 | Humphreys et al. |
| 2010/0291145 | A1 | 11/2010 | Humphreys et al. |
| 2012/0178139 | A1 | 7/2012 | Hubbell et al. |
| 2015/0328294 | A1 | 11/2015 | O'Hehir et al. |

FOREIGN PATENT DOCUMENTS

| EA | 019923 B1 | 7/2014 |
| EP | 2153841 A1 | 2/2010 |
| GB | 2455108 A | 6/2009 |
| JP | 2002509117 A | 3/2002 |
| JP | 2006515744 A | 6/2006 |
| RU | 2285042 C2 | 10/2006 |
| RU | 2429881 C2 | 9/2011 |
| WO | WO-9724139 A1 | 7/1997 |
| WO | 1999/036090 A1 | 7/1999 |
| WO | WO-9934826 A1 | 7/1999 |
| WO | WO-9938978 A1 | 8/1999 |

(Continued)

OTHER PUBLICATIONS

Koppelman et al. 'Relevance of Ara h1, Ara h2 and Ara h3 in peanut-allergic patients, asdetermined by immunoglobulin E Western blotting, basophil-histamine releaseand intracutaneous testing: Ara h2 is the most important peanut allergen.' Clin. Exp. Allergy 34: 583-590, 2004.*
Chruszcz et al. 'Structural and Immunologic Characterization of Ara h 1, a Major Peanut Allergen.' The Journal of Biological Chemistry vol. 286, No. 45, pp. 39318-39327, 2011.*
Burks et al. 'Mapping and mutational analysis of the IgE-binding epitopes on Ara h 1, a legume vicilin protein and a major allergen in peanut hypersensitivity.' Eur. J. Biochem 245:334-339, 1997.*
Cong et al. 'Characterisation of the IgE-binding immunodominant epitopes on Ara h1.' Food Agric. Immunol. 19:175-185, 2008.*
Kinnunen et al. 'Potential of an altered peptide ligand of lipocalin allergen Bos d 2 for peptide immunotherapy.' J. Allerg. Clin. Immunol. 119:965-72, 2007.*
Schein et al. 'Bioinformatics approaches to classifying allergens and predicting cross-reactivity.' Immunol. Allergy Clin. North Am. 27 (1):1-27, 2007.*

(Continued)

*Primary Examiner* — Nora M Rooney
(74) *Attorney, Agent, or Firm* — Mintz Levin Cohn Ferris Glovsky and Popeo, P.C.; Ingrid A. Beattie

(57) ABSTRACT

The present invention relates generally to an immunotherapeutic composition. More particularly, the present invention relates to an immunotherapeutic composition which interacts immunologically with T lymphocytes in subjects having peanut allergy or allergy to other tree nuts. This composition is preferably immunointeractive with T cells in subjects having an allergy to the Ara h 1 and/or Ara h 2 allergens. The composition of the present invention is useful in the therapeutic or prophylactic treatment of conditions characterised by an aberrant, inappropriate or otherwise unwanted immune response to peanut, Ara h 1 and/or Ara h 2 or derivative or homologue thereof.

7 Claims, 35 Drawing Sheets
(6 of 35 Drawing Sheet(s) Filed in Color)
Specification includes a Sequence Listing.

(56) References Cited

FOREIGN PATENT DOCUMENTS

| WO | WO-9945961 A1 | 9/1999 |
|---|---|---|
| WO | WO-0051647 A2 | 9/2000 |
| WO | WO-0052154 A2 | 9/2000 |
| WO | WO-0054803 A2 | 9/2000 |
| WO | WO-0139799 A2 | 6/2001 |
| WO | WO-0140264 A2 | 6/2001 |
| WO | 02040676 A2 | 5/2002 |
| WO | 02074250 A2 | 9/2002 |
| WO | WO-0274250 A2 | 9/2002 |
| WO | WO-02088317 A2 | 11/2002 |
| WO | WO-02088367 A1 | 11/2002 |
| WO | WO-03047618 A2 | 6/2003 |
| WO | 2004/081028 A2 | 9/2004 |
| WO | WO-2005121166 A1 | 12/2005 |
| WO | WO-2008145998 A1 | 12/2008 |
| WO | WO-2008146003 A1 | 12/2008 |
| WO | WO-2009022154 A2 | 2/2009 |
| WO | WO-2009022155 A2 | 2/2009 |
| WO | WO-2009022156 A2 | 2/2009 |
| WO | WO-2009022157 A2 | 2/2009 |
| WO | WO-2010000873 A1 | 1/2010 |
| WO | WO-2010018378 A2 | 2/2010 |
| WO | WO-2010018384 A1 | 2/2010 |
| WO | WO-2011032097 A1 | 3/2011 |
| WO | WO-2011106645 A1 | 9/2011 |

OTHER PUBLICATIONS

Friedl-Hajek et al. 'Identification of a highly promiscuous and an HLA allele-specific T-cell epitope in the birch major allergen Bet v 1 :HLA restriction, epitope mapping and TCR sequence comparisons.' Clin. Exp. Allergy 29:478-487, 1999.*
Rolland et al. 'Chapter 12 Peanut Allergy Biomolecular Characterization for Development of a Peanut T-Cell Epitope Peptide Therapy.' Food Allergy Molecular and Clinical Practice. Ed. Andreas Lopata CRC Press 2017.*
Otsu et al. 'Epitope analysis of Ara h 2 and Ara h 6: characteristic patterns of IgE-binding fingerprints among individuals with similar clinical histories.' Clin Exp Allergy. Feb. 2015 ; 45(2): 471-484. doi:10.1111/cea.12407.*
Prickett, S.R., et al., "Ara h 2 peptides containing dominant CD4+ T-cell epitopes: Candidates for a peanut allergy therapeutic", *Journal of Allergy and Clinical Immunology*, Mar. 2011, vol. 127, No. 3, pp. 608-615.e5, Whole document.
Prickett, S.R., et al., "Ara h 1 CD4+ T cell epitope-based peptides: candidates for a peanut allergy therapeutic", *Clinical & Experimental Allergy*, Jun. 2013, vol. 43, Issue 6, pp. 684-697, Whole document; Right column, p. 694.
Srivastava, K. D., "Immunotherapy With Modified Peanut Allergens in a Murine Model of Peanut Allergy", *Journal of Allergy and Clinical Immunology*, Jan. 2002, vol. 109, Issue 1, Supplement 1, p. S287, Abstract 877, Whole document.
DeLong et al., Ara h 1-reactive T cells in individuals with peanut allergy. J Allergy Clin Immunol. May 2011;127(5):1211-8.
Glaspole et al., Characterization of the T-cell epitopes of a major peanut allergen, Ara h 2. Allergy. Jan. 2005;60(1):35-40.
King et al., Allergenic characteristics of a modified peanut allergen. Mol Nutr Food Res. Oct. 2005;49(10):963-71.
Pascal et al., In silico prediction of Ara h 2 T cell epitopes in peanut-allergic children. Clin Exp Allergy. Jan. 2013;43(1):116-27.
Akdis, et al., "Mechanisms of Allergen-Specific Immunotherapy", Allergy, vol. 55, 2000, pp. 522-530.
Burks, et al., "Mapping and Mutational Analysis of the IgE-Binding Epitopes on Ara h 1, a Legume Vicilin Protein and a Major Allergen in Peanut Hypersensitivity", European Journal of Biochemistry, vol. 245, Jan. 9, 1997, pp. 334-339.
De Long, et al., "Ara h 1-Reactive T Cells in Individuals with Peanut Allergy", Journal of Allergy and Clinical Immunology, vol. 127, No. 5, May 2011, pp. 1211-1218.

O'Hehir, et al., "House Dust Mite Sublingual Immunotherapy: The Role for Transforming Growth Factor-Beta and Functional Regulatory T Cells", American Journal of Respiratory and Critical Care Medicine, Nov. 15, 2009, 180(10):936-947.
O'Hehir, et al., "T Cell Epitope Peptide Therapy for Allergic Diseases", Current Allergy and Asthma Reports: Current Science, Jan. 14, 2016, 16(2):1-9.
Pene, et al., "Immunotherapy with Fel d 1 Peptides Decreases IL-4 Release by Peripheral Blood T Cells of Patients Allergic to Cats", Journal of Allergy and Clinical Immunology, Oct. 1998, 102(4):571-578.
Prickett, et al., "Oral Abstract Session 5: Abstract 25", Allergy, 2012, 67 (Suppl 96), 1-97, p. 12.
Pumphrey, Richard, "Anaphylaxis: Can We Tell Who is at Risk of a Fatal Reaction?", Current Opinion in Allergy & Clinical Immunology, 2004, 4(4):285-290.
Van De Veen, et al., "Oral Abstract Session 6: Abstract 25", Allergy, 2012, 67 (Suppl 96), 1-97, p. 12.
Van Neerven, et al., "Characterization of Cat Dander-Specific T Lymphocytes from Atopic Patients", Journal of Immunology, vol. 152, No. 8, Apr. 15, 1994, pp. 4203-4210.
Prickett, et al., "Immunoregulatory T Cell Epitope Peptides: The New Frontier in Allergy Therapy", Clinical & Experimental Allergy, vol. 45, 2015, 1015-1026.
Knapp, et al., "pSEM Vectors: High Level Expression of Antigenic Determinants and Protein Domains", BioTechniques, Mar. 1990, 8(3):280-281.
Bernard et al. (May 2015), "Allergenicity of Peanut Component Ara h 2: Contribution of Conformational Versus Linear Hydroxyproline-containing Epitopes", The Journal of Allergy and Clinical Immunology, 35(5):1267-1274.
Van Hoeyveld et al. (Sep. 1998), "Allergenic and Antigenic Activity of Peptide Fragments in a Whey Hydrolysate Formula", Clinical & Experimental Allergy, 28(9):1131-1137.
Geunwoong et al. "Oral Sessions", Jan. 1, 2012 (Jan. 1, 2012), XP055600181, Retrieved from the Internet: URL: https://onlinelibrary.wiley.com/doi/pdf/10.1111/all.12033 [retrieved on Jun. 27, 2019].
GenBank, U.S., 1996, L34402, URL, http://www.ncbi.nlm.nih.gov/nuccore/L34402.
Akdis, et al., "Bypassing IgE and Targeting T Cells for Specific Immunotherapy of Allergy", Trends in Immunology, vol. 22, No. 4, May 2001, pp. 175-178, Abstract only.
Akdis, et al., "Mechanisms and Treatment of Allergic Disease in the Big Picture of Regulatory T Cells", Journal of Allergy and Clinical Immunology, Apr. 2009, 123(4):735-746.
Akdis, et al., "Mechanisms of Allergen-Specific Immunotherapy", Journal of Allergy and Clinical Immunology, Jan. 2011, 127(1):18-27, Abstract only.
Akdis, et al., "Mechanisms of Allergen-Sepcific Immunotherapy", Allergy, vol. 55, 2000, pp. 522-530.
Akdis, et al., "Therapeutic Manipulation of Immune Tolerance in Allergic Disease", Nature Reviews Drug Discovery, Aug. 2009, 8(8):645-660, Abstract only.
Allergen Nomenclature, International Union of Immunological Societies (IUIS) Allergen Nomenclature Sub-committee. Available at: http://www.allergen.org/Allergen.aspx. Accessed Apr. 22, 2012, 12 pages.
Alexander, et al., "Fel d 1-Derived T Cell Peptide Therapy Induces Recruitment of CD4+ CD25+; CD4+ Interferon-Gamma+ T Helper Type 1 Cells to Sites of Allergen-Induced Late-Phase Skin Reactions in Cat-Allergic Subjects", Clinical & Experimental Allergy, Jan. 2005, 35(1):52-58, Abstract only.
Alexander, et al., "The Effect of Fel d 1-Derived T-Cell Peptides on Upper and Lower Airway Outcome Measurements in Cat-Allergic Subjects", Allergy, Oct. 2005, 60(10):1269-1274, Abstract only.
Amann, et al., "Tightly Regulated Tac Promoter Vectors Useful for the Expression of Unfused and Fused Proteins in *Escherichia coli*", Gene, Sep. 30, 1988, 69(2):301-315.
Anagnostou, et al., "Efficacy and Safety of High-Dose Peanut Oral Immunotherapy with Factors Predicting Outcome", Clinical & Experimental Allergy, Sep. 2011, 41(9):1273-1281, Abstract only.

(56) References Cited

OTHER PUBLICATIONS

Apostolou, et al., "Anaphylaxis to Gelofusine® Confirmed by in Vitro Basophil Activation Test: A Case Series", Anaesthesia, Apr. 2006, 61(3):264-268, Abstract only.
Asarnoj, et al., "IgE to Peanut Allergen Components: Relation to Peanut Symptoms and Pollen Sensitization in 8-Year-Olds", Allergy, Sep. 2010, 65(9):1189-1195, Abstract only.
Attwood, Teresa K., "The Babel of Bioinformatics", Science, vol. 290, No. 5491, Oct. 27, 2000, pp. 471-473.
Avery, et al., "Assessment of Quality of Life in Children with Peanut Allergy", Pediatric Allergy and Immunology, vol. 14, Issue 5, Oct. 2003, pp. 378-382, Abstract only.
Baldari, et al., "A Novel Leader Peptide which Allows Efficient Secretion of a Fragment of Human Interleukin 1 beta in *Saccharomyces cerevisiae*", The EMBO Journal, Jan. 1987, 6(1):229-234.
Baldari, et al., "A Novel Leader Peptide which Allows Efficient Secretion of a Fragment of Human Interleukin 13 in *Saccharomyces cerevisiae*", The EMBO Journal, 1987, 6(1):229-234.
Bateman, et al., "Identification of an Immunodominant Region of Fel d 1 and Characterization of Constituent Epitopes", Clinical & Experimental Allergy, vol. 38, Issue 11, Nov. 2008, pp. 1760-1768, Abstract only.
Blanc, et al., "Capacity of Purified Peanut Allergens to Induce Degranulation in a Functional in Vitro Assay: Ara h 2 and Ara h 6 are the Most Efficient Elicitors", Clinical & Experimental Allergy, Aug. 2009, 39(8):1277-1285, Abstract only.
Blumchen, et al., "Oral Peanut Immunotherapy in Children with Peanut Anaphylaxis", Journal of Allergy and Clinical Immunology, Jul. 2010, 126(1):83-91, Abstract only.
Blumenthal, et al., "Definition of an Allergen", Allergens and Allergen Immunotherapy, Marcel Dekker, vol. 3, 2004, 6 pages.
Bock, et al., "Further Fatalities Caused by Anaphylactic Reactions to Food, 2001-2006", Journal of Allergy and Clinical Immunology, Apr. 2007, 119(4):1016-1018.
Boumiza, et al., "The Basophil Activation Test by Flow Cytometry: Recent Developments in Clinical Studies, Standardization and Emerging Perspectives", Clinical and Molecular Allergy, vol. 3, No. 9, Jun. 30, 2005, pp. 1-8.
Burks, et al., "Peanut Allergens", Allergy, Sep. 1998, 53(8):725-730.
Burks, et al., "Peanut-Induced Anaphylactic Reactions", International Archives of Allergy and Immunology, 1992, 119:165-172, Abstract only.
Burks, A Wesley, "Peanut Allergy", The Lancet, 371(9623):1538-1546.
Busse, et al., "Recurrent Peanut Allergy", New England Journal of Medicine, vol. 347, 2002 pp. 1535-1536.
Campbell, et al., "Peptide Immunotherapy in Allergic Asthma Generates IL-10-Dependent Immunological Tolerance Associated with Linked Epitope Suppression", The Journal of Experimental Medicine, vol. 206, No. 7, pp. 1535-1547.
Chiang, et al., "Serological and Clinical Characteristics of Children with Peanut Sensitization in an Asian Community", Pediatric Allergy and Immunology, Aug. 2009, 21(2pt2):e429-e438, Abstract only.
Clark, et al., "Successful Oral Tolerance Induction in Severe Peanut Allergy", Allergy, Aug. 2009, 64(8):1218-1220, Abstract only.
Clarke, et al., "Serological Characteristics of Peanut Allergy", Clinical & Experimental Allergy, Oct. 1998, 28(10):1251-1257, Abstract only.
De Jong, et al., "Identification and Partial Characterization of Multiple Major Allergens in Peanut Proteins", Clinical & Experimental Allergy, Jun. 1998, 28(6):743-751.
De Leon, et al., "Immunological Analysis of Allergenic Cross-Reactivity Between Peanut and Tree Nuts", Clinical and Experimental Allergy, 2003, 33(9):1273-1280, Abstract only.
De Leon, et al., "The Peanut Allergy Epidemic: Allergen Molecular Characterisation and Prospects for Specific Therapy", Expert Reviews in Molecular Medicine, vol. 9, Issue 1, Jan. 2007, pp. 1-18.

De Long, et al., "Ara h 1-Reactive T Cells peanut allergic individuals", Journal of Allergy and Clinical Immunology, vol. 127, No. 5, May 2011, pp. 1211-1218.
Drew, et al., "Hypoallergenic Variants of the Major Latex Allergen Hev b 6.01 Retaining Human T Lymphocyte Reactivity", The Journal of Immunology, Nov. 2004, 173(9):5872-5879.
Eusebius, et al., "Oligoclonal Analysis of the Atopic T Cell Response to the Group 1 Allergen of *Cynodon dactylon* (Bermuda Grass) Pollen: Pre- and Post-Allergen-Specific Immunotherapy", International Archives of Allergy and Immunology, Mar. 2002, 127(3):234-244, Abstract only.
Fellrath, et al., "Allergen-Specific T-Cell Tolerance Induction with Allergen-Derived Long Synthetic Peptides: Results of a Phase I Trial", Journal of Allergy and Clinical Immunology, Apr. 2003, 111(4):854-861.
Friedl-Hajek, et al., "Identification of a Highly Promiscuous and an HLA Allele-Specific T-cell Epitope in the Birch Major Allergen Bet v 1: HLA Restriction, Epitope Mapping and TCR Sequence Comparisons", Clinical & Experimental Allergy, vol. 29, 1999, pp. 478-487.
Glaumann, et al., "Basophil Allergen Threshold Sensitivity, CD-sens, IgE-Sensitization and DBPCFC in Peanut-Sensitized Children", Allergy, Feb. 2012, 67(2):242-247, Abstract only.
Hall, et al., "Suppression of Allergen Reactive Th2 Mediated Responses and Pulmonary Eosinophilia by Intranasal Administration of an Immunodominant Peptide is Linked to IL-10 Production", Vaccine, 2003, 21(5-6):549-561, Abstract only.
Hemmer, et al., "Minimal Peptide Length Requirements for CD4+ T Cell Clones—Implications for Molecular Mimicry and T Cell Survival", International Immunology, vol. 12, Issue 3, Mar. 1, 2000, pp. 375-383.
Higgins, et al., "Overlapping T-Cell Epitopes in the Group I allergen of Dermatophagoides Species Restricted by HLA-DP and HLA-DR Class II Molecules", Journal of Allergy Clinical Immunology, vol. 93, No. 5, 1994, pp. 891-899.
Hofmann, et al., "Safety of a Peanut Oral Immunotherapy Protocol in Children with Peanut Allergy", Journal of Allergy and Clinical Immunology, Aug. 2009, 124(2):286-291.
Hourihane, et al., "An Evaluation of the Sensitivity of Subjects with Peanut Allergy to Very Low Doses of Peanut Protein: A Randomized, Double-Blind, Placebo-Controlled Food Challenge Study", Journal of Allergy and Clinical Immunology, Nov. 1997, 100(5):596-600.
Hoyne, et al., "Inhibition of T Cell and Antibody Responses to House Dust Mite Allergen by Inhalation of the Dominant T Cell Epitope in Naive and Sensitized Mice", The Journal of Experimental Medicine, Nov. 1993, 178(5):1783-1788.
Husain, et al., "Peanut Allergy: An Increasingly Common Life-Threatening Disorder", Journal of the American Academy of Dermatology, Jan. 2012, 66(1):136-143.
Jameel, et al., "Hepatitis B Virus X Protein Produced in *Escherichia coli* Is Biologically Functional", Journal of Virology, Aug. 1990, 64(8):3963-3966.
Jones, et al., "Clinical Efficacy and Immune Regulation with Peanut Oral Immunotherapy", Journal of Allergy and Clinical Immunology, Aug. 2009, 124(2):292-300.
Kammerer, et al., "Modulation of T-Cell Response to Phospholipase A2 and Phospholipase A2-Derived Peptides by Conventional Bee Venom Immunotherapy", Journal of Allergy and Clinical Immunology, vol. 100, No. 1, 1997, pp. 96-103.
Kay, et al., "Allergen Immunotherapy with Cat Allergen Peptides", Springer Seminars in Immunopathology, vol. 25, Issue 3-4, Mar. 2004, pp. 391-399.
Kemp, et al., "Food Allergy and Anaphylaxis—Dealing with Uncertainty", The Medical Journal of Australia, May 2008, 188(9):503-504.
Kinnunen, et al., "Potential of an Altered Peptide Ligand of Lipocalin Allergen Bos d 2 for Peptide Immunotherapy", The Journal of Allergy and Clinical Immunology, vol. 119, No. 4, 2007, pp. 965-972.

(56) References Cited

OTHER PUBLICATIONS

Kleber-Janke, et al., "Selective Cloning of Peanut Allergens, Including Profilin and 2S Albumins, by Phage Display Technology", International Archives of Allergy and Immunology, Aug. 1999, 119(4):265-274.

Koppelman, et al., "Quantification of Major Peanut Allergens Ara h 1 and Ara h 2 in the Peanut Varieties Runner, Spanish, Virginia, and Valencia, Bred in Different Parts of the World", Allergy, Feb. 2001, 56(2):132-137.

Kurjan, et al., "Structure of a Yeast Pheromone Gene (MFα): A Putative α-Factor Precursor Contains Four Tandem Copies of Ma-ture α-Factor", Cell, Oct. 1982, 30(3):933-943.

Kurucz, et al., "Current Animal Models of Bronchial Asthma", Current Pharmaceutical Design, vol. 12, 2006, pp. 3175-3194.

Larché, M, "Of Cats and Men: Immunodominance and the Role of HLA-DP/DQ", Clinical & Experimental Allergy, 38(11):1709-1711.

Lin, et al., "Patterns of Sensitization to Peanut Allergen Components in Taiwanese Preschool Children", Journal of Microbiology, Immunology and Infection, Apr. 2012, 45(2):90-95.

Litwin, et al., "Regulation of the Immune Response to Allergens by Immunosuppressive Allergenic Fragments", International Archives of Allergy and Immunology, 1988, 87(4):361-366.

Maguire, et al., "The Safety and Efficacy of ALLERVAX CAT in Cat Allergic Patients", Clinical Immunology, vol. 93, Issue 3, Jan. 2000, pp. 222-231.

Mannering, et al., "An Efficient Method for Cloning Human Autoantigen-Specific T Cells", Journal of Immunological Methods, Mar. 2005, 298(1-2):83-92.

Marazuela, et al., "Intranasal Immunization with a Dominant T-Cell Epitope Peptide of a Major Allergen of Olive Pollen Prevents Mice from Sensitization to the Whole Allergen", Molecular Immunology, Jan. 2008, 45(2):438-445, Abstract only.

Marcotte, et al., "Effects of Peptide Therapy on Ex Vivo T-Cell Responses", Journal of Allergy and Clinical Immunology, Apr. 1998, 101(4):506-513.

Middleton, et al., "New Allele Frequency Database", Tissue Antigens, vol. 61, Issue 5, May 2003, pp. 403-407, Abstract only.

Mittag, et al., "The Effector T Cell Response to Ryegrass Pollen Is Counterregulated by Simultaneous Induction of Regulatory T Cells", The Journal of Immunology, Mar. 2010, 184:4708-4716.

Moldaver, et al., "Immunotherapy with Peptides", Allergy, Jun. 2011, 66(6):784-791.

Movérare, et al., "Evaluation of IgE Antibodies to Recombinant Peanut Allergens in Patients with Reported Reactions to Peanut", International Archives of Allergy and Immunology, Jun. 29, 2011, 156(3):282-290.

Mukherjee, et al., "Allergic Asthma: Influence of Genetic and Environmental Factors", The Journal of Biological Chemistry, vol. 286, No. 38, 2011, pp. 32883-32889.

Muller, et al., "Successful Immunotherapy with T-Cell Epitope Peptides of Bee Venom Phospholipase A2 Induces Specific T-cell Anergy in Patients Allergic to Bee Venom", Journal of Allergy and Clinical Immunology, Jun. 1998, 101(6):747-754.

Nelson, et al., "Treatment of Anaphylactic Sensitivity to Peanuts by Immunotherapy with Injections of Aqueous Peanut Extract", Journal of Allergy and Clinical Immunology, Jun. 1997, 99(6):744-751.

Ngo, et al., "Computational Complexity, Protein Structure Prediction, and the Levinthal Paradox", The Protein Folding Problem and Tertiary Structure Prediction, 1994, 491-494.

Nopp, et al., "Basophil Allergen Threshold Sensitivity: A Useful Approach to Anti-Ige Treatment Efficacy Evaluation", Allergy, Mar. 2006, 61(3)298-302, Abstract only.

Norman, et al., "Treatment of Cat Allergy with T-Cell Reactive Peptides", American Journal of Respiratory and Critical Care Medicine, Dec. 1, 1996, 154(6):1623-1628, Abstract only.

Pumphrey, Richard, "Anaphylaxis: Can We Tell Who is at Risk of a Fatal Reaction?", Current Opinion in Allergy & Clinical Immunology, 2004, 4(4):285-290, Abstract only.

Robinson, Douglas S., "Th-2 Cytokines in Allergic Disease", British Medical Bulletin, vol. 56, Issue 4, Jan. 1, 2000, pp. 956-968.

Rolland, et al., "Allergen-Related Approaches to Immunotherapy", Pharmacology & Therapeutics, Mar. 2009, 121:273-284, Abstract only.

Rolland, et al., "Functional Regulatory T Cells and Allergen Immunotherapy", Current Opinion in Allergy and Clinical Immunology, vol. 10, Issue 6, Dec. 2010, pp. 559-566, Abstract only.

Ruiter, et al., "Role of Human Leucocyte Antigen DQ in the Presentation of T Cell Epitopes in the Major Cow's Milk Allergen αs1-Casein", International Archives of Allergy and Immunology, vol. 143, No. 2, 2007, pp. 119-126, Abstract only.

Rupa, et al., "Oral Immunotherapy with Immunodominant T-Cell Epitope Peptides Alleviates Allergic Reactions in a Balb/c Mouse Model of Egg Allergy", Allergy, Jan. 2012, 67(1):74-82, Abstract only.

Sabatos-Peyton, et al., "Antigen-Specific Immunotherapy of Autoimmune and Allergic Diseases", Current Opinion in Immunology, vol. 22, No. 5, Oct. 2010, pp. 609-615.

Sampson, et al., "Fatal and Near-Fatal Anaphylactic Reactions to Food in Children and Adolescents", The New England Journal of Medicine, vol. 327, No. 6, Aug. 6, 1992, pp. 380-384.

Sampson, et al., "Risk-Taking and Coping Strategies of Adolescents and Young Adults with Food Allergy", Journal of Allergy and Clinical Immunology, vol. 117, Issue 6, Jun. 2006, pp. 1440-1445, Abstract only.

Santambrogio, et al., "Abundant Empty Class II MHC Molecules on the Surface of Immature Dendritic Cells", PNAS, Dec. 21, 1999, 96(26):15050-15055.

Schein, et al., "Bioinformatics Approaches to Classifying Allergens and Predicting Cross-Reactivity", Immunology And Allergy Clinics of North America, vol. 27, No. 1, Feb. 2007, pp. 1-27.

Schultz, et al., "Expression and Secretion in Yeast of a 400-kda Envelope Glycoprotein Derived from Epstein-Barr Virus", Gene, 1987, 54(1):113-123.

Shek, et al., "A Population-Based Questionnaire Survey on the Prevalence of Peanut, Tree Nut, and Shellfish Allergy in 2 Asian Populations", Journal of Allergy and Clinical Immunology, vol. 126, Issue 2, Aug. 2010, pp. 324-331, Abstract only.

Shreffler, et al., "Lack of Association of HLA Class II Alleles with Peanut Allergy", Annals of Allergy, Asthma & Immunology, vol. 96, Issue 6, Jun. 2006, pp. 865-869, Abstract only.

Shreffler, et al., "Microarray Immunoassay: Association of Clinical History, in Vitro IgE Function, and Heterogeneity of Allergenic Peanut Epitopes", Journal of Allergy and Clinical Immunology, vol. 113, Issue 4, Apr. 2004, pp. 776-782, Abstract only.

Sicherer, et al., "Clinical Features of Acute Allergic Reactions to Peanut and Tree Nuts in Children", Pediatrics, Jul. 1998, 102(1):1-6.

Sicherer, et al., "Prevalence of Peanut and Tree Nut Allergy in the US Determined by a Random Digit Dial Telephone Survey", Journal of Allergy and Clinical Immunology, vol. 103, No. 4, Apr. 1999, pp. 559-562.

Sicherer, et al., "US Prevalence of Self-Reported Peanut, Tree Nut, and Sesame Allergy: 11-Year Follow-Up", Journal of Allergy and Clinical Immunology, vol. 125, Issue 6, Jun. 2010, pp. 1322-1326, Abstract only.

Singh, et al., "ProPred: Prediction of HLA-DR Binding Sites", Bioinformatics, vol. 17, Issue 12, Dec. 1, 2001, pp. 1236-1237.

Skolnick, et al., "From Genes to Protein Structure and Function: Novel Applications of Computational Approaches in the Genomic Era", Trends in Biotechnology, 2000, 18(1):34-39.

Starkl, "An unfolded variant of the major peanut allergen Ara h 2 with decreased anaphylactic potential", Clinical & Experimental Allergy, Clinical & Experimental Allergy : Journal of the British Society for Allergy and Clinical Immunology, Dec. 6, 2012, 42(12):1801-1812.

Suri, et al., "The Wide Diversity and Complexity of Peptides Bound to Class II MHC Molecules", Current Opinion in Immunology, vol. 18, No. 1, Mar. 2006, pp. 70-77, Abstract only.

Tarzi, et al., "Induction of Interleukin-10 and Suppressor of Cytokine Signalling-3 Gene Expression Following Peptide Immunotherapy", Clinical & Experimental Allergy, Apr. 2006, 36(4):465-474, Abstract only.

(56) References Cited

OTHER PUBLICATIONS

Thyagarajan, et al., "Peanut Oral Immunotherapy is not ready for Clinical Use", Journal of Allergy and Clinical Immunology, Jul. 2010, 126(1):31-32.
Van Boxtel, "Determination of Pepsin-Susceptible and Pepsin-Resistant Epitopes in Native and Heat-Treated Peanut Allergen Ara h 1", Journal of Agricultural and Food Chemistry, vol. 56, No. 6, Mar. 26, 2008, pp. 2223-2230, Abstract only.
Van De Veen, et al., "Oral Abstract Session 6: Abstract 25", Allergy, 2012, 67 (Suppl 96), 1-97, p. 12, Abstract only.
Varney, et al., "Usefulness of Immunotherapy in Patients with Severe Summer Hay Fever Uncontrolled by Antiallergic Drugs", British Medical Journal, Feb. 1, 1991, 302(6771):265-269.
Varshney, et al., "A Randomized Controlled Study of Peanut Oral Immunotherapy (OIT): Clinical Desensitization and Modulation of the Allergic", Journal of Allergy and Clinical Immunology, Mar. 2011, 127(3):654-660.
Varshney, et al., "Adverse Reactions During Peanut Oral Immunotherapy Home Dosing", Journal of Allergy and Clinical Immunology, Dec. 2009, 124(6):1351-1352.
Verhoef, et al., "Clonal Analysis of the Atopic Immune Response to the Group 2 Allergen of *Dermatophagoides* spp.: Identification of HLA-DR and -DQ Restricted T Cell Epitopes", International Immunology, vol. 5, No. 12, Jan. 1994, pp. 1589-1597.
Verhoef, et al., "T Cell Epitope Immunotherapy Induces a CD4+ T Cell Population with Regulatory Activity", PLoS Medicie, vol. 2, Issue 3, e78, Mar. 2005, 9 pages.
Vita, et al., "The Immune Epitope Database (IEDB) 3.0", Nucleic Acids Research, vol. 43, Database issue, 2015, pp. 405-412.
Vita, et al., "The Immune Epitope Database 2.0", Nucleic Acids Research, vol. 38, Issue suppl_1, Jan. 2010, pp. 854-862.
Worm, et al., "Cat Peptide Antigen Desensitisation for Treating Cat Allergic Rhinoconjunctivitis", Expert Opinion on Investigational Drugs, 2013, 22(10):1347-1357.
Worm, et al., "Development and Preliminary Clinical Evaluation of a Peptide Immunotherapy Vaccine for Cat Allergy", Journal of Allergy and Clinical Immunology, Jan. 2011, 127(1):89-97, Abstract only.
Yang, et al., "Multiple T Cell Epitope Peptides Suppress Allergic Responses in an Egg Allergy Mouse Model by the Elicitation of Forkhead Box Transcription Factor 3- and Transforming Growth Factor-Beta-Associated Mechanisms", Clinical & Experimental Allergy, Apr. 2010, 40(4):668-678, Abstract only.
Yoshitomi, et al., "Intraoral Administration of a T-Cell Epitope Peptide Induces Immunological Tolerance in Cry j 2-Sensitized Mice", Journal of Peptide Science, Aug. 2007, 13(8):499-503, Abstract only.
Yu, et al., "The Safety of Peanut Oral Immunotherapy in Peanut-Allergic Subjects in a Single-Center Trial", International Archives of Allergy and Immunology, Sep. 2012, 159(2):179-182.
Yun, et al., "Food Allergy in Adolescents and Adults", Internal Medicine Journal, vol. 39, No. 7, May 2009, pp. 475-478.
Zaunders, et al., "High Levels of Human Antigen-Specific CD4 T Cells in Peripheral Blood Revealed by Stimulated Coexpression of CD25 and CD134 (OX40)", The Journal of Immunology, 2009, 183:2827-2836.
Larché, Mark. "Mechanisms of Peptide Immunotherapy in Allergic Airways Disease", Transatlantic Airway Conference, vol. 11, Supp. 5, Dec. 2014, S292-296.
Ladics, et al., "Bioinformatics and the Allergy Assessment of Agricultural Biotechnology Products: Industry Practices and Recommendations", Regulatory Toxicology and Pharmacology, vol. 60, 2011, 46-53.
Bannon, et al., "Digestive Stability in the Context of Assessing the Potential Allergenicity of Food Proteins", Comments on Toxicology, vol. 8, 2002, 271-285.
Kane, et al., "Cross-Linking of IgE-Receptor Complexes by Rigid Bivalent Antigens >200 Å in Length Triggers Cellular Degranulation", *Journal of Biological Chemistry* 1988, 969-980.

Allen, et al., "The Evolution of Oral Immunotherapy for the Treatment of Peanut Allergy", Clinical & Experimental Allergy, Sep. 2011, 41(9):1172-1174.
Burks, et al., "Mapping and Mutational Analysis of the IgE-Binding Epitopes on Ara h 1, a Legume Vicilin Protein and a Major Allergen in Peanut Hypersensitivity", European Journal of Biochemistry, Jan. 9, 1997, vol. 245, pp. 334-339.
Yoshitomi, et al., "Intraoral Administration of a T-Cell Epitope Peptide Induces Immunological Tolerance in Cry j 2-Sensitized Mice", Journal of Peptide Science, Aug. 2007, 13(8):499-503.
Geunwoong, N. et al. (2012) Oral Sessions. Oral Abstract Session 1—"Allergen immunotherapy: new aspects in diagnostics and treatment." (Abstract 1, p. 1, "Tolerogenic effects of interferon-gamma with induction of allergen-specific interleukin-10 producing regulatory B cells (Br1) in non-IgE-mediated food allergy") Allergy (European Journal of Allergy and Clinical Immunology). 67, Suppl. 96 (2012):1-97.
Prickett, et al., "Immunoregulatory T cell epitope peptides: the new frontier in allergy therapy", Clinical & Experimental Allergy: Journal of the British Society for Allergy and Clinical Immunology, Jun. 16, 2015, 45(6):1015-1026.
Van Neerven, et al., "Characterization of Cat Dander-Specific T Lymphocytes from Atopic Patients", Journal of Immunology, Apr. 15, 1994,152(8):4203-4210.
Akdis, et al., "Bypassing IgE and Targeting T Cells for Specific Immunotherapy of Allergy", Trends in Immunology, vol. 22, No. 4, May 2001, pp. 175-178.
Akdis, et al., "Mechanisms of Allergen-Specific Immunotherapy", Journal of Allergy and Clinical Immunology, Jan. 2011, 127(1):18-27.
Akdis, et al., "Therapeutic Manipulation of Immune Tolerance in Allergic Disease", Nature Reviews Drug Discovery, Aug. 2009, 8(8):645-660.
Alexander, et al., "Fel d 1-Derived T Cell Peptide Therapy Induces Recruitment of CD4+ CD25+; CD4+ Interferon-Gamma+ T Helper Type 1 Cells to Sites of Allergen-Induced Late-Phase Skin Reactions in Cat-Allergic Subjects", Clinical & Experimental Allergy, Jan. 2005, 35(1):52-58.
Alexander, et al., "The Effect of Fel d 1-Derived T-Cell Peptides on Upper and Lower Airway Outcome Measurements in Cat-Allergic Subjects", Allergy, Oct. 2005, 60(10):1269-1274.
Anagnostou, et al., "Efficacy and Safety of High-Dose Peanut Oral Immunotherapy with Factors Predicting Outcome", Clinical & Experimental Allergy, Sep. 2011, 41(9):1273-1281.
Apostolou, et al., "Anaphylaxis to Gelofusine® Confirmed by in Vitro Basophil Activation Test: A Case Series", Anaesthesia, Apr. 2006, 61(3):264-268.
Asarnoj, et al., "IgE to Peanut Allergen Components: Relation to Peanut Symptoms and Pollen Sensitization in 8-Year-Olds", Allergy, Sep. 2010, 65(9):1189-1195.
Avery, et al., "Assessment of Quality of Life in Children with Peanut Allergy", Pediatric Allergy and Immunology, vol. 14, Issue 5, Oct. 2003, pp. 378-382.
Bateman, et al., "Identification of an Immunodominant Region of Fel d 1 and Characterization of Constituent Epitopes", Clinical & Experimental Allergy, vol. 38, Issue 11, Nov. 2008, pp. 1760-1768.
Blanc, et al., "Capacity of Purified Peanut Allergens to Induce Degranulation in a Functional in Vitro Assay: Ara h 2 and Ara h 6 are the Most Efficient Elicitors", Clinical & Experimental Allergy, Aug. 2009, 39(8):1277-1285.
Blumchen, et al., "Oral Peanut Immunotherapy in Children with Peanut Anaphylaxis", Journal of Allergy and Clinical Immunology, Jul. 2010, 126(1):83-91.
Burks, et al., "Peanut-Induced Anaphylactic Reactions", International Archives of Allergy and Immunology, 1992, 119:165-172.
Chiang, et al., "Serological and Clinical Characteristics of Children with Peanut Sensitization in an Asian Community", Pediatric Allergy and Immunology, Aug. 2009, 21(2pt2):e429-e438.
Clark, et al., "Successful Oral Tolerance Induction in Severe Peanut Allergy", Allergy, Aug. 2009, 64(8):1218-1220.
Clarke, et al., "Serological Characteristics of Peanut Allergy", Clinical & Experimental Allergy, Oct. 1998, 28(10):1251-1257.

(56) References Cited

OTHER PUBLICATIONS

De Leon, et al., "Immunological Analysis of Allergenic Cross-Reactivity Between Peanut and Tree Nuts", Clinical and Experimental Allergy, 2003, 33(9):1273-1280.
Eusebius, et al., "Oligoclonal Analysis of the Atopic T Cell Response to the Group 1 Allergen of *Cynodon dactylon* (Bermuda Grass) Pollen: Pre- and Post-Allergen-Specific Immunotherapy", International Archives of Allergy and Immunology, Mar. 2002, 127(3):234-244.
Glaumann, et al., "Basophil Allergen Threshold Sensitivity, CD-sens, IgE-Sensitization and DBPCFC in Peanut-Sensitized Children", Allergy, Feb. 2012, 67(2):242-247.
Hall, et al., "Suppression of Allergen Reactive Th2 Mediated Responses and Pulmonary Eosinophilia by Intranasal Administration of an Immunodominant Peptide is Linked to IL-10 Production", Vaccine, 2003, 21(5-6):549-561.
Marazuela, et al., "Intranasal Immunization with a Dominant T-Cell Epitope Peptide of a Major Allergen of Olive Pollen Prevents Mice from Sensitization to the Whole Allergen", Molecular Immunology, Jan. 2008, 45(2):438-445.
Middleton, et al., "New Allele Frequency Database", Tissue Antigens, vol. 61, Issue 5, May 2003, pp. 403-407.
Nopp, et al., "Basophil Allergen Threshold Sensitivity: A Useful Approach to Anti-Ige Treatment Efficacy Evaluation", Allergy, Mar. 2006, 61(3)298-302.
Norman, et al., "Treatment of Cat Allergy with T-Cell Reactive Peptides", American Journal of Respiratory and Critical Care Medicine, Dec. 1, 1996, 154(6):1623-1628.
Oldfield, et al., "Effect of T-Cell Peptides Derived from Fel d 1 on Allergic Reactions and Cytokine Production in Patients Sensitive to Cats: a Randomised Controlled Trial", The Lancet, Jul. 6, 2002, 360(9326):47-53.
Oppenheimer, et al., "Treatment of Peanut Allergy with Rush Immunotherapy", Journal of Allergy and Clinical Immunology, Aug. 1992, 90(2):256-262.
Palmer, et al., "Comparative Potency of Ara h 1 and Ara h 2 in Immunochemical and Functional Assays of Allergenicity", Clinical Immunology, Jun. 2005, 115(3):302-312.
Palmer, et al., "Current Developments in Peanut Allergy", Current Opinion in Allergy and Clinical Immunology, vol. 6, No. 3, Jul. 2006, pp. 202-206.
Peeters, et al., "Does Skin Prick Test Reactivity to Purified Allergens Correlate with Clinical Severity of Peanut Allergy?", Clinical & Experimental Allergy, Jan. 2007, 37(1):108-115.
Pomés, et al., "Quantification of Ara h 1 in Peanuts: Why Roasting Makes a Difference", Clinical & Experimental Allergy, Jun. 2006, 36(6):824-830.
Primeau, et al., "The Psychological Burden of Peanut Allergy as Perceived by Adults with Peanut Allergy and the Parents of Peanut-Allergic Children", Clinical & Experimental Allergy, Aug. 2000, 30(8):1135-1143.

Rolland, et al., "Allergen-Related Approaches to Immunotherapy", Pharmacology & Therapeutics, Mar. 2009, 121:273-284.
Rolland, et al., "Functional Regulatory T Cells and Allergen Immunotherapy", Current Opinion in Allergy and Clinical Immunology, vol. 10, Issue 6, Dec. 2010, pp. 559-566.
Ruiter, et al., "Role of Human Leucocyte Antigen DQ in the Presentation of T Cell Epitopes in the Major Cow's Milk Allergen αs1-Casein", International Archives of Allergy and Immunology, vol. 143, No. 2, 2007, pp. 119-126.
Rupa, et al., "Oral Immunotherapy with Immunodominant T-Cell Epitope Peptides Alleviates Allergic Reactions in a Balb/c Mouse Model of Egg Allergy", Allergy, Jan. 2012, 67(1):74-82.
Sampson, et al., "Risk-Taking and Coping Strategies of Adolescents and Young Adults with Food Allergy", Journal of Allergy and Clinical Immunology, vol. 117, Issue 6, Jun. 2006, pp. 1440-1445.
Shek, et al., "A Population-Based Questionnaire Survey on the Prevalence of Peanut, Tree Nut, and Shellfish Allergy in 2 Asian Populations", Journal of Allergy and Clinical Immunology, vol. 126, Issue 2, Aug. 2010, pp. 324-331.
Shreffler, et al., "Lack of Association of HLA Class II Alleles with Peanut Allergy", Annals of Allergy, Asthma & Immunology, vol. 96, Issue 6, Jun. 2006, pp. 865-869.
Shreffler, et al., "Microarray Immunoassay: Association of Clinical History, in Vitro IgE Function, and Heterogeneity of Allergenic Peanut Epitopes", Journal of Allergy and Clinical Immunology, vol. 113, Issue 4, Apr. 2004, pp. 776-782.
Sicherer, et al., "US Prevalence of Self-Reported Peanut, Tree Nut, and Sesame Allergy: 11-Year Follow-Up", Journal of Allergy and Clinical Immunology, vol. 125, Issue 6, Jun. 2010, pp. 1322-1326.
Suri, et al., "The Wide Diversity and Complexity of Peptides Bound to Class II MHC Molecules", Current Opinion in Immunology, vol. 18, No. 1, Mar. 2006, pp. 70-77.
Tarzi, et al., "Induction of Interleukin-10 and Suppressor of Cytokine Signalling-3 Gene Expression Following Peptide Immunotherapy", Clinical & Experimental Allergy, Apr. 2006, 36(4):465-474.
Van Boxtel, "Determination of Pepsin-Susceptible and Pepsin-Resistant Epitopes in Native and Heat-Treated Peanut Allergen Ara h 1", Journal of Agricultural and Food Chemistry, vol. 56, No. 6, Mar. 26, 2008, pp. 2223-2230.
Van De Veen, et al., "Oral Abstract Session 5: Abstract 26", Allergy, 2012, 67 (Suppl 96), 1-97, p. 12.
Worm, et al., "Development and Preliminary Clinical Evaluation of a Peptide Immunotherapy Vaccine for Cat Allergy", Journal of Allergy and Clinical Immunology, Jan. 2011, 127(1):89-97.
Yang, et al., "Multiple T Cell Epitope Peptides Suppress Allergic Responses in an Egg Allergy Mouse Model by the Elicitation of Forkhead Box Transcription Factor 3- and Transforming Growth Factor-Beta-Associated Mechanisms", Clinical & Experimental Allergy, Apr. 2010, 40(4):668-678.

* cited by examiner

Core Epitope:
ELNEFENNQRCMCEALQQIM SEQ. ID# 56

FIG. 12
1) Pool 1 (7 x Ara h 1 'long' candidates; all Ara h 1 epitopes)
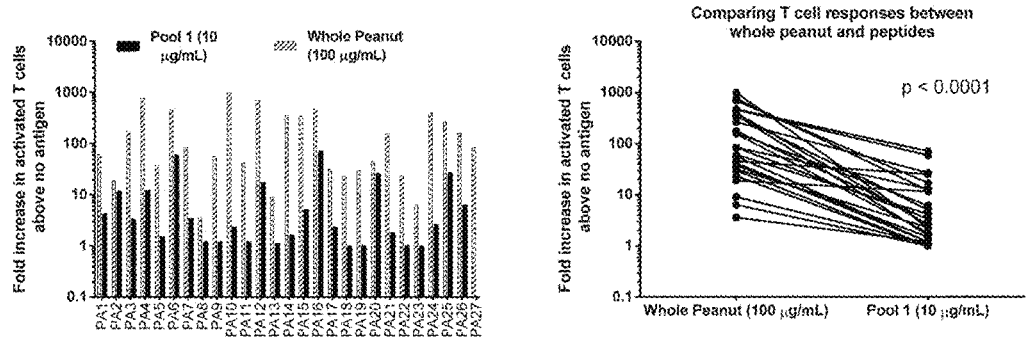
2) Pool 2 (3 x Ara h 2 'long' candidates; all Ara h 2 epitopes)
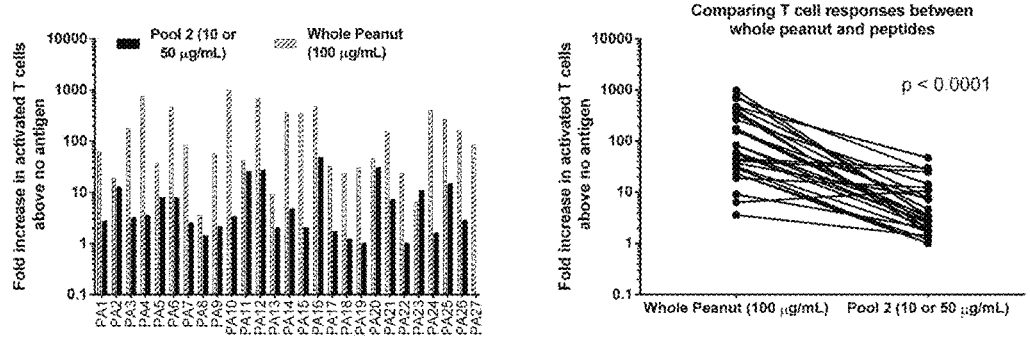
3) Pool 3 (7 x Ara h 1 'long' + 3 x Ara h 2 candidates; all Ara h 1 & 2 epitopes)
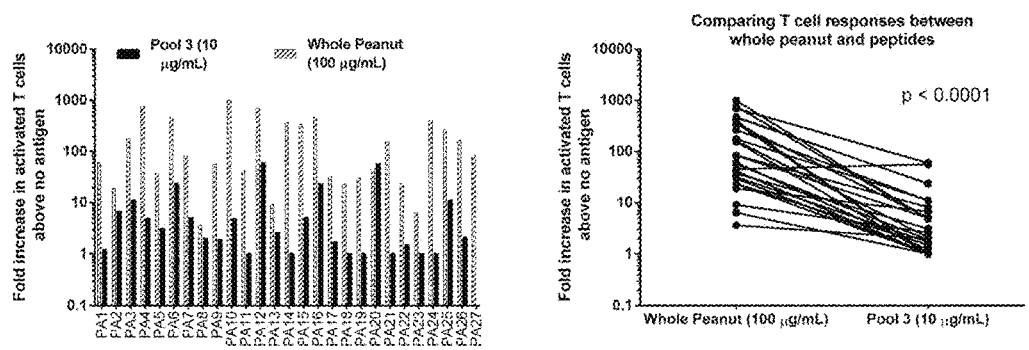

FIG. 12 (continued)
4) Pool 4 (3 x Ara h 1 'long' candidates + 5 x short Ara h 1 single epitopes; all Ara h 1 epitopes)
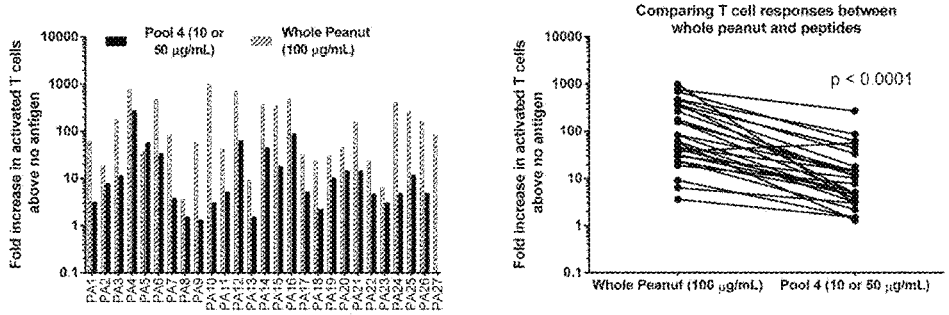
5) Pool 5 (5 x Ara h 2 short (single epitopes); all Ara h 2 epitopes)
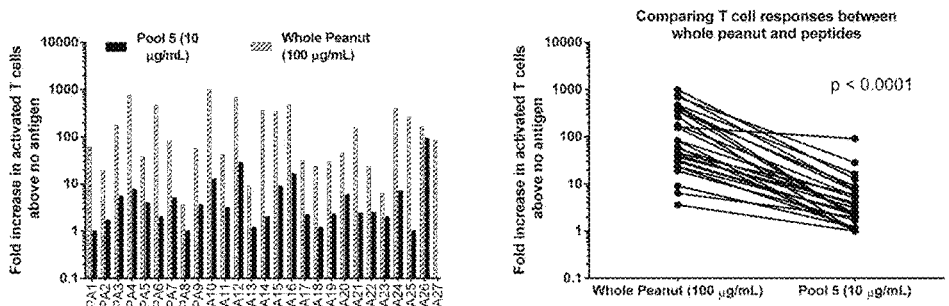

FIG. 13
6) Pool 7a (refined 8-peptide pool from 23-peptide screen; 5 x Ara h 1 & 3 x Ara h 2 peptide
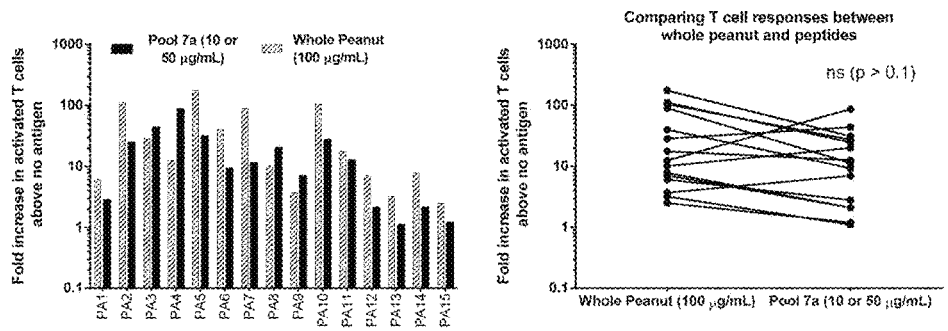
7) Pool 7b (final 7-peptide pool from 23-peptide screen; 5 x Ara h 1 & 2 x Ara h 2 peptides)
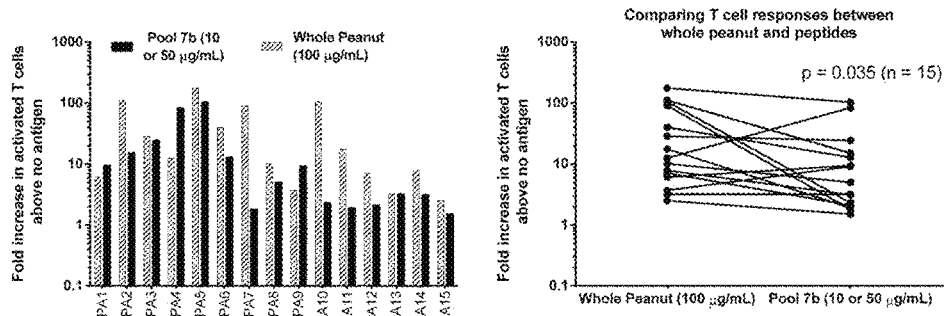
8) Pools 7b for larger cohort (n = 30)
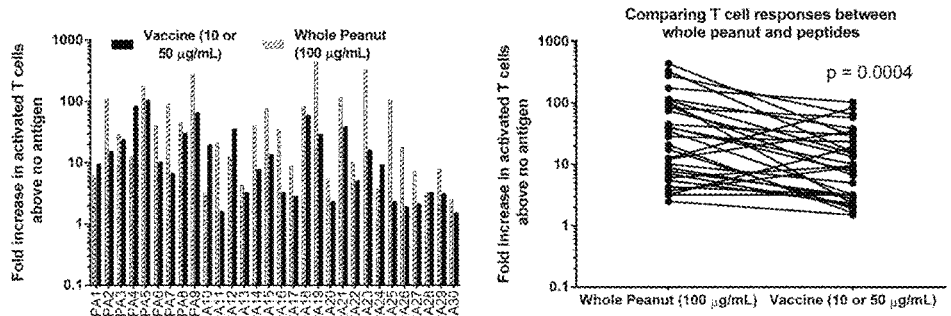

FIG. 14
8) No significant difference between pools 7a and 7b
*(comparing paired data; n = 15 per group; No advantage adding 3rd Ara h 2 peptide)*
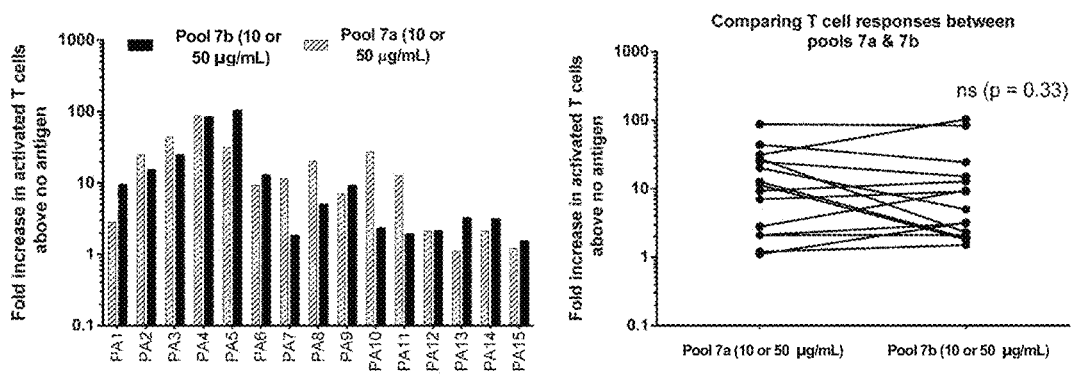
9) Pool 7b (and 7a) significantly better than most other pools tested
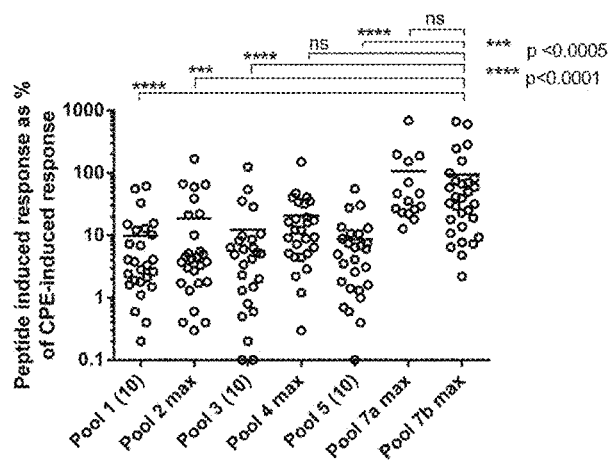

FIG. 17

*Therapeutic candidate peptides of Ara h 1 and Ara h 2*

| Sequence | HLA | Sequence | HLA |
|---|---|---|---|
| FQNLQNHRIVQIEAKPNTLV (SEQ ID NO: 11) | DR | KAMVIVVVNKGTGNLELVAVDR (SEQ ID NO: 40) | DR |
| *STRSSENNEGVIVKVSKE[1] (SEQ ID NO: 12) | DQ | *GDVFIMPAAHPVAINASSE[2] (SEQ ID NO: 18) | DQ+DR |
| NNFGKLFEVKPDKKNPQLQ (SEQ ID NO: 17) | DR | *SQLERANLRPSEQHLM[3] (SEQ ID NO: 105) | DP+DQ+DR |
| VEIKEGALMLPHFNSKA (SEQ ID NO: 13) | DQ+DR | *ELNEFENNQRSMSEALQ[3] (SEQ ID NO: 106) | DR+DQ |
| ALMLPHFNSKAMVIVVV (SEQ ID NO: 33) | DR | *RELRNLPQQSGLRA[3] (SEQ ID NO: 107) | DR |

Ara h 1 peptides shaded; Ara h 2 peptides unshaded. HLA column shows HLA types known to present T cell epitope(s) within the peptide. *Peptides altered to improve properties; [1] 'W' omitted from N-terminus. [2] 'E' (from native sequence) added to C-terminus. [3] Bolded serine replaced a cysteine.

*Proliferative responses (thymidine uptake) of TCL to Ara h 1 20-mer peptides*

FIG. 19

*SIs of peptide-induced proliferation for 24 subjects*

| Subject | No Antigen* | CPE | \multicolumn{9}{c}{Stimulation Indices (SI) Ara h 1 20-mers} | | | | | | | | | +ve 20-mers SI>1.1 | | SI>1.5 | |
|---|---|---|---|---|---|---|---|---|---|---|---|---|---|---|---|
| | | | 23 | 24 | 40 | 46 | 47 | 49 | 50 | 51 | 57 | No. | % | No. | % |
| 19 | 0.22 | 91.6 | 3.5 | 0.7 | 3.3 | nt | nt | nt | 0.7 | 3.2 | 36.0 | 4/6 | 67 | 4/6 | 67 |
| 20 | 0.08 | 1.4 | 1.1 | 1.4 | 0.0 | nt | nt | nt | 1.0 | 69.3 | 0.0 | 3/6 | 50 | 1/6 | 17 |
| 21 | 0.45 | 7.0 | 0.4 | 2.8 | 0.5 | nt | nt | nt | 0.3 | 1.0 | 0.4 | 1/6 | 17 | 1/6 | 17 |
| 22 | 0.27 | 54.6 | 0.4 | 0.9 | 0.2 | nt | nt | nt | 1.7 | 0.5 | 0.2 | 1/6 | 17 | 1/6 | 17 |
| 23 | 3.02 | 5.9 | 0.6 | 0.8 | 1.0 | nt | nt | nt | 1.2 | 0.4 | 2.0 | 2/6 | 33 | 1/6 | 17 |
| 24 | 0.26 | 6.8 | 0.5 | 0.5 | 0.6 | nt | nt | nt | 2.8 | 2.0 | 0.7 | 2/6 | 33 | 2/6 | 33 |
| 25 | 0.10 | 152.0 | 2.2 | 1.2 | 0.6 | 23.4 | 1.9 | 3.1 | 0.9 | 0.4 | 0.7 | 5/9 | 56 | 4/9 | 44 |
| 26 | 0.07 | 122.8 | 2.3 | 5.8 | 0.9 | 0.6 | 1.3 | 12.7 | 4.2 | 4.4 | 2.7 | 7/9 | 78 | 6/9 | 67 |
| 27 | 0.17 | 1.4 | 0.6 | 0.8 | 0.9 | 1.0 | 0.7 | 1.3 | 0.6 | 1.1 | 1.5 | 3/9 | 33 | 1/9 | 11 |
| 28 | 0.06 | 37.5 | 5.6 | 8.9 | 6.0 | 18.0 | 1.7 | 2.5 | 3.0 | 12.6 | 29.5 | 9/9 | 100 | 9/9 | 100 |
| 29 | 1.87 | 2.9 | 1.7 | 1.7 | 1.3 | 0.7 | 1.1 | 1.6 | 1.6 | 1.7 | 1.8 | 8/9 | 89 | 6/9 | 67 |
| 30 | 0.11 | 2.1 | 1.5 | 2.6 | 1.7 | 0.9 | 0.9 | 1.2 | 0.4 | 2.1 | 0.5 | 5/9 | 56 | 4/9 | 44 |
| 31 | 0.08 | 10.3 | 1.9 | 2.1 | 1.2 | 2.5 | 9.0 | 1.9 | 1.5 | 1.3 | 2.0 | 9/9 | 100 | 7/9 | 78 |
| 32 | 0.06 | 5.8 | 0.8 | 2.4 | 1.3 | 1.2 | 1.6 | 2.3 | 10.2 | 0.9 | 1.3 | 7/9 | 78 | 4/9 | 44 |
| 33 | 1.30 | 2.3 | 1.8 | 0.4 | 0.8 | 1.5 | 1.2 | 0.9 | 0.8 | 0.1 | 0.2 | 3/9 | 33 | 2/9 | 22 |
| 34 | 1.04 | 1.6^ | 2.1 | 1.0 | 2.8 | 2.4 | 2.3 | 1.5 | 0.3 | 2.0 | 4.1 | 6/9 | 66 | 6/9 | 66 |
| 35 | 0.08 | 8.2^ | 1.0 | 0.8 | 1.3 | 0.5 | 3.3 | 5.3 | 0.3 | 0.8 | 2.0 | 4/9 | 44 | 3/9 | 33 |
| 36 | 0.35 | 6.1^ | 1.6 | 1.4 | 1.6 | 1.7 | 4.8 | 2.6 | 0.8 | 1.2 | 1.5 | 8/9 | 89 | 7/9 | 78 |
| 37 | 1.05 | 7.8 | 0.3 | 0.3 | 0.3 | 0.6 | 0.2 | 0.9 | 0.7 | 0.9 | 0.3 | 0/9 | 0 | 0/9 | 0 |
| 38 | 0.78 | 1.3 | 0.8 | 0.9 | 0.8 | 0.7 | 0.9 | 0.9 | 0.7 | 0.7 | 0.8 | 0/9 | 0 | 0/9 | 0 |
| Responders w SI>1.1 | # | 20/20 | 11/20 | 10/20 | 8/20 | 7/14 | 10/14 | 11/14 | 8/20 | 11/20 | 11/20 | | | | |
| | % | 100 | 55 | 50 | 40 | 50 | 71 | 79 | 40 | 55 | 55 | | | | |
| Responders w SI>1.5 | # | 17/20 | 10/20 | 7/20 | 4/20 | 6/14 | 7/14 | 9/14 | 7/20 | 8/20 | 10/20 | | | | |
| | % | 85 | 50 | 35 | 20 | 43 | 50 | 64 | 35 | 40 | 50 | | | | |
| 1 | 0.17 | 7.1^ | 2.4 | 2.7 | 1.8 | 1.1 | 1.7 | 2.5 | 0.4 | 0.5 | 1.2 | 7/9 | 78 | 5/9 | 56 |
| 2 | 0.19 | 83.5 | 1.8 | 10.3 | 1.6 | 1.8 | 1.0 | 1.6 | 3.4 | 1.9 | 2.9 | 8/9 | 89 | 8/9 | 89 |
| 4 | 0.62 | 12.3 | 5.2 | 1.8 | 4.2 | nt | nt | nt | 4.7 | 6.5 | 9.7 | 6/6 | 100 | 6/6 | 100 |
| 10 | 0.23 | 44.4 | 14.4 | 5.3 | 5.3 | nt | nt | nt | 14.2 | 8.1 | 4.4 | 6/6 | 100 | 6/6 | 100 |
| Responders w SI>1.1 | # | 24/24 | 15/24 | 14/24 | 12/24 | 9/16 | 11/16 | 13/16 | 11/24 | 14/24 | 15/24 | | | | |
| | % | 100 | 63 | 58 | 50 | 56 | 69 | 81 | 46 | 58 | 63 | | | | |
| Responders w SI>1.5 | # | 21/24 | 14/24 | 11/24 | 8/24 | 7/16 | 8/16 | 11/16 | 10/24 | 11/24 | 13/24 | | | | |
| | % | 88 | 58 | 46 | 33 | 44 | 50 | 69 | 42 | 46 | 54 | | | | |

FIG. 20

*Proliferative responses (thymidine uptake) of TCL to Ara h 2 20-mer peptides*

FIG. 21

*Core T cell epitopes found in dominant Ara h 1 20-mers*

| 20-mer peptide | | Minimum sequence required for T-cell recognition | | Consolidated epitope (common core underlined) | | Confirmed Responders | |
|---|---|---|---|---|---|---|---|
| # | Residues | Residues | Sequence | Residues/aa | Sequence | TCL | Sub-jects |
| 23 | (199-218) | (206-213) | FQNLQNHR (SEQ ID NO:1) | (206-215) 10 aa | FQNLQNHRIV (SEQ ID NO:21) | 6 | 3 |
| | | (206-215) | FQNLQNHRIV (SEQ ID NO:21) | | | | |
| 24 | (208-227) | (213-222) | RIVQIEAKPN (SEQ ID NO:58) | (213-225) 13 aa | RIVQIEAKPNTLV (SEQ ID NO:22) | 6 | 3 |
| | | (213-225) | RIVQIEAKPNTLV (SEQ ID NO:22) | | | | |
| | | (214-219) | IVQIEA (SEQ ID NO:2) | | | | |
| 40 | (352-371) (SEQ ID NO:23) | (353-371) | WSTRSSENNEGVIVKVSKE (SEQ ID NO:59) | (353-371) 19 aa | WSTRSSENNEGVIVKVSKE* (SEQ ID NO:59) | 3 | 3 |
| | | (359-371) | ENNEGVIVKVSKE | | | | |
| | (SEQ ID NO:3) | (361-370) | NEGVIVKVSK | | | | |
| 46 | (406-425) (SEQ ID NO:34) | (409-418) | NNFGKLFEVK (SEQ ID NO:61) | (409-425) 17 aa | NNFGKLFEVKPDKKNPQ (SEQ ID NO:34) | 3 | 2 |
| | | (409-425) | NNFGKLFEVKPDKKNPQ | | | | |
| | (SEQ ID NO:62) | (411-418) | FGKLFEVK | | | | |
| 47 | (415-434) | (416-427) | EVKPDKKNPQLQ (SEQ ID NO:4) | (416-427) 12 aa | EVKPDKKNPQLQ (SEQ ID NO:4) | 2 | 1 |
| 49 | (433-452) | (436-445) | VEIKEGALML (SEQ ID NO:63) | (436-452) 17 aa | VEIKEGALMLPHFNSKA* (SEQ ID NO:13) | 5 | 2 |
| | (SEQ ID NO:64) | (436-449) | VEIKEGALMLPHFN | | | | |
| | (SEQ ID NO:65) | (440-452) | EGALMLPHFNSKA | | | | |
| 50 | (442-461) | (442-458) | ALMLPHFNSKAMVIVVV (SEQ ID NO:33) | (442-458) 17 aa | ALMLPHFNSKAMVIVVV* (SEQ ID NO:33) | 6 | 3 |
| | (SEQ ID NO:66) | (443-457) | LMLPHFNSKAMVIVV | | | | |
| | (SEQ ID NO:67) | (446-456) | PHFNSKAMVIV | | | | |
| | (SEQ ID NO:68) | (451-459) | KAMVIVVVN | (451-461) 11 aa | KAMVIVVVNKG (SEQ ID NO:42) | 3 | 2 |
| | (SEQ ID NO:69) | (452-461) | AMVIVVVNKG | | | | |
| | (SEQ ID NO:70) | (455-461) | IVVVNKG | | | | |
| 51 | (451-470) | (452-467) | AMVIVVVNKGTGNLEL (SEQ ID NO:71) | (452-470) 19 aa | AMVIVVVNKGTGNLELVAV (SEQ ID NO:34) | 7 | 4 |
| | (SEQ ID NO:43) | (452-468) | AMVIVVVNKGTGNLELV | | | | |
| | (SEQ ID NO:72) | (457-469) | VVNKGTGNLELVA | | | | |
| | (SEQ ID NO:73) | (457-470) | VVNKGTGNLELVAV | | | | |
| 57 | (505-524) | (507-524) | GDVFIMPAAHPVAINASS (SEQ ID NO:29) | (507-524) 18 aa | GDVFIMPAAHPVAINASS* (SEQ ID NO:29) | 12 | 4 |
| | (SEQ ID NO:74) | (509-524) | VFIMPAAHPVAINASS | | | | |
| | (SEQ ID NO:75) | (510-521) | FIMPAAHPVAIN | | | | |
| | (SEQ ID NO:6) | (511-517) | IMPAAHP | | | | |
| | (SEQ ID NO:76) | (511-521) | IMPAAHPVAIN | | | | |

FIG. 22
*Core T cell epitopes found in dominant Ara h 2 20-mers*

| Dominant 20-mer | | | Minimum sequence required for T cell recognition | Consolidated epitope (common core underlined) Sequence | Residues | Confirmed Responders |
|---|---|---|---|---|---|---|
| Name | Residues | Sequence | | | | |
| 20-mer 4 | 28-47 | (SEQ ID NO:54) RRCQSQLERANLRPCEQHLM | (SEQ ID NO: 77) SQLERANLRPCEQ | SQLERANLRPCEQ (SEQ ID NO:77) | 32-44 | 2 patients, 5 TCL |
| | | | (SEQ ID NO:78) SQLERANLRPC | | | |
| | | | (SEQ ID NO:79) LERANLRPC | | | |
| | | | (SEQ ID NO:80) LERANLRPCEQ | | | |
| | | | (SEQ ID NO:81) ERANLRPCEQ | | | |
| | | | (SEQ ID NO:82) ANLRPCEQHLM | ANLRPCEQHLM (SEQ ID NO: 82) | 37-47 | 4 patients, 9+TCL |
| | | | (SEQ ID NO:83) LRPCEQHLM | | | |
| 20-mer 11 | 91-110 | (SEQ ID NO:56) ELNEFENNQRCMCEALQQIM | (SEQ ID NO:84) ELNEFENNQRCM | ELNEFENNQRCM (SEQ ID NO:84) | 91-102 | 3 patients, 6 TCL |
| | | | (SEQ ID NO:85) LNEFENNQRCM | | | |
| | | | (SEQ ID NO:86) EFENNQRCMCEALQ | EFENNQRCMCEALQ (SEQ ID NO:86) | 94-107 | 3 peptides, 4 TCL |
| | | | (SEQ ID NO:87) ENNQRCMCEA | | | |
| | | | (SEQ ID NO:88) NNQRCMCEALQ | | | |
| 20-mer 15 | 127-146 | (SEQ ID NO:57) KRELRNLPQQCGLRAPQRCD | (SEQ ID NO: 89) RELRNLPQQCGL | (SEQ ID NO:94) RELRNLPQQCGLRA | 128-141 | 5 peptides, 7 TCL |
| | | | (SEQ ID NO:90) ELRNLPQQCGLR | | | |
| | | | (SEQ ID NO:91) ELRNLPQQCGL | | | |
| | | | (SEQ ID NO:92) LRNLPQQCGL | | | |
| | | | (SEQ ID NO:93) LRNLPQQCG | | | |

FIG. 23

*HLA-restriction of Ara h 1 and Ara h 2 T cell epitope presentation*

*Grey shading indicates T cell epitopes included in current 7-peptide mix*

| 20-mer | T cell Epitope | Subject | HLA-restriction | Corresponding HLA-allele(s) | |
|---|---|---|---|---|---|
| 23 | (206-215) | 18 | HLA-DR | DRB1 04:05 | DRB1 15:01 |
| | | 3 | HLA-DR | DRB1 03:01 | DRB1 08:01 |
| 24 | (213-225) | 12 | HLA-DR | DRB1 08:01 | DRB1 10:01 |
| | | 10 | HLA-DR | DRB1 11:01 | DRB1 15:01 |
| 40 | (353-371) | 4 | HLA-DQ | DQB1 03:01 | DQB1 06:02 |
| | | 13 | HLA-DQ | DQB1 03:01 | DQB1 06:02 |
| | | 14 | nt | DQB1 06:09 | |
| 46 | (409-425) | 16 | HLA-DR | DRB1 04:04 | DRB1 13:01 |
| | | 15 | nt | DRB1 03:01P | DRB1 04:01 |
| 47 | (416-427) | 16 | HLA-DR | DRB1 04:04 | DRB1 13:01 |
| | | 15 | nt | DRB1 03:01P | DRB1 04:01 |
| 49 | (436-452) | 18 | HLA-DQ | DQB1 03:02 | DQB1 06:02 |
| | | | HLA-DR | DRB1 04:05 | DRB1 15:01 |
| 50 | (442-458) | 17 | HLA-DR | DRB1 11:04 | DRB1 15:01 |
| | | 9 | HLA-DR | DRB1 09:01 | DRB1 13:01 |
| 50+51 | (451-461) | 12 | HLA-DR | DRB1 08:01 | DRB1 10:01 |
| | | 6 | HLA-DR | DRB1 04:01 | DRB1 04:04 |
| 51 | (452-470) | 10 | HLA-DR | DRB1 11:01 | DRB1 15:01 |
| | | 14 | nt | DRB1 13:02 | |
| 57 | (507-524) | 17 | HLA-DR | DRB1 11:04 | DRB1 15:01 |
| | | 13 | HLA-DQ | DQB1 03:01 | DQB1 06:02 |

FIG. 24

Nt = HLA-restriction not tested

*HLA-restriction of Ara h 2 epitope presentation*

| T cell Epitope | HLA-genotyping for subjects recognising each T cell epitope | | | | | | Known HLA Restriction |
|---|---|---|---|---|---|---|---|
| | DR B1 | | DQ B1 | | DP B1 | | |
| A: SQLERANLRPCEQ (SEQ ID NO:77) | 1201G | 1501 | 0301 | 0602 | 0902/1301 | 0401 | DP |
| | 1001 | 0801 | 0402 | 0501 | 0301G | 0401 | DP |
| | 0301 | 0801 | 0201G | 0402 | 0301G | 0401 | NT |
| | 0404 | 0401 | 0302 | 0402 | 0902/1301 | 0401 | NT |
| | | | | | | | |
| B: ANLRPCEQHLM (SEQ ID NO:82) | 0901 | 1301 | 0303 | 0603 | 0301G | 0402/0602 | DR |
| | 1201G | 1501 | 0301 | 0602 | 1301/0902 | 0401 | DR |
| | 0301 | 1302 | 0201G | 0609 | 0101 | 0401 | DQ |
| | | 1302 | | 0609 | 0501 | 0402/0602 | DQ |
| | | | | | | | |
| C: ELNEFENNQRCM (SEQ ID NO:84) | 1201G | 1501 | 0301 | 0602 | 1301/0902 | 0401 | DR |
| | 1101 | 1501 | 0301G | 0602 | | 0401 | DR |
| | | | | | | | |
| D: EFENNQRCMCEALQ (SEQ ID NO:86) | 1201G | 1501 | 0301 | 0602 | 1301/0902 | 0401 | DQ |
| | 0103 | 0401 | 0302 | 0501 | 0301G | 0201 | DQ |
| | 1001 | 0801 | 0402 | 0501 | 0301G | 0401 | NT |
| | 0404 | 0401 | 0302 | 0402 | 0902/1301 | 0401 | NT |
| | | 1302 | | 0609 | 0501 | 0402/0602 | NT |
| | 0701 | 1501 | 0201G | 0602 | 0201 | 0401 | NT |
| | 1101 | 1501 | 0301G | 0602 | 0301G | 0401 | NT |
| | | | | | | | |
| E: RELRNLPQQCGLRA (SEQ ID NO:94) | 1101 | 1501 | 0301G | 0602 | | 0401 | DR |
| | 0405 | 1501 | NA | 0602 | 0301G | 0401 | DR |
| | 0404 | 1301 | 0302 | 0603 | 0201 | 0401 | DR |
| | 0901 | 1301 | 0303 | 0603 | 0301G | 0402/0602 | NT |
| | | 1302 | | 0609 | 0501 | 0402/0602 | NT |
| | 1101 | 1501 | 0301G | 0602 | | 0401 | NT |
| | 0701 | 1501 | 0201G | 0602 | 0201 | 0401 | NT |
| | 0404 | 0401 | 0301G | 0302 | 0201 | 0401 | NT |

| HLA-DRB alleles | Freq in US caucasians | multi-pred: Hidden Markov Method; >7 | | | Propred prediction: Sturniolo; top 3% | | |
|---|---|---|---|---|---|---|---|
| | | Ara h 2 pep 4 | Ara h 2 pep 11 | Ara h 2 pep 15 | Ara h 2 pep 4 | Ara h 2 pep 11 | Ara h 2 pep 15 |
| DRB1_0101: | 9.1 | LERANLRPC (SEQ ID NO:79) LRPCEQHLM (SEQ ID NO:83) | FENNQRCMC (SEQ ID NO:96) LNEFENNQRC (SEQ ID NO:97) | LRNLPQQCG (SEQ ID NO:98) LPQQCGLRA (SEQ ID NO:99) | | | LRNLPQQCG (SEQ ID NO:98) |
| DRB1_0102: | 1.4 | | | | LRPCEQHLM (SEQ ID NO:83) | | LRNLPQQCG (SEQ ID NO:98) |
| DRB1_0301: | 13.1 | LERANLRPC (SEQ ID NO:79) LRPCEQHLM (SEQ ID NO:83) | FENNQRCMC (SEQ ID NO:96) LNEFENNQRC (SEQ ID NO:97) | LRNLPQQCG (SEQ ID NO:98) LPQQCGLRA (SEQ ID NO:99) | | | |
| DRB1_0305: | | | | | | FENNQRCMC (SEQ ID NO:96) | |
| DRB1_0306: | | | | | | | |
| DRB1_0307: | | | | | | | |
| DRB1_0308: | | | | | | | |
| DRB1_0309: | | | | | | | |
| DRB1_0311: | | (SEQ ID NO:79) | | (SEQ ID NO:98) | | | |
| DRB1_0401: | 5.4 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | | | |
| DRB1_0402: | 1 | | | | | | |
| DRB1_0404: | 3.9 | | | | | | |
| DRB1_0405: | 0.3 | | | | | | |
| DRB1_0408: | | | | | | | |
| DRB1_0410: | | | | | | | |
| DRB1_0421: | | | | | | | |
| DRB1_0423: | | | | | | | |
| DRB1_0426: | | (SEQ ID NO:79) | (SEQ ID NO:96) | (SEQ ID NO:98) | | | |
| DRB1_0701: | 14.8 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | | | |
| DRB1_0703: | | (SEQ ID NO:79) | (SEQ ID NO:96) | (SEQ ID NO:98) | | | |
| DRB1_0801: | 2.2 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | | | |
| DRB1_0802: | | | | | | FENNQRCMC (SEQ ID NO:96) | |
| DRB1_0804: | | | | | | | |
| DRB1_0806: | | | | | | | |
| DRB1_0813: | | | | | | | |
| DRB1_0817: | | (SEQ ID NO:79) | (SEQ ID NO:96) | (SEQ ID NO:98) | | | |
| DRB1_1101: | 5.6 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | (SEQ ID NO:79) LERANLRPC LRPCEQHLM (SEQ ID NO:83) | FENNQRCMC | |
| DRB1_1102: | | | | | | | |
| DRB1_1104: | 2.7 | | | | | | |
| DRB1_1106: | | | | | | | |
| DRB1_1107: | | | | | | | |
| DRB1_1114: | | | | | | FENNQRCMC (SEQ ID NO:96) | |
| DRB1_1120: | | | | (SEQ ID NO:83) | LRPCEQHLM | | |
| DRB1_1121: | | | | (SEQ ID NO:79) (SEQ ID NO:83) | LERANLRPC LRPCEQHLM | | |
| DRB1_1128: | | (SEQ ID NO:79) | (SEQ ID NO:96) | (SEQ ID NO:98) | | | |
| DRB1_1301: | 5.6 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | LRPCEQHLM (SEQ ID NO:83) LRPCEQHLM (SEQ ID NO:83) | | LRNLPQQCG (SEQ ID NO:98) |
| DRB1_1302: | 0.7 | | | | | | |
| DRB1_1304: | | | | | LRPCEQHLM (SEQ ID NO:83) | | LRNLPQQCG (SEQ ID NO:98) |
| DRB1_1305: | | | | | | | |
| DRB1_1307: | | | | | | FENNQRCMC (SEQ ID NO:96) | |
| DRB1_1311: | | | | | | | |
| DRB1_1321: | | | | | | | |
| DRB1_1322: | | | | | (SEQ ID NO:79) LERANLRPC (SEQ ID NO:83) LRPCEQHLM | | |
| DRB1_1323: | | | | | (SEQ ID NO:83) LRPCEQHLM | FENNQRCMC (SEQ ID NO:96) | (SEQ ID NO:98) LRNLPQQCG |
| DRB1_1327: | | | | | | | |
| DRB1_1328: | | (SEQ ID NO:79) | (SEQ ID NO:96) | (SEQ ID NO:98) | LRPCEQHLM (SEQ ID NO:83) | | LRNLPQQCG (SEQ ID NO:98) |
| DRB1_1501: | 14.2 | LERANLRPC LRPCEQHLM (SEQ ID NO:83) | FENNQRCMC LNEFENNQRC (SEQ ID NO:97) | LRNLPQQCG LPQQCGLRA (SEQ ID NO:99) | | | |
| DRB1_1502: | 0.7 | | | | | | |
| DRB1_1506: | | | | | | | |
| DRB5_0101: | | | | | | | |
| DRB5_0105: | | | | | | | |

FIG. 27

*Combining overlapping Ara h 1 T cell epitopes into single peptides ≤20 aa long*

| 20-mer peptide | | Minimum sequence required for T-cell recognition | | Consolidated epitope (common core underlined) | | Confirmed Responders | |
|---|---|---|---|---|---|---|---|
| # | Residues | Residues | Sequence | Residues/aa | Sequence | TCL | Sub-jects |
| 23 (199-218) | | (206-213) | FQNLQNHR (SEQ ID NO:1) | (206-215) 10 aa | FQNLQNHRIV (SEQ ID NO:21) | 6 | 3 |
| | | (206-215) | FQNLQNHRIV (SEQ ID NO:21) | | | | |
| 24 (208-227) | | (213-222) | RIVQIEAKPN (SEQ ID NO:58) | (213-225) 13 aa | RIVQIEAKPNTLV (SEQ ID NO:22) | 6 | 3 |
| | | (213-225) | RIVQIEAKPNTLV (SEQ ID NO:22) | | | | |
| | | (214-219) | IVQIEA (SEQ ID NO:2) | | | | |
| | | Overlapping epitopes combined | | (206-225) 20 aa | FQNLQNHRIVQIEAKPNTLV* (SEQ ID NO:11) | 12 | 6 |
| 40 (352-371) (SEQ ID NO:23) (SEQ ID NO:3) | | (353-371) (359-371) (361-370) | (SEQ ID NO:59) WSTRSSENNEGVIVKVSKE ENNEGVIVKVSKE NEGVIVKVSK | (353-371) 19 aa | WSTRSSEN<u>NEGVIVKVSKE</u>* (SEQ ID NO:59) | 3 | 3 |
| 46 (406-425) (SEQ ID NO:34) (SEQ ID NO:63) | | (409-418) (409-425) (411-418) | NNFGKLFEVK (SEQ ID NO:61) NNFGKLFEVKPDKKNPQ FGKLFEVK | (409-425) 17 aa | NN<u>FGKLFEVK</u>PDKKNPQ (SEQ ID NO:34) | 3 | 2 |
| 47 (415-434) | | (416-427) | EVKPDKKNPQLQ (SEQ ID NO:4) | (416-427) 12 aa | <u>EVKPDKKNPQLQ</u> (SEQ ID NO:4) | 2 | 1 |
| | | Overlapping epitopes combined | | (409-427) 19 aa | NNFGKLFEVKPDKKNPQLQ* (SEQ ID NO:17) | 3 | 2 |
| 49 (433-452) (SEQ ID NO:65) | | (436-445) (436-449) (440-452) | VEIKEGALML (SEQ ID NO:63) VEIKEGALMLPHFN (SEQ ID NO:64) EGALMLPHFNSKA | (436-452) 17 aa | VEIK<u>EGALML</u>PHFNSKA* (SEQ ID NO:13) | 5 | 2 |
| 50 (442-461) (SEQ ID NO:66) (SEQ ID NO:67) | | (442-458) (443-457) (446-456) | ALMLPHFNSKAMVIVVV (SEQ ID NO:33) LMLPHFNSKAMVIVV PHFNSKAMVIV | (442-458) 17 aa | ALML<u>PHFNSKAMVIV</u>VV* (SEQ ID NO:33) | 6 | 3 |
| (SEQ ID NO:68) (SEQ ID NO:69) (SEQ ID NO:70) | | (451-459) (452-461) (455-461) | KAMVIVVVN AMVIVVVNKG IVVVNKG | (451-461) 11 aa | KAMV<u>IVVVNKG</u> (SEQ ID NO:42) | 3 | 2 |
| 51 (451-470) (SEQ ID NO:45) (SEQ ID NO:72) (SEQ ID NO:73) | | (452-467) (452-468) (457-469) (457-470) | AMVIVVVNKGTGNLEL (SEQ ID NO:71) AMVIVVVNKGTGNLELV VVNKGTGNLELVA VVNKGTGNLELVAV | (452-470) 19 aa | AMVIVV<u>VNKGTGNLEL</u>VAV (SEQ ID NO:74) | 7 | 4 |
| | | Overlapping epitopes combined | | (451-470) 20 aa | KAMVIVVVNKGTGNLELVAV* (SEQ ID NO:40) | 10 | 6 |
| 57 (505-524) (SEQ ID NO:14) (SEQ ID NO:75) (SEQ ID NO:6) (SEQ ID NO:76) | | (507-524) (509-524) (510-521) (511-517) (511-521) | GDVFIMPAAHPVAINASS (SEQ ID NO:29) VFIMPAAHPVAINASS FIMPAAHPVAIN IMPAAHP IMPAAHPVAIN | (507-524) 18 aa | GDVF<u>IMPAAHP</u>VAINASS* (SEQ ID NO:29) | 12 | 4 |

*Grey shading indicates overlapping consolidated T cell epitope pairs combined into single peptides for further analyses as outlined in the text. \* Asterisks and boxes indicate the seven Ara h 1 candidate peptides proposed for a therapeutic.*

FIG. 28

Summary of responses to 23-peptide panel in expanded cohort of 34

Dark grey boxes indicate groups with feasible alternate peptides to add/substitute into current pool.

Alternate Summary of PBMC T cell responses to full set of candidate peptides in 25 peanut-allergic subject

Summary of responses to each peptide of 7-peptide mix in cohort of 39

FIG. 32

| Peptide # | Core | Pool 1 | Pool 2 | Pool 3 | Pool 4 | Pool 5 | Pool 7a | Pool 7b | Diluent |
|---|---|---|---|---|---|---|---|---|---|
| 1 | 23+24 | X | | X | | | x | x | 2% acid |
| 2 | 40 | X | | X | | | x | x | PBS |
| 3 | 46+47 | X | | X | X | | | | PBS |
| 4 | 49 | X | | X | X | | x | x | PBS |
| 5 | 50 | X | | X | X | | | | 1% acid |
| 6 | 51 | X | | X | | | | | 10% acid |
| 7 | 57 | X | | X | | | | | 0.1M |
| 8 | A+B | | X | X | | | | | PBS |
| 9 | C+D | | X | X | | | | | 0.1M |
| 10 | E | | X | X | | X | x | | PBS |
| 11 | 23 | | | | X | | | | PBS |
| 12 | 24 | | | | X | | | | PBS |
| 13 | 40 short | | | | X | | | | PBS |
| 14 | 46 | | | | | | | | PBS |
| 15 | 47 | | | | | | x | x | PBS |
| 16 | 50/51 | | | | | | | | 10% acid |
| 17 | 51a | | | | | | | | 10% acid |
| 18 | 51b | | | | X | | | | PBS |
| 19 | 57 short | | | | X | | x | x | 1% acid |
| 20 | A | | | | | X | | | PBS |
| 21 | B | | | | | X | x | x | PBS |
| 22 | C | | | | | X | | | 0.1M |
| 23 | D | | | | | X | x | x | 0.1M |

IMMUNOTHERAPEUTIC COMPOSITION AND USES THEREOF

CROSS-REFERENCES TO RELATED APPLICATIONS

This application is a national stage entry, filed under 35 U.S.C. § 371, of International Application No. PCT/AU2014/050249, filed on Sep. 25, 2014, and claims the benefit of and priority to Australian Application No. 2013903686, filed Sep. 25, 2013, the entire contents of each of which are hereby incorporated herein by reference in their entireties and for all purposes.

INCORPORATION-BY-REFERENCE OF SEQUENCE LISTING

The contents of the text file named "Corrected_Sequence_Listing_28616502N01US_121520.TXT", which was created on Dec. 15, 2020, and is 33,904 bytes in size, is hereby incorporated by reference in its entirety and for all purposes.

FIELD OF THE INVENTION

The present invention relates generally to an immunotherapeutic composition. More particularly, the present invention relates to an immunotherapeutic composition which interacts immunologically with T lymphocytes in subjects having peanut allergy or allergy to other tree nuts. This composition is preferably immunointeractive with T cells in subjects having an allergy to the Ara h 1 and/or Ara h 2 allergens. The composition of the present invention is useful in the therapeutic or prophylactic treatment of conditions characterised by an aberrant, inappropriate or otherwise unwanted immune response to peanut, Ara h1 and/or Ara h 2 or derivative or homologue thereof.

BACKGROUND OF THE INVENTION

Bibliographic details of the publications referred to by author in this specification are collected alphabetically at the end of the description.

The reference to any prior art in this specification is not, and should not be taken as, an acknowledgment or any form of suggestion that that prior art forms part of the common general knowledge.

Peanut allergy is a life-threatening and incurable disorder, affecting approximately 1% of the general population (Husain et al. *J Am Acad Dermatol.* 66(1):136-43, 2012, Burks, *Lancet.* 371(9623):1538-46, 2008). It is characterised by the sudden onset of anaphylaxis, which may occur with exposure to minute quantities of peanut proteins (Hourihane et al., *J Allergy Clin Immunol* 100: 596-600, 1997; Pumphrey, *Current Opinion in Allergy & Immunology.* 4(4):285-90, 2004). Peanut induced anaphylaxis is that most frequently associated with mortality or with life-threatening features (Bock et al. *J Allergy Clin Immunol.* 119(4):1016-8, 2007; Burks 2008, supra). Peanut proteins are frequently concealed within apparently safe food sources, such that accidental contact occurs for up to 50% of sufferers over a 5 year period (Sicherer et al., *Paediatrics* 102: e6, 1998). Not surprisingly, peanut and tree nut allergy is associated with significant psychological morbidity for sufferers and carers alike, akin to that suffered by those with chronic debilitating illnesses such as rheumatoid arthritis (Primeau et al., *Clin Exp Allergy* 30: 1135-43, 2000; Kemp et al. *Med. J. Aust.* 188(9):503-4, 2008). Cure, while being an imperative to remove peanut and tree nut allergy as a cause of mortality, is also necessary to remove the chronic psychological burden that peanut allergic subjects carry.

To date, efforts at immunotherapy for peanut allergy have been met by extremely limited success. Nelson et al. have shown that clinical desensitisation of peanut can be induced using a rush immunotherapy protocol with an unfractionated peanut extract, but that clinical desensitisation is lost in approximately half of the subjects during maintenance dosing and additionally that injections are associated with frequent episodes of anaphylaxis in the majority of subjects during both the buildup and maintenance phases (Nelson et al., *J Allergy Clin Immunol* 99: 744-51, 1997). Oppenheimer et al. demonstrated similar findings within their study, again showing that active therapy with unfractionated peanut extract is associated with a high rate of systemic anaphylaxis. Data collection in that study was terminated after the administration of peanut extract to a placebo randomised subject resulted in their death, highlighting the dangerous nature of this condition (Oppenheimer et al., *J Allergy Clin Immunol* 90: 256-62, 1992). Recent studies of oral immunotherapy with whole peanut flour provide encouragement that desensitization is feasible, but the observed adverse reactions highlight major safety concerns (Hofmann et al. *J. Allergy Clin. Immunol.* 124, 286, 2009; Jones et al. *J. Allergy Clin. Immunol.* 24, 292, 2009; Clark et al. *Allergy* 64, 1218, 2009; Varshney et al. *J Allergy Clin Immunol.* 127(3):654-60, 2011; Varshney et al. *J Allergy Clin Immunol.* 124(6): 1351-2, 2009; Anagnostou et al. *Clin Exp Allergy.* 41(9): 1273-81, 2011; Allen & O'Hehir. *Clin Exp Allergy.* 41(9): 1172-4, 2011; Yu et al. *Int Arch Allergy Immunol.* 159(2): 179-182, 2012; Thyagarajan et al. *J Allergy Clin Immunol.* 126(1):31-2, 2010; Blumchen et al. *J Allergy Clin Immunol.* 126(1):83-91, 2010). Even with the exclusion of children prone to severe symptoms or asthma, two studies reported an anaphylactic episode, in one case during an initial food challenge (Clark et al. *Allergy* 64, 1218, 2009) and in the other during treatment of a child who had not previously experienced anaphylaxis (Hofmann et al. *J. Allergy Clin. Immunol.* 124, 286, 2009).

Development of novel strategies to overcome the morbidity associated with allergen immunotherapy depends on an accurate understanding of the immunological basis to successful immunotherapy, as well as its side-effects. It has long been established that morbidity due to allergen immunotherapy is due to the cross-linking of IgE, and that this action is not required for such therapy to be efficacious (Litwin et al., *Int Arch Allergy Appl Immunol* 87: 361-61, 998). It is also known that one of the critical actions of conventional (subcutaneous injection or sublingual or oral with unfractionated allergen extract) immunotherapy in producing tolerance is its ability to change the predominant specific T cell phenotype from a $T_H2$ to a regulatory phenotype. These regulatory T cells act via production of the anti-inflammatory cytokines IL-10 and/or TGFβ. (Akdis & Akdis, *J Allergy Clin Immunol.* 123:735-46, 2009; Akdis & Akdis, *Nature Reviews: Drug Discovery.* 8:645-60. 2009; Akdis & Akdis, *J Allergy Clin Immunol.* 127:18-27, 2011).

A key difference in antibody and lymphocyte responses is in antigen recognition, antibodies recognising conformational B cell epitopes dependent on molecular tertiary structure, while CD4+ T cells recognise short linear peptides. This difference in antigen recognition is the basis to many novel strategies of immunotherapy, including that using peptides based upon T cell epitopes, B cell epitope mutants and altered peptide ligands (Rolland et al. *Pharmacology &*

*Therapeutics* 121:273-284, 2009). Such methods all depend on the alteration or absence of molecular tertiary structure, so that IgE cross-linking and effector cell activation is lost. Peptide immunotherapy is a method in respect of which evidence of efficacy exists, being documented for both cat dander allergy and bee venom allergy. Three different studies showed that, in the absence of any systemic side-effects, clinical and immunological tolerance could be achieved for the major bee venom allergen Phospholipase A2 (PLA2) using T cell epitope-containing sequences (Muller et al. *J Allergy Clin Immunol.* 101: 747-54, 1998; Tarzi et al. *Clin Exp Allergy.* 36: 465-74, 2006; Fellrath et al. *J Allergy Clin Immunol.* 111: 854-61, 2003), while several studies have demonstrated that peptides based on the structure of the major cat allergen Fel d 1 can be used to induce diminished clinical responses (Norman et al., *Am J Respir Crit Care Med* 154: 1623-8, 1996; Marcotte et al., *J Allergy Clin Immunol* 101: 506-13, 1998; Pene et al., *J Allergy Clin Immunol* 102: 571-8, 1998; Oldfield et al. *Lancet* 360:47-53, 2002; Alexander et al. *Clin Exp Allergy* 35: 52-8, 2004; Alexander et al. *Allergy* 60:1269-74, 2005). Most recently, a phase IIa trial confirmed the safety, tolerability and potential efficacy of a seven-peptide mixture from Fel d 1 (Toleromune Cat©, Cicassia Ltd., Oxford, UK) (Worm et al. *J Allergy Clin Immunol.* 127: 89-97, 2011) with Phase IIb trials now underway (Moldaver & Larche. *Allergy.* 66: 784-91, 2011; Worm et al. *Expert Opin. Investig. Drugs.* 22(10): 1347-1357, 2013). Crucial to the development of such strategies is the retention of T cell epitopes, so that T cell phenotypic change can be induced.

The ability to bind directly on to MHC class II molecules allows peptides to be presented by non-professional or immature APC without pro-inflammatory and co-stimulatory signals which promotes induction of tolerance, anergy and/or suppressive activity in responding T cells (Moldaver & Larche, *Allergy* 66: 784-91, 2011) and/or other $CD4^+$ T cells that express MHC class II. This also allows peptides to be presented at higher frequency than peptides processed from the whole molecule (Santambrogio et al. *Proc Natl Acad Sci USA,* 1999, 96:15056-61), and since they are also safer than whole allergen, peptides can be given at higher concentrations, thus repolarising T cell responses more effectively.

Importantly, targeting T cells specific for dominant T cell epitopes of major allergens can alter responses to whole allergen extracts (linked suppression). Many studies reporting successful peptide immunotherapy in murine models of allergy demonstrated that administration of dominant T-cell epitope peptides of major allergens induced tolerance not only to those peptides, but also to purified allergen and whole allergen extracts (Yang et al. *Clin Exp Allergy* 40(4): 668-78, 2010; Yoshitomi et al. *J Pept Sci.* 13(8):499-503, 2007; Marazuela et al. *Mol Immunol.* 45(2):438-45, 2008; Rupa et al. *Allergy.* 67(1):74-82, 2012; Hoyne et al. *J Exp Med.* 178(5):1783-8, 1993; Hall et al. *Vaccine.* 21(5-6):549-61, 2003).

Accordingly, there is a need to both identify the major peanut allergens and, further, to identify the T cell epitopes of these allergens. The identification, characterisation, and analysis of these T cell epitopes is critical to the development of specific immunotherapeutic or prophylactic methodology. To this end, although the Ara h 1 and/or Ara h 2 peanut allergen molecules have previously been the subject of analysis, the identification of the T cell core epitopic regions is essential to the development of an effective vaccine.

In work leading up to the present invention, dominant, HLA-degenerate Ara h 1 and/or Ara h 2 core T cell epitopic regions have been identified. This group of core T cell epitopic regions is unique in terms of its high level of efficacy. Unlike the previously studied 20mer Ara h 1 and/or Ara h 2 peptides which were identified based only on their ability to exhibit some level of T cell reactivity, there have been identified a selected set of core T cell epitope regions which are both immunodominant, relative to other Ara h 1 and/or Ara h 2 peptide fragments, and are also HLA degenerate in that they bind to two or more HLA types. Still further, many of these T cell epitopic core regions are presented by HLA-DQ molecules. HLA-DQ molecules are more conserved in mixed populations than HLA-DR molecules. Accordingly, peptides presented on HLA-DQ enable broader population coverage.

In a still further finding, it has also been determined that a specific subgroup of seven of these peptides which contain both Ara h 1 and Ara h 2 T cell epitopes provides particularly effective immunological outcomes. Accordingly, the identification of this uniquely effective group of peptides has facilitated the development of particularly effective therapeutic prophylactic methods for the treatment of conditions characterised by aberrant, inappropriate or otherwise unwanted immune responses to Ara h 1 and/or Ara h 2 or derivative or homologue thereof, other tree nut allergies or allergens to a composition, such as foods, containing the Ara h 1 and/or Ara h 2 molecules.

SUMMARY OF THE INVENTION

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source. Further, as used herein the singular forms of "a", "and" and "the" include plural referents unless the context clearly dictates otherwise.

Unless otherwise defined, all technical and scientific terms used herein have the same meaning as commonly understood by one of ordinary skill in the art to which this invention belongs.

The subject specification contains amino acid sequence information prepared using the programme PatentIn Version 3.5, presented herein after the bibliography. Each amino acid sequence is identified in the sequence listing by the numeric indicator <210> followed by the sequence identifier (eg. <210>1, <210>2, etc). The length, type of sequence (protein, etc) and source organism for each sequence is indicated by information provided in the numeric indicator fields <211>, <212> and <213>, respectively. Amino acid sequences referred to in the specification are identified by the indicator SEQ ID NO: followed by the sequence identifier (eg. SEQ ID NO:1, SEQ ID NO:2, etc.). The sequence identifier referred to in the specification correlates to the information provided in numeric indicator field <400> in the sequence listing, which is followed by the sequence identifier (eg. <400>1, <400>2, etc). That is SEQ ID NO:1 as detailed in the specification correlates to the sequence indicated as <400>1 in the sequence listing.

One aspect of the present invention is directed to an immunomodulatory composition comprising at least five of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPXEQHLM (SEQ ID NO: 7)

(viii) ENNQRXMXEA (SEQ ID NO: 8)

or functional derivatives or homologues thereof wherein residue X is cysteine or serine and said composition comprises at least one T cell epitope region selected from SEQ ID NOS: 1-6 and at least one T cell epitope region selected from SEQ ID NOS: 7-8.

In another aspect, said LRPXEQHLM is LRPSEQHLM (SEQ ID NO;137).

In still another aspect, said ENNQRXMXEA is ENNQRSMSEA (SEQ ID NO:103).

In accordance with these aspects and embodiments of the present invention, said composition comprises at least 6 of said T cell epitopic regions.

In a further aspect, said composition comprises at least 7 of said T cell epitopic regions.

In still a further aspect, said composition comprises each of said 8 T cell epitopic regions.

In another aspect there is provided an immunomodulatory composition comprising each of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPXEQHLM (SEQ ID NO: 7)

(viii) ENNQRXMXEA (SEQ ID NO: 8)

or functional derivatives or homologues thereof wherein said residue X is cysteine or serine.

In yet another aspect there is provided an immunomodulatory composition comprising each of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPSEQHLM (SEQ ID NO: 102)

(viii) ENNQRSMSEA (SEQ ID NO: 103)

or functional derivatives or homologues thereof.

In a related aspect the present invention is directed to an immunomodulatory composition comprising one or more peptides, each of which peptides is up to 60 contiguous amino acids in length and which peptides include each of the Ara h 1 and Ara h 2 T cell epitope region combinations detailed hereinbefore.

In a further aspect the present invention is directed to an immunomodulatory composition comprising one or more peptides, each of which peptides is up to 60 contiguous amino acids in length and which peptides include each of the Ara h 1 and Ara h 2 T cell epitopic regions from the list consisting of:

(i) FQNLQNHR (SEQ ID NO: 1)

(ii) IVQIEA (SEQ ID NO: 2)

-continued (iii)
NEGVIVKVSK (SEQ ID NO: 3)

(iv)
EVKPDKKNPQLQ (SEQ ID NO: 4)

(v)
EGALML (SEQ ID NO: 5)

(vi)
IMPAAHP (SEQ ID NO: 6)

(vii)
LRPSEQHLM (SEQ ID NO: 7)

(viii)
ENNQRSMSEA (SEQ ID NO: 8)

or functional derivatives or homologues thereof.

In yet another aspect said peptides or T cell epitopic regions are capable of modifying T cell function when presented to T cells isolated from subjects having a condition characterised by an aberrant, unwanted or otherwise inappropriate immune response to Ara h 1 and/or Ara h 2 or to an allergen present in a composition, such as food, comprising Ara h 1 and/or Ara h 2 but which peptides are unable to bind to Ara h 1-specific and/or Ara h 2-specific IgE.

In accordance with these aspects, said peptides are selected from the list consisting of:

(i)
FQNLQNHRIVQIEAKPNTLV (SEQ ID NO: 11)

(ii)
STRSSENNEGVIVKVSKE (SEQ ID NO: 12)

(iii)
EVKPDKKNPQLQ (SEQ ID NO: 4)

(iv)
VEIKEGALMLPHFNSKA (SEQ ID NO: 13)

(v)
VFIMPAAHPVAINASS (SEQ ID NO: 14)

(vi)
ANLRPXEQHLM (SEQ ID NO: 15)

(vii)
EFENNQRXIMEALQ (SEQ ID NO: 16)

(viii)
NNFGKLFEVKPDKKNPQLQ (SEQ ID NO: 17)

(ix)
GDVFIMPAAHPVAINASSE (SEQ ID NO: 18)

(x)
SQLERANLRPXEQHLM (SEQ ID NO: 19)

-continued (xi)
ELNEFENNQRXMXEALQ (SEQ ID NO: 20)

(xii)
FQNLQNHRIV (SEQ ID NO: 21)

(xiii)
RIVQIEAKPNTLV (SEQ ID NO: 22)

(xiv)
ENNEGVIVKVSKE (SEQ ID NO: 23)

(xv)
EVKPDKKNPQLQD (SEQ ID NO: 24)

(xvi)
EFENNQRXMXEALQQI (SEQ ID NO: 25)

(xvii)
NNFGKLFEVKPDKKNPQLQD (SEQ ID NO: 26)

(xviii)
ELNEFENNQRXMXEALQQI (SEQ ID NO: 27)

(xx)
WSTRSSENNEGVIVKVSKE (SEQ ID NO: 28)

(xxi)
GDVFIMPAAHPVAINASS (SEQ ID NO: 29)

or functional derivatives or homologues thereof wherein residue X is cysteine or serine.

In one embodiment, said residue X is serine.

In a further asepct said peptides are selected from:

(i)
FQNLQNHRIVQIEAKPNTLV (SEQ ID NO: 11)

(ii)
STRSSENNEGVIVKVSKE (SEQ ID NO: 12)

(iii)
EVKPDKKNPQLQ (SEQ ID NO: 4)

(iv)
VEIKEGALMLPHFNSKA (SEQ ID NO: 13)

(v)
VFIMPAAHPVAINASS (SEQ ID NO: 14)

(vi)
ANLRPSEQHLM (SEQ ID NO: 31)

(vii)
EFENNQRSMSEALQ (SEQ ID NO: 32)

(viii)
EVKPDKKNPQLQD (SEQ ID NO: 24)

-continued (ix)
                                              (SEQ ID NO: 32)
EFENNQRSMSEALQQI or functional derivatives or homologues thereof.

In another aspect, said immunomodulatory composition comprises each of the Ara h 1 and Ara h 2 T cell peptides from the list consisting of:

(i)
                                              (SEQ ID NO: 11)
FQNLQNHRIVQIEAKPNTLV;

(ii)
                                              (SEQ ID NO: 12)
STRSSENNEGVIVKVSKE;

(iii)
                                              (SEQ ID NO: 33)
EVKPDKKNPQLQ
and/or
                                              (SEQ ID NO: 24)
EVKPDKKNPQLQD;

(iv)
                                              (SEQ ID NO: 13)
VEIKEGALMLPHFNSKA;

(v)
                                              (SEQ ID NO: 14)
VFIMPAAHPVAINASS;

(vi)
                                              (SEQ ID NO: 30)
ANLRPSEQHLM;
and (vii)
                                              (SEQ ID NO: 31)
EFENNQRSMSEALQ
and/or
                                              (SEQ ID NO: 32)
EFENNQRSMSEALQQI.

or functional derivatives or homologues thereof.

In a yet a further aspect, the inventors have designed a preferred set of seven peptides, five of which comprise Ara h 1 T cell epitopes and two of which comprise Ara h 2 T cell epitopes, which function particularly efficaciously, when administered together, to induce desensitisation or tolerance and thereby either prophylactically or therapeutically treat hypersensitivity to compositions, such as foods, comprising Ara h 1 and/or Ara h 2. These peptides are:

(i)
                                              (SEQ ID NO: 11)
FQNLQNHRIVQIEAKPNTLV (ii)
                                              (SEQ ID NO: 12)
STRSSENNEGVIVKVSKE (iii)
                                              (SEQ ID NO: 4)
EVKPDKKNPQLQ
and/or
                                              (SEQ ID NO: 24)
EVKPDKKNPQLQD (iv)
                                              (SEQ ID NO: 13)
VEIKEGALMLPHFNSKA (v)
                                              (SEQ ID NO: 14)
VFIMPAAHPVAINASS (vi)
                                              (SEQ NO: 30)
ANLRPSEQHLM (vii)
                                              (SEQ NO: 31)
EFENNQRSMSEALQ
and/or
                                              (SEQ ID NO: 32)
EFENNQRSMSEALQQI In still yet another aspect there is provided an immunomodulatory composition comprising each of the Ara h 1 and Ara h 2 T cell peptides from the list consisting of:

(i)
                                              (SEQ ID NO: 11)
FQNLQNHRIVQIEAKPNTLV (ii)
                                              (SEQ ID NO: 12)
STRSSENNEGVIVKVSKE (iii)
                                              (SEQ ID NO: 4)
EVKPDKKNPQLQ
and/or
                                              (SEQ ID NO: 24)
EVKPDKKNPQLQD (iv)
                                              (SEQ ID NO: 13)
VEIKEGALMLPHFNSKA (v)
                                              (SEQ ID NO: 14)
VFIMPAAHPVAINASS (vi)
                                              (SEQ NO: 30)
ANLRPSEQHLM (vii)
                                              (SEQ NO: 31)
EFENNQRSMSEALQ
and/or
                                              (SEQ ID NO: 32)
EFENNQRSMSEALQQI In a yet still another aspect, there is provided a composition comprising each of the Ara h 1 and Ara h 2 T cell peptides from the list consisting of:

(i)
                                              (SEQ ID NO: 11)
FQNLQNHRIVQIEAKPNTLV (ii)
                                              (SEQ ID NO: 12)
STRSSENNEGVIVKVSKE (iii)
                                              (SEQ ID NO: 4)
EVKPDKKNPQLQ
and/or
                                              (SEQ ID NO: 24)
EVKPDKKNPQLD (iv)
                                              (SEQ ID NO: 13)
VEIKEGALMLPHFNSKA (v)
VFIMPAAHPVAINASS (SEQ ID NO: 14)

(vi)
ANLRPSEQHLM (SEQ NO: 30)

(vii)
EFENNQRSMSEALQ (SEQ NO: 31)
and/or
EFENNQRSMSEALQQI (SEQ ID NO: 32)

which peptides are capable of reducing Ara h 1 and/or Ara h 2 hypersensitivity or hypersensitivity to a composition comprising Ara h 1 and/or Ara h 2 when administered to a subject having a condition characterised by said hypersensitivity.

The present invention is directed to a composition comprising the peptides hereinbefore defined. It should be understood, though, that the subject composition may comprise additional components, such as additional peptides. Examples of other peptides which may be included in the composition include, but are not limited to:

(i)
ALMLPHFNSKAMVIVVV (SEQ ID NO: 33)

(ii)
NNFGKLFEVKPDKKNPQ (SEQ ID NO: 34)

(iii)
SQLERANLRPXEQ (SEQ ID NO: 35)

(iv)
ELNEFENNQRXM (SEQ ID NO: 36)

(v)
NNFGKLFEVKPDKKNPQLQD (SEQ ID NO: 37)

(vi)
NNFGKLFEVKPDKKNPQL (SEQ ID NO: 38)

(vii)
SQLERANLRPXEQH (SEQ ID NO: 39)

(viii)
KAMVIVVVNKGTGNLELVAV (SEQ ID NO: 40)

(ix)
RELRNLPQQXGLRA (SEQ ID NO: 41)

(x)
KAMVIVVVNKG (SEQ ID NO: 42)

(xi)
AMVIVVVNKGTGNLELV (SEQ ID NO: 43)

(xii)
VVNKGTGNLELVAVRK (SEQ ID NO: 44)

or functional derivatives or homologues thereof wherein residue X is cysteine or serine.

In another aspect, the present invention provides a nucleic acid molecule composition comprising one or more nucleic acid molecules encoding or complementary to a sequence encoding the T cell epitopes and peptides as hereinbefore defined or a derivative, homologue or analogue thereof.

In still another aspect the present invention provides a method for the treatment and/or prophylaxis of a condition in a subject, which condition is characterised by the aberrant, unwanted or otherwise inappropriate immune response to Ara h 1 and/or Ara h 2 or an allergen in a composition comprising Ara h 1 and/or Ara h 2, said method comprising administering to said subject an effective amount of an immunomodulatory composition as hereinbefore defined for a time and under conditions sufficient to remove or reduce the presence or function in said subject of T cells directed to said Ara h 1 and/or Ara h 2 or other allergen.

In a further aspect said condition is hypersensitivity to peanuts or tree nuts which contain Ara h 1 and Ara h 2 or Ara h 1-like or Ara h 2-like molecules, such as hazelnuts, almonds or Brazil nuts.

In another aspect, said method desensitises or induces immunological tolerance to Ara h 1 and/or Ara h 2 or other allergen of said composition.

In still another aspect, said desensitization or tolerance is achieved by inducing T cell anergy or apoptosis.

In yet still another aspect, said desensitisation or tolerance is achieved by inducing Ara h 1 or Ara h 2-specific Treg cells.

A further aspect of the present invention contemplates the use of an immunomodulatory composition as hereinbefore defined in the manufacture of a medicament for the treatment of a condition in a mammal, which condition is characterised by an aberrant, unwanted or otherwise inappropriate immune response to Ara h 1 and/or Ara h 2.

Preferably said condition is hypersensitivity to peanuts or a tree nut which contains Ara h 1 and/or Ara h 2 or Ara h 1-like and/or Ara h 2-like molecules, such as a hazelnut.

In yet another further aspect, the present invention contemplates a vaccine comprising the composition as hereinbefore defined together with one or more pharmaceutically acceptable carriers and/or diluents. Said composition is referred to as the active ingredient.

Yet another aspect of the present invention relates to the compositions, as hereinbefore defined, when used in the method of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) CFSE-labelled PBMC from a peanut-allergic subject incubated with whole peanut extract or the Vax (7 peptide compilation). Boxes show percent of activated proliferating CD4+ T cells (CD25+CFSElo). SI indicates fold increase in T cell activation above no antigen control. (FIG. 1B) Confirmation of peanut-allergic donor PBMC CD4+ T-cell activation and proliferation in response to the Vax (7 peptide compilation) in 7 subjects (all have a positive SI>2.5).

(FIG. 2B) BAT data and (FIG. 2C) Histamine release data (measured by commercial kit) from a peanut-allergic subject following incubation with increasing concentrations (µg/ml) of whole peanut extract or the Vax. Positive controls are anti-IgE and fMLP. Whole peanut extract causes high basophil activation and histamine release but the Vax does not. Data are representative of 14 peanut-allergic subjects tested.

FIG. 12 is a graphical representation of PBMC responses to peptide pools vs whole peanut. Peptides included in each pool are shown in FIG. 32. P-values show Wilcoxon matched pairs signed rank test (for non-parametric data).

FIG. 13 is a graphical representation of PBMC responses to peptide pools vs whole peanut. Peptides included in each pool are shown in FIG. 32. P-values show Wilcoxon matched pairs signed rank test (for non-parametric data).

FIG. 14 is a graphical representation comprising PBMC T cell responses to the preferred 7-peptide pool. Stats: Kruskal-Wallis test for non-parametric data with Dunns post-hoc corrections to test for differences between multiple groups. *data normalised to % of response to whole peanut due to variation in magnitudes of responses in different subjects in the different cohorts analysed for the different pools.

FIG. 17 is a table showing therapeutic candidate peptides of Ara h 1 and Ara h 2.

FIG. 19 is a table showing the SIs of peptide-induce proliferation for 24 subjects. Upper panel shows new peanut-allergic donor cohort (distinct to cohort used for TCL). Lower panel shows 4 subjects from cohort used for TCL generation with combined totals from upper and lower panels. CPE, crude peanut extract; +ve, positive; nt, not tested (peptide stocks not available at time of testing); Grey, stimulation indices ≥1.1<2.5; Black, stimulation indices ≥2.5.

FIG. 20 is a table showing the proliferative responses (thymidine uptake) of TCL to Ara h 2 20-mer peptides. Table shows SI values (=fold increase in TCL proliferation with peptide above proliferation in unstimulated TCL). Only positive stimulation indices (≥2.5) are shown: Grey, ≥2.5≤5.0; Black, >5.0. A) allergen-driven TCL; B) peptide-driven TCL.

FIG. 21 is a table showing core T cell epitopes found in dominant Ara h 1 20-mers.

FIG. 22 is a table showing core T cell epitopes found in dominant Ara h 2 20-mers.

FIG. 23 is a table showing HLA restriction of Ara h 1 and Ara h 2 T cell epitope presentation. Grey shading indicates T cell epitopes included in current 7-peptide mix.

FIG. 24 is a table showing HLA-restriction of Ara h 2 epitope presentation.

FIG. 25 is a table showing a results summary for an HLA-DR prediction algorithm for binding motifs within dominant Ara h 1 20-mers.

FIG. 26 is a table showing HLA-DRB alleles; wherein the shading indicates particularly frequent alleles in Caucasian populations.

FIG. 27 is a table showing the combining overlapping Ara h 1 T cell epitopes into single peptides≤20 aa long. Grey shading indicates overlapping consolidated T cell epitope pairs combined into single peptides for further analyses as outlined in the text. * Asterisks and boxes indicate the seven Ara h 1 candidate peptides proposed for a therapeutic.

FIG. 28 is a table showing a panel of 23 candidate peptides.

Figure 30:
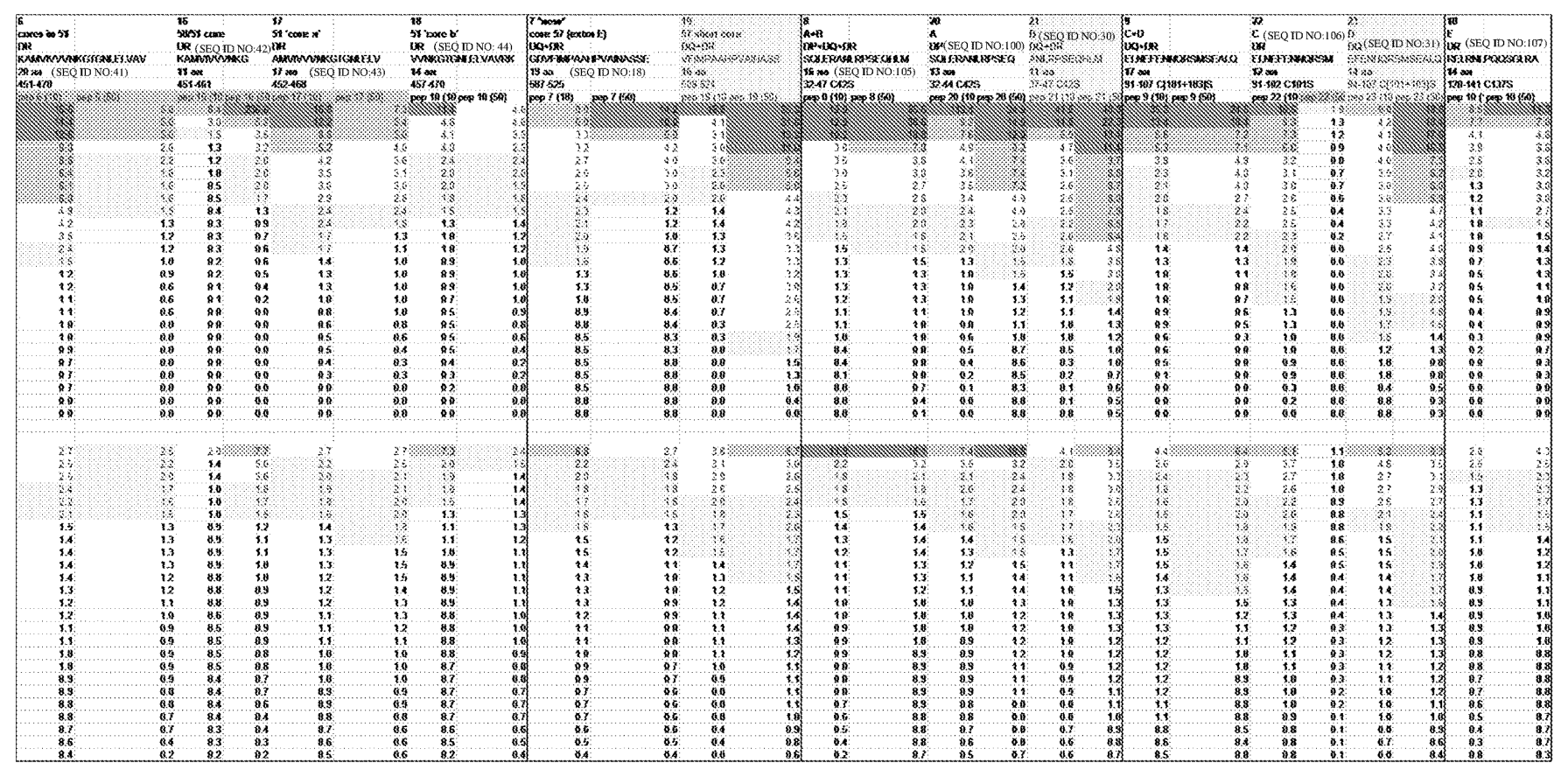

FIG. 30 is a table showing an alternate summary of PBMC T cell responses to full set of candidate peptides in 25 peanut-allergic subjects.

FIG. 31 is a table showing a summary of responses to each peptide of 7-peptide mix in cohort of 39.

FIG. 32 is a table showing PBMC T cell responses were compared to whole peanut and peptide pools 1-5.

DETAILED DESCRIPTION OF THE INVENTION

Figure 1A:
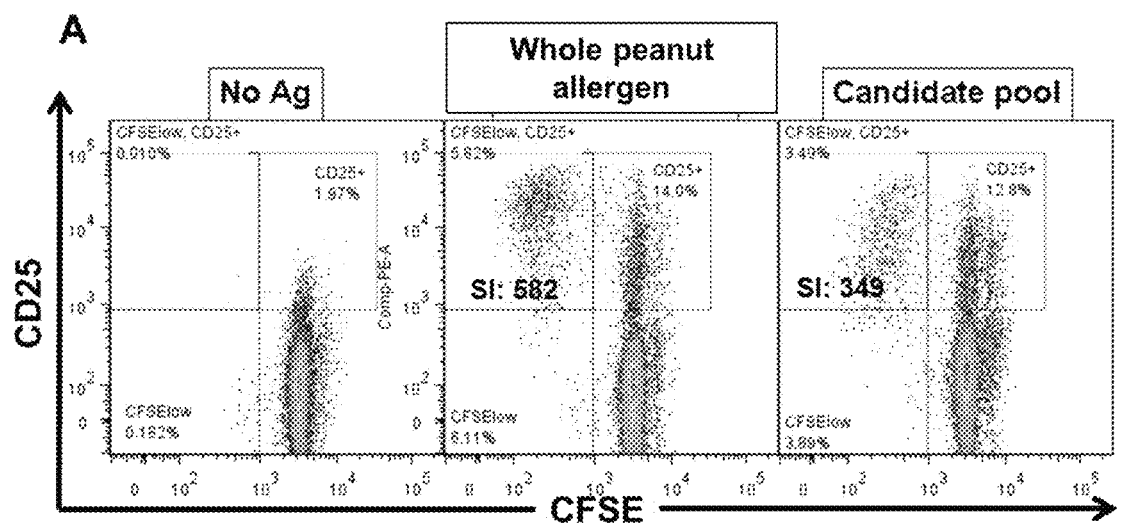
FIGS. 1A and 1B are graphical representations of a CFSE screen for peptide-specific PBMC T cells.

The present invention is predicated, in part, on the identification of a group of Ara h 1 and Ara h 2 epitopes which, when administered together, in a group of at least five, produce more efficacious immunological outcomes than any of these epitopes used either alone or together with other combinations of these or other Ara h 1 or Ara h 2 peptides. In particular, it has been determined that the use of all eight epitopes produces particularly and exceptionally efficacious functional outcomes, most particularly when these eight epitopes are administered in the context of the seven peptides exemplified herein. The design of this composition has enabled the development of significantly more efficacious therapeutic and prophylactic compositions and treatment approaches, than have been available to date, for conditions such as, but not limited to, peanut allergy.

Accordingly, one aspect of the present invention is directed to an immunomodulatory composition comprising at least five of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPXEQHLM (SEQ ID NO: 7)

(viii) ENNQRXMXEA (SEQ ID NO: 8)

or functional derivatives or homologues thereof wherein residue X is cysteine or serine and said composition comprises at least one T cell epitopic region selected from SEQ ID NOS: 1-6 and at least one T cell epitopic region selected from SEQ ID NOS: 7-8.

In one embodiment, said LRPXEQHLM is LRPSEQHLM (SEQ ID NO;137).

In another embodiment, said ENNQRXMXEA is ENNQRSMSEA (SEQ ID NO:103).

In accordance with these aspects and embodiments of the present invention, said composition comprises at least 6 of said T cell epitopic regions.

In a further embodiment, said composition comprises at least 7 of said T cell epitopic regions.

In still a further embodiment, said composition comprises each of said 8 T cell epitopic regions.

According to this embodiment there is therefore provided an immunomodulatory composition comprising each of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPXEQHLM (SEQ ID NO: 7)

(viii) ENNQRXMXEA (SEQ ID NO: 8)

or functional derivatives or homologues thereof wherein said residue X is cysteine or serine.

In another embodiment there is provided an immunomodulatory composition comprising each of the Ara h 1 and Ara h 2 T cell epitopic regions from the list consisting of:

(i) FQNLQNHR (SEQ ID NO: 1)

(ii) IVQIEA (SEQ ID NO: 2)

(iii) NEGVIVKVSK (SEQ ID NO: 3)

(iv) EVKPDKKNPQLQ (SEQ ID NO: 4)

(v) EGALML (SEQ ID NO: 5)

(vi) IMPAAHP (SEQ ID NO: 6)

(vii) LRPSEQHLM (SEQ ID NO: 102)

(viii) ENNQRSMSEA (SEQ ID NO: 103)

or functional derivatives or homologues thereof.

In a related aspect the present invention is directed to an immunomodulatory composition comprising one or more peptides, each of which peptides is up to 60 contiguous amino acids in length and which peptides include each of the Ara h 1 and Ara h 2 T cell epitopic region combinations detailed hereinbefore.

In accordance with this aspect the present invention is directed to an immunomodulatory composition comprising one or more peptides, each of which peptides is up to 60 contiguous amino acids in length and which peptides include each of the Ara h 1 and Ara h 2 T cell epitopic regions from the list consisting of:

(i)
FQNLQNHR (SEQ ID NO: 1)

(ii)
IVQIEA (SEQ ID NO: 2)

(iii)
NEGVIVKVSK (SEQ ID NO: 3)

(iv)
EVKPDKKNPQLQ (SEQ ID NO: 4)

(v)
EGALML (SEQ ID NO: 5)

(vi)
IMPAAHP (SEQ ID NO: 6)

(vii)
LRPSEQHLM (SEQ ID NO: 7)

(viii)
ENNQRSMSEA (SEQ ID NO: 8)

or functional derivatives or homologues thereof.

In another embodiment of the preceding aspects of the invention, said peptides or T cell epitopic regions are capable of modifying T cell function when presented to T cells isolated from subjects having a condition characterised by an aberrant, unwanted or otherwise inappropriate immune response to Ara h 1 and/or Ara h 2 or to an allergen present in a composition, such as food, comprising Ara h 1 and/or Ara h 2 but which peptides are unable to bind to Ara h 1-specific and/or Ara h 2-specific IgE.

Without limiting the present invention in any way, peanuts contain many proteins, with the number of distinct bands visible on SDS-PAGE depending on the methodology used. Up to 53 bands are visible following high pressure liquid chromatography (de Jong et al., *Clin Exp Allergy* 28: 743-51, 1998). Only two of these proteins warrant classification as major allergens using standard criteria, whereby IgE reactivity occurs within greater than 50% of the peanut allergic population; these proteins are termed Ara h 1 and Ara h 2 (Burks et al., *Allergy* 53: 725-30, 1998). Although a number of studies have indicated Ara h 2 to be the more potent of these two allergens (Blanc et al. *Clin Exp Allergy.* 2009; 39(8):1277-85; Koppelman et al. *Clin Exp Allergy.* 2004; 34(4):583-90; Palmer et al. *Clin Immunol.* 2005; 115(3):302-12), Ara h 1 also plays a major role in the pathogenesis of peanut allergy, with numerous studies reporting strong correlations between symptom severity and IgE reactivity to both Ara h 1 and Ara h 2 (Glaumann et al. *Allergy.* 2012; 67(2):242-7; Chiang et al. *Pediatr Allergy Immunol.* 2009; 21(2 Pt 2):e429-38; Asarnoj et al. *Allergy.* 2010, 65(9):1189-95; Moverare et al. *Int Arch Allergy Immunol* 2011; 156(3):282-90; Lin et al. *J Microbiol Immunol Infect.* 2012; Peeters et al. *Clin Exp Allergy.* 2007; 37(1): 108-15). Ara h 1 is the most abundant major allergen in peanut, accounting for 12-16% of total peanut protein (Koppelman et al. *Allergy.* 2001; 56(2):132-7).

Still without limiting the present invention in any way, the Ara h 1 allergen is a 7S seed storage glycoprotein or vicilin. The concentration of Ara h 1 in peanuts increases with the size of the kernel (4-16 mg extracted Ara h 1/g peanut), so expression of the protein is associated with peanut maturity (Pomés et al. 2006, *Clin. Exp. Allergy* 36(6):824-30). Ara h 1 is a homotrimer held together through hydrophobic areas at the distal ends of the monomers, where most of the IgE binding B cell epitopes are located. Each 64.5 kD monomer has a cupin motif which consists of two core β-barrels, each associated to a loop domain of α-helices.

Ara h 2 is a glycoprotein which has been identified as a member of the conglutin seed storage family. 20% of the Ara h 2 molecular mass represents carbohydrate side chains and it migrates as a doublet on SDS-PAGE with an average molecular mass of 17.5 kDa (Burks et al, *Int Arch Allergy Immunol* 119:165-172, 1992). It has been characterised as a major allergen, on the basis of its reactivity with 6 out of 6 sera tested (Burks et al, 1992, supra). Others have also confirmed its importance; Clarke demonstrated that 71% of subjects possessed specific IgE to Ara h 2 upon western blotting of crude peanut extract. Kleber-Janke et al. have demonstrated that 85% of subjects possessed IgE towards their recombinant form upon western blotting, and de Jong's group have shown that approximately 78% of their group demonstrate specific IgE to purified natural Ara h 2 (Clarke et al., *Clin Exp Allergy* 28: 1251-7, 1998; de Jong et al, 1998 supra; Kleber-Janke et al., *Int Arch Allergy Immunol* 119: 265-274, 1999).

Reference to "Ara h 1" should be understood as a reference to all forms of this molecule including reference to any isoforms which may arise from alternative splicing of Ara h 1 mRNA or functional mutant or polymorphic forms of Ara h 1. It should still further be understood to extend to any protein encoded by the Ara h 1 gene, any subunit polypeptide, such as precursor forms which may be generated, whether existing as a monomer, multimer or fusion protein. It also includes reference to analogues or equivalents of Ara h 1 such as may occur where a product which naturally comprises Ara h 1 is synthetically generated for the purpose of generating a product such as a food additive. The present invention thereby provides T cell epitopes and methods for their use in the diagnosis and treatment of any condition characterised by hypersensitivity to an Ara h 1 or Ara h 1-like molecule, such as peanut allergy or a tree-nut allergy, or an allergy to an antigen present in a composition, such as food, which composition also comprises Ara h 1. Preferably, said Ara h 1 comprises the sequence set forth in SEQ ID NO:9 and Ara h 2 comprises the sequence set forth in SEQ ID NO: 10.

Reference to "T cells" should be understood as a reference to any cell comprising a T cell receptor. In this regard, the T cell receptor may comprise any one or more of the α, β, γ or δ chains. The present invention is not intended to be limited to any particular functional sub-class of T cells although in a preferred embodiment the subject T cell is a T helper cell and still more preferably a Th2-type cell and/or Treg cell. In this regard, reference to "modifying T cell function" should be understood as a reference to modifying any one or more functions which a T cell is capable of performing. For example, the subject function may be proliferation, differentiation or other form of cellular functional activity such as the production of cytokines. In one embodiment the subject functional activity is proliferation.

In terms of "modifying the function" of T cells isolated from subjects having a condition characterised by an aberrant, unwanted or inappropriate immune response to Ara h 1 and/or Ara h 2 or to a composition which comprises Ara h 1 and/or Ara h 2, it should be understood that this is not necessarily a reference to modifying the function of all the T cells in a given biological sample but is likely, in fact, to reflect the modification of functioning of only some of the T cells in the sample. For example, only a portion of the T helper cells in a given T cell sample may functionally respond to contact with the subject peptide. Such a partial response should be understood to fall within the scope of the present invention. It should also be understood that the T cells which are derived from the subject may be freshly harvested T cells or they may have undergone some form of in vitro or in vivo manipulation prior to testing. For example, T cell lines may have been generated from the cell sample and it is these T cell lines which then form the subject derived T cell population which is tested in accordance with the present invention. To the extent that the subject functional activity is T cell proliferation, the T cell proliferation assay is preferably performed as disclosed herein. Still more preferably, the subject modification of T cell function is the induction of proliferation. In this regard, reference to "Ara h 1-reactive" or "Arah 2-reactive" T cells should be understood as a reference to a T cell which responds functionally to HLA presentation of an Ara h 1 and/or Ara h 2 T cell epitope, respectively. Similarly, reference to "Ara h 1-specific" or "Ara h 2-specific" IgE should be understood as a reference to IgE directed to Ara h 1 or Ara h 2 B cell epitopes, respectively.

Reference to an "aberrant, unwanted or otherwise inappropriate" immune response should be understood as a reference to any form of physiological activity which involves the activation and/or functioning of one or more immune cells where that activity is inappropriate in that it is of an inappropriate type or proceeds to an inappropriate degree. It may be aberrant in that according to known immunological principles it either should not occur when it does so or else should occur when it does not do so. In another example, the immune response may be inappropriate in that it is a physiologically normal response but which is unnecessary and/or unwanted, such as occurs with respect to type-I hypersensitivity responses to innocuous allergens. In the context of the present invention, this immune response may be directed to Ara h 1 and/or Ara h 2 or it may be directed to a different allergen which is present in a composition together with Ara h 1 and/or Ara h 2. Without limiting the present invention to any one theory or mode of action, it has been determined that even where the hypersensitivity response is directed to an allergen other than Ara h 1 and/or Ara h 2, which allergen is present in a composition which nevertheless comprises Ara h 1 and/or Ara h 2, treatment via the method of the present invention which is directed to Ara h 1 and/or Ara h 2 nevertheless induces beneficial modulation of Th2 and Treg functionality such that the hypersensitivity which exists to the unrelated allergen is nevertheless reduced. Preferably said immune response is peanut hypersensitivity.

By "peanut hypersensitivity" is meant the induction of clinical symptoms of IgE mediated peanut hypersensitivity. However, it should be understood that although clinical symptoms may be evident, not all such individuals would necessarily exhibit detectable levels of peanut specific serum IgE which is measured using the Kallestad Allercoat EAST System (Sanofi-Pasteur Diagnostics, USA), although such individuals should nevertheless be understood to fall within the scope of the definition of those exhibiting "peanut hypersensitivity". Alternatively, testing may proceed utilising any of the EAST, Pharmacia or the UniCap systems or allergen skin prick testing. Reference to "Ara h 1 and/or Ara h 2 hypersensitivity" should be understood to have a corresponding meaning in the context of reactivity to the Ara h 1 and/or Ara h 2 protein.

In accordance with the preceding aspects, said peptides are selected from the list consisting of:

(i)
FQNLQNHRIVQIEAKPNTLV (SEQ ID NO: 11)

(ii)
STRSSENNEGVIVKVSKE (SEQ ID NO: 12)

(iii)
EVKPDKKNPQLQ (SEQ ID NO: 4)

(iv)
VEIKEGALMLPHFNSKA (SEQ ID NO: 13)

(v)
VFIMPAAHPVAINASS (SEQ ID NO: 14)

(vi)
ANLRPXEQHLM (SEQ ID NO: 15)

(vii)
EFENNQRXMXEALQ (SEQ ID NO: 16)

(viii)
NNFGKLFEVKPDKKNPQLQ (SEQ ID NO: 17)

(ix)
GDVFIMPAAHPVAINASSE (SEQ ID NO: 18)

(x)
SQLERANLRPXEQHLM (SEQ ID NO: 19)

(xi)
ELNEFENNQRXMXEALQ (SEQ ID NO: 20)

(xii)
FQNLQNHRIV (SEQ ID NO: 21)

(xiii)
RIVQIEAKPNTLV (SEQ ID NO: 22)

(xiv)
ENNEGVIVKVSKE (SEQ ID NO: 23)

(xv)
EVKPDKKNPQLQD (SEQ ID NO: 24)

-continued (xvi)
EFENNQRXMXEALQQI (SEQ ID NO: 25)

(xvii)
NNFGKLFEVKPDKKNPQLQD (SEQ ID NO: 26)

(xviii)
ELNEFENNQRXMXEALQQI (SEQ ID NO: 27)

(xx)
WSTRSSENNEGVIVKVSKE (SEQ ID NO: 28)

(xxi)
GDVFIMPAAHPVAINASS (SEQ ID NO: 29)

or functional derivatives or homologues thereof wherein residue X is cysteine or serine.

In one embodiment, said residue X is serine.

Preferably, said peptides are selected from:

(i)
FQNLQNHRIVQIEAKPNTLV (SEQ ID NO: 11)

(ii)
STRSSENNEGVIVKVSKE (SEQ ID NO: 12)

(iii)
EVKPDKKNPQLQ (SEQ ID NO: 4)

(iv)
VEIKEGALMLPHFNSKA (SEQ ID NO: 13)

(v)
VFIMPAAHPVAINASS (SEQ ID NO: 14)

(vi)
ANLRPSEQHLM (SEQ ID NO: 30)

(vii)
EFENNQRSMSEALQ (SEQ ID NO: 31)

(viii)
EVKPDKKNPQLQD (SEQ ID NO: 24)

(ix)
EFENNQRSMSEALQQI (SEQ ID NO: 32)

or functional derivatives or homologues thereof.

In another embodiment, said immunomodulatory composition comprises each of the Ara h 1 and Ara h 2 T cell peptides from the list consisting of:

(i)
FQNLQNHRIVQIEAKPNTLV; (SEQ ID NO: 11)

(ii)
STRSSENNEGVIVKVSKE; (SEQ ID NO: 12)

-continued (iii)
EVKPDKKNPQLQ (SEQ ID NO: 33)
and/or
EVKPDKKNPQLQD; (SEQ ID NO: 24)

(iv)
VEIKEGALMLPHFNSKA; (SEQ ID NO: 13)

(v)
VFIMPAAHPVAINASS; (SEQ ID NO: 14)

(vi)
ANLRPSEQHLM; (SEQ ID NO: 30)
and (vii)
EFENNQRSMSEALQ (SEQ ID NO: 31)
and/or
EFENNQRSMSEALQQI. (SEQ ID NO: 32)

or functional derivatives or homologues thereof.

The reduction of peanut, Ara h 1 and Ara h 2 hypersensitivity (and allergen hypersensitivity more generally) is discussed in more detail hereafter. Briefly, however, this may take the form of either partially or completely desensitising or tolerising an individual to Ara h 1 and Ara h 2 specifically or peanut or other proteins more generally.

Reference to a "peptide" includes reference to a peptide, polypeptide or protein or parts thereof. The peptide may be glycosylated or unglycosylated and/or may contain a range of other molecules fused, linked, bound or otherwise associated to the protein such as amino acids, lipids, carbohydrates or other peptides, polypeptides or proteins. Reference hereinafter to a "peptide" includes a peptide comprising a sequence of amino acids as well as a peptide associated with other molecules such as amino acids, lipids, carbohydrates or other peptides, polypeptides or proteins.

"Derivatives" include fragments, parts, portions and variants from natural, synthetic or recombinant sources including fusion proteins. Parts or fragments include, for example, active regions of the subject peptide. Derivatives may be derived from insertion, deletion or substitution of amino acids. Amino acid insertional derivatives include amino and/or carboxylic terminal fusions as well as intrasequence insertions of single or multiple amino acids. Insertional amino acid sequence variants are those in which one or more amino acid residues are introduced into a predetermined site in the protein although random insertion is also possible with suitable screening of the resulting product. Deletional variants are characterized by the removal of one or more amino acids from the sequence.

Substitutional amino acid variants are those in which at least one residue in the sequence has been removed and a different residue inserted in its place. An example of substitutional amino acid variants are conservative amino acid substitutions. Conservative amino acid substitutions typically include substitutions within the following groups: glycine and alanine; valine, isoleucine and leucine; aspartic acid and glutamic acid; asparagine and glutamine; serine and threonine; lysine and arginine; and phenylalanine and tyrosine. Additions to amino acid sequences include fusions with other peptides, polypeptides or proteins. In one embodiment, cysteine residues are substituted with serine, as exemplified herein.

Chemical and functional equivalents of the subject peptide should be understood as molecules exhibiting any one or more of the functional activities of these molecules and may be derived from any source such as being chemically synthesized or identified via screening processes such as natural product screening.

Homologues include peptides derived from varieties other than peanuts, such as peptides derived from other tree nuts.

Analogues contemplated herein include, but are not limited to, modification to side chains, incorporating of unnatural amino acids and/or their derivatives during peptide, polypeptide or protein synthesis and the use of crosslinkers and other methods which impose conformational constraints on the proteinaceous molecules or their analogues. Mutants include molecules which exhibit modified functional activity (for example, Ara h 1 peptides which express one or more T cell epitopes but lack B cell reactivity).

Examples of side chain modifications contemplated by the present invention include modifications of amino groups such as by reductive alkylation by reaction with an aldehyde followed by reduction with $NaBH_4$; amidination with methylacetimidate; acylation with acetic anhydride; carbamoylation of amino groups with cyanate; trinitrobenzylation of amino groups with 2, 4, 6-trinitrobenzene sulphonic acid (TNBS); acylation of amino groups with succinic anhydride and tetrahydrophthalic anhydride; and pyridoxylation of lysine with pyridoxal-5-phosphate followed by reduction with $NaBH_4$.

The guanidine group of arginine residues may be modified by the formation of heterocyclic condensation products with reagents such as 2,3-butanedione, phenylglyoxal and glyoxal. The carboxyl group may be modified by carbodiimide activation via O-acylisourea formation followed by subsequent derivatisation, for example, to a corresponding amide. Sulphydryl groups may be modified by methods such as carboxymethylation with iodoacetic acid or iodoacetamide; performic acid oxidation to cysteic acid; formation of mixed disulphides with other thiol compounds; reaction with maleimide, maleic anhydride or other substituted maleimide; formation of mercurial derivatives using 4-chloromercuribenzoate, 4-chloromercuriphenylsulphonic acid, phenylmercury chloride, 2-chloromercuri-4-nitrophenol and other mercurials; carbamoylation with cyanate at alkaline pH. Tryptophan residues may be modified by, for example, oxidation with N-bromosuccinimide or alkylation of the indole ring with 2-hydroxy-5-nitrobenzyl bromide or sulphenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, 4-amino butyric acid, 4-amino-3-hydroxy-5-phenylpentanoic acid, 6-aminohexanoic acid, t-butylglycine, norvaline, phenylglycine, ornithine, sarcosine, 4-amino-3-hydroxy-6-methylheptanoic acid, 2-thienyl alanine and/or D-isomers of amino acids. A list of unnatural amino acids contemplated herein is shown in Table 1.

TABLE 1

| Non-conventional amino acid | Code | Non-conventional amino acid | Code |
|---|---|---|---|
| -aminobutyric acid | Abu | L-N-methylalanine | Nmala |
| -amino- -methylbutyrate | Mgabu | L-N-methylarginine | Nmarg |
| aminocyclopropane-carboxylate | Cpro | L-N-methylasparagine | Nmasn |
|  |  | L-N-methylaspartic acid | Nmasp |
| aminoisobutyric acid | Aib | L-N-methylcycteine | Nmcys |
| aminonorbornyl-carboxylate | Norb | L-N-methylglutamine | Nmgln |
|  |  | L-N-methylglutamic acid | Nmglu |
| cyclohexylalanine | Chexa | L-N-methylhistidine | Nmhis |
| cyclopentylalanine | Cpen | L-N-methylisolleucine | Nmile |
| D-alanine | Dal | L-N-methylleucine | Nmleu |
| D-arginine | Darg | L-N-methyllysine | Nmlys |
| D-aspartic acid | Dasp | L-N-methylmethionine | Nmmet |
| D-cysteine | Dcys | L-N-methylnorleucine | Nmnle |
| D-glutamine | Dgln | L-N-methylnorvaline | Nmnva |
| D-glutamic acid | Dglu | L-N-methylornithine | Nmorn |
| D-histidine | Dhis | L-N-methylphenylalanine | Nmphe |
| D-isoleucine | Dile | L-N-methylproline | Nmpro |
| D-leucie | Dleu | L-N-methylserine | Nmser |
| D-lysine | Dlys | L-N-methylthreonine | Nmthr |
| D-methionine | Dmet | L-N-methyltryptophan | Nmtrp |
| D-ornithine | Dorn | L-N-methyltyrosine | Nmtyr |
| D-phenylalanine | Dphe | L-N-methylvaline | Nmval |
| D-proline | Dpro | L-N-methylethylglycine | Nmetg |
| D-serine | Dser | L-N-methyl-t-butylglycine | Nmtbug |
| D-threonine | Dthr | L-norleucine | Nle |
| D-tryptophan | Dtrp | L-norvaline | Nva |
| D-tyrosine | Dtyr | -methyl-aminoisobutyrate | Maib |
| D-valine | Dval | -methyl- -aminobutyrate | Mgabu |
| D- -methylalanine | Dmala | -methylcyclohexylalanine | Mchexa |
| D- -methylarginine | Dmarg | -methylcylcopentylalanine | Mcpen |
| D- -methylasparagine | Dmasn | -methyl- -napthylalanine | Manap |
| D- -methylaspartate | Dmasp | -methylpenicillamine | Mpen |
| D- -methylcysteine | Dmcys | N-(4-aminobutyl)glycine | Nglu |
| D- -methylglutamine | Dmgls | N-(2-aminoethyl)glycine | Naeg |
| D- -methylhistidine | Dmhis | N-(3-aminopropyl)glycine | Norn |
| D- -methylisoleucine | Dmile | N-amino- -methylbutyrate | Nmaabu |
| D- -methylleucine | Dmleu | -napthylalanine | Anap |

TABLE 1-continued

| Non-conventional amino acid | Code | Non-conventional amino acid | Code |
|---|---|---|---|
| D- -methyllysine | Dmlys | N-benzylglycine | Nphe |
| D- -methylmethionine | Dmmet | N-(2-carbamylethyl)glycine | Ngln |
| D- -methylornithine | Dmorn | N-(carbamylmethyl)glycine | Nasn |
| D- -methylphenylalanine | Dmphe | N-(2-carboxyethyl)glycine | Nglu |
| D- -methylproline | Dmpro | N-(carboxymethyl)glycine | Nasp |
| D- -methylserine | Dmser | N-cyclobutylglycine | Ncbut |
| D- -methylthreonine | Dmthr | N-cycloheptylglycine | Nchep |
| D- -methyltryptophan | Dmtrp | N-cyclohexylglycine | Nchex |
| D- -methyltyrosine | Dmty | N-cyclodecylglycine | Ncdec |
| D- -methylvaline | Dmval | N-cylcododecylglycine | Ncdod |
| D-N-methylalanine | Dnmala | N-cyclooctylglycine | Ncoct |
| D-N-methylarginine | Dnmarg | N-cyclopropylglycine | Ncpro |
| D-N-methylasparagine | Dnmasn | N-cycloundecylglycine | Ncund |
| D-N-methylaspartate | Dnmasp | N-(2,2-diphenylethyl)glycine | Nbhm |
| D-N-methylcysteine | Dnmcys | N-(3,3-diphenylpropyl)glycine | Nbhe |
| D-N-methylglutamine | Dnmgln | N-(3-guanidinopropyl)glycine | Narg |
| D-N-methylglutamate | Dnmglu | N-(1-hydroxyethyl)glycine | Nthr |
| D-N-methylhistidine | Dnmhis | N-(hydroxyethyl))glycine | Nser |
| D-N-methylisoleucine | Dnmile | N-(imidazolylethyl))glycine | Nhis |
| D-N-methylleucine | Dnmleu | N-(3-indolylyethyl)glycine | Nhtrp |
| D-N-methyllysine | Dnmlys | N-methyl- -aminobutyrate | Nmgabu |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyla-napthylalanine | Nmanap |
| D-N-methylvaline | Dnmval | N-methylpenicillamine | Nmpen |
| -aminobutyric acid | Gabu | N-(p-hydroxyphenyl)glycine | Nhtyr |
| L-t-butylglycine | Tbug | N-(thiomethyl)glycine | Ncys |
| L-ethylglycine | Etg | penicillamine | Pen |
| L-homophenylalanine | Hphe | L- -methylalanine | Mala |
| L- -methylarginine | Marg | L- -methylasparagine | Masn |
| L- -methylaspartate | Masp | L- -methyl-t-butylglycine | Mtbug |
| L- -methylcysteine | Mcys | L-methylethylglycine | Metg |
| L- -methylglutamine | Mgln | L- -methylglutamate | Mglu |
| L- -methylhistidine | Mhis | L- -methylhomophenylalanine | Mhphe |
| L- -methylisoleucine | Mile | N-(2-methylthioethyl)glycine | Nmet |
| L- -methylleucine | Mleu | L- -methyllysine | Mlys |
| L- -methylmethionine | Mmet | L- -methylnorleucine | Mnle |
| L- -methylnorvaline | Mnva | L- -methylornithine | Morn |
| L- -methylphenylalanine | Mphe | L- -methylproline | Mpro |
| L- -methylserine- | Mser | L- -methylthreonine | Mthr |
| L- -methyltryptophan | Mtrp | L- -methyltyrosine | Mtyr |
| L- -methylvaline | Mval | L-N-methylhomophenylalanine | Nmhphe |
| N-(N-(2,2-diphenylethyl) carbamylmethyl)glycine | Nnbhm | N-(N-(3,3-diphenylpropyl) carbamylmethyl)glycine | Nnbhe |
| 1-carboxy-1-(2,2-diphenyl- ethylamino)cyclopropane | Nmbc | | |

Crosslinkers can be used, for example, to stabilise 3D conformations, using homo-bifunctional crosslinkers such as the bifunctional imido esters having $(CH_2)_n$ spacer groups with n=1 to n=6, glutaraldehyde, N-hydroxysuccinimide esters and hetero-bifunctional reagents which usually contain an amino-reactive moiety such as N-hydroxysuccinimide and another group specific-reactive moiety.

It is possible to modify the structure of a peptide according to the invention for various purposes such as for increasing solubility, enhancing therapeutic or preventative efficacy, enhancing stability or increasing resistance to proteolytic degradation. A modified peptide may be produced in which the amino acid sequence has been altered, such as by amino acid substitution, deletion or addition, to modify immunogenicity and/or reduce allergenicity. Similarly components may be added to peptides of the invention to produce the same result.

For example, a peptide can be modified so that it exhibits the ability to induce T cell anergy. In this instance, critical binding residues for the T cell receptor can be determined using known techniques (for example substitution of each residue and determination of the presence or absence of T cell reactivity) In one example, those residues shown to be essential to interact with the T cell receptor can be modified by replacing the essential amino acid with another, preferably similar amino acid residue (a conservative substitution) whose presence is shown to alter T cell reactivity or T cell functioning. In addition, those amino acid residues which are not essential for T cell receptor interaction can be modified by being replaced by another amino acid whose incorporation may then alter T cell reactivity or T cell functioning but does not, for example, eliminate binding to relevant MHC proteins. In yet another example, mutant peptides may be created which exhibit normal T cell binding but abrogated IgE binding.

Exemplary conservative substitutions are detailed, below, and include:

| Original Residue | Exemplary Substitutions |
|---|---|
| Ala | Ser |
| Arg | Lys |
| Asn | Gln, His |
| Asp | Glu |
| Cys | Ser, Ala |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Such modifications will result in the production of molecules falling within the scope of "mutants" of the subject peptide as herein defined. "Mutants" should be understood as a reference to peptides which exhibit one or more structural features or functional activities which are distinct from those exhibited by the non-mutated peptide counterpart.

Peptides of the invention may also be modified to incorporate one or more polymorphisms resulting from natural allelic variation and D-amino acids, non-natural amino acids or amino acid analogues may be substituted into the peptides to produce modified peptides which fall within the scope of the invention. Peptides may also be modified by conjugation with polyethylene glycol (PEG) by known techniques. Reporter groups may also be added to facilitate purification and potentially increase solubility of the peptides according to the invention. Other well known types of modification including insertion of specific endoprotease cleavage sites, addition of functional groups or replacement of hydrophobic residues with less hydrophobic residues as well as site-directed mutagenesis of DNA encoding the peptides of the invention may also be used to introduce modifications which could be useful for a wide range of purposes. The various modifications to peptides according to the invention which have been mentioned above are mentioned by way of example only and are merely intended to be indicative of the broad range of modifications which can be effected.

As detailed hereinbefore, the present invention provides peptides which retain all or some of their capacity to interact with T cells but exhibit partially or completely inhibited, abrogated or otherwise down-regulated antibody reactivity. Effecting the down-regulation of antibody reactivity can be achieved by any suitable method, which methods would be well known to those skilled in the art. For example, to the extent that a B cell epitope is defined by its linear amino acid sequence, one may add, delete or substitute one or more amino acid residues in order to render the mutated linear sequence distinct from the naturally occurring sequence. To the extent that an epitope may be additionally, or alternatively, defined by a conformational epitope, one may seek to disrupt that conformation by disrupting a 2° or, to the extent that homodimers or heterodimers exist, a 3° structure of the peptide. This may be achieved, for example, by disrupting the formation of bonds, such as disulphide bonds, which are known to stabilise 2° and/or 3° structures. In terms of the T cell epitopes hereinbefore defined, these T cells epitopic regions do not comprise B cell epitopes.

In a related aspect, the inventors have designed a preferred set of seven peptides, five of which comprise Ara h 1 T cell epitopes and two of which comprise Ara h 2 T cell epitopes, which function particularly efficaciously, when administered together, to induce desensitisation or tolerance and thereby either prophylactically or therapeutically treat hypersensitivity to compositions, such as foods, comprising Ara h 1 and/or Ara h 2. These peptides are:

(i)
                                                    (SEQ ID NO: 11)
FQNLQNHRIVQIEAKPNTLV (ii)
                                                    (SEQ ID NO: 12)
STRSSENNEGVTVKVSKE (iii)
                                                    (SEQ ID NO: 4)
EVKPDKKNPQLQ
and/or
                                                    (SEQ ID NO: 24)
EVKPDKKNPQLQD (iv)
                                                    (SEQ ID NO: 13)
VEIKEGALMLPHFNSKA (v)
                                                    (SEQ ID NO: 14)
VFIMPAAHPVAINASS (vi)
                                                    (SEQ NO: 30)
ANLRPSEQHLM (vii)
                                                    (SEQ NO: 31)
EFENNQRSMSEALQ
and/or
                                                    (SEQ ID NO: 32)
EFENNQRSMSEALQQI Accordingly, in a preferred embodiment there is provided an immunomodulatory composition comprising each of the Ara h 1 and Ara h 2 T cell peptides from the list consisting of:

(i)
                                                    (SEQ ID NO: 11)
FQNLQNHRIVQIEAKPNTLV (ii)
                                                    (SEQ ID NO: 12)
STRSSENNEGVIVKVSKE (iii)
                                                    (SEQ ID NO: 4)
EVKPDKKNPQLQ
and/or
                                                    (SEQ ID NO: 24)
EVKPDKKNPQLQD (iv)
                                                    (SEQ ID NO: 13)
VEIKEGALMLPHFNSKA (v)
                                                    (SEQ ID NO: 14)
VFIMPAAHPVAINASS -continued (vi)
ANLRPSEQHLM
(SEQ ID NO: 30)

(vii)
EFENNQRSMSEALQ
(SEQ ID NO: 31)

and/or

EFENNQRSMSEALQQI
(SEQ ID NO: 32)

In a further aspect, there is provided a composition comprising each of the Ara h 1 and Ara h 2 T cell peptides from the list consisting of:

(i)
FQNLQNHRIVQIEAKPNTLV
(SEQ ID NO: 11)

(ii)
STRSSENNEGVIVKVSKE
(SEQ ID NO: 12)

(iii)
EVKPDKKNPQLQ
(SEQ ID NO: 4)

and/or

EVKPDKKNPQLQD
(SEQ ID NO: 24)

(iv)
VEIKEGALMLPHFNSKA
(SEQ ID NO: 13)

(v)
VFIMPAAHPVAINASS
(SEQ ID NO: 14)

(vi)
ANLRPSEQHLM
(SEQ ID NO: 30)

(vii)
EFENNQRSMSEALQ
(SEQ ID NO: 31)

and/or

EFENNQRSMSEALQQI
(SEQ ID NO: 32)

which peptides are capable of reducing Ara h 1 and/or Ara h 2 hypersensitivity or hypersensitivity to a composition comprising Ara h 1 and/or Ara h 2 when administered to a subject having a condition characterised by said hypersensitivity.

The peptides of the present invention may be prepared by recombinant or chemical synthetic means. According to a preferred aspect of the present invention, there is provided a recombinant peptide or mutant thereof which is preferentially immunologically reactive with T cells from individuals with peanut hypersensitivity, which is expressed by the expression of a host cell transformed with a vector coding for the peptide sequence of the present invention. The peptide may be fused to another peptide, polypeptide or protein. Alternatively, the peptide may be prepared by chemical synthetic techniques, such as by the Merrifield solid phase synthesis procedure. Furthermore, although synthetic peptides of the sequence given above represent a preferred embodiment, the present invention also extends to biologically pure preparations of the naturally occurring peptides or fragments thereof. By "biologically pure" is meant a preparation comprising at least about 60%, preferably at least about 70%, or preferably at least about 80% and still more preferably at least about 90% or greater as determined by weight, activity or other suitable means.

The present invention should therefore be understood to encompass peptides that comprise at least one T cell core epitopic region of Ara h 1 and/or Ara h 2, as hereinbefore defined, in conjunction with other amino acids (which may or may not be naturally occurring) or other chemical species. In a preferred aspect of the invention such peptides may comprise one or more epitopes of Ara h 1 and/or Ara h 2, which epitopes are T cell core epitopic regions. Peptides with one or more T cell epitopes of Ara h 1 and/or Ara h 2 are desirable for increased therapeutic effectiveness.

As detailed hereinbefore, the present invention is directed to a composition comprising the peptides hereinbefore defined. It should be understood, though, that the subject composition may comprise additional components, such as additional peptides. These peptides may encompass, for example, partial regions of the core minimal epitope. Alternatively, they may not comprise any part of a T cell epitope as disclosed herein but may be incorporated for either reasons. Examples of other peptides which may be included in the composition include, but are not limited to:

(i)
ALMLPHFNSKAMVIVVV
(SEQ ID NO: 33)

(ii)
NNFGKLFEVKPDKKNPQ
(SEQ ID NO: 34)

(iii)
SQLERANLRPXEQ
(SEQ ID NO: 35)

(iv)
ELNEFENNQRXM
(SEQ ID NO: 36)

(v)
NNFGKLFEVKPDKKNPQLQD
(SEQ ID NO: 26)

(vi)
NNFGKLFEVKPDKKNPQL
(SEQ ID NO: 38)

(vii)
SQLERANLRPXEQH
(SEQ ID NO: 39)

(viii)
KAMVIVVVNKGTGNLELVAV
(SEQ ID NO: 40)

(ix)
RELRNLPQQXGLRA
(SEQ ID NO: 41)

(x)
KAMVIVVVNKG
(SEQ ID NO: 42)

(xi)
AMVIVVVNKGTGNLELV
(SEQ ID NO: 43)

(xii)
VVNKGTGNLELVAVRK
(SEQ ID NO: 44)

or functional derivatives or homologues thereof wherein residue X is cysteine or serine.

One may also include still other peptides or molecules which may be advantageous given the particulars of a specific situation.

In another aspect, the present invention provides a nucleic acid molecule composition comprising one or more nucleic acid molecules encoding or complementary to a sequence encoding the T cell epitopes and peptides as hereinbefore defined or a derivative, homologue or analogue thereof.

It should be understood that reference to "peptides" includes reference to peptides comprising one or more T cell epitopes. A nucleic acid molecule encoding the subject peptide is preferably a sequence of deoxyribonucleic acids such as cDNA or a genomic sequence. A genomic sequence may comprise exons and introns. A genomic sequence may also include a promoter region or other regulatory regions.

The nucleic acid molecule may be ligated to an expression vector capable of expression in a prokaryotic cell (eg. *E. coli*) or a eukaryotic cell (eg. yeast cells, fungal cells, insect cells, mammalian cells or plant cells). The nucleic acid molecule may be ligated or fused or otherwise associated with a nucleic acid molecule encoding another entity such as, for example, a signal peptide. It may also comprise additional nucleotide sequence information fused, linked or otherwise associated with it either at the 3' or 5' terminal portions or at both the 3' and 5' terminal portions. The nucleic acid molecule may also be part of a vector, such as an expression vector. The latter embodiment facilitates production of recombinant forms of the subject peptide which forms are encompassed by the present invention.

Such nucleic acids may be useful for recombinant production of T cell epitopes of Ara h 1 and/or Ara h 2 or proteins comprising them by insertion into an appropriate vector and transfection into a suitable cell line. Such expression vectors and host cell lines also form an aspect of the invention.

In producing peptides by recombinant techniques, host cells transformed with a nucleic acid having a sequence encoding a peptide according to the invention or a functional equivalent of the nucleic acid sequence are cultured in a medium suitable for the particular cells concerned. Peptides can then be purified from cell culture medium, the host cells or both using techniques well known in the art such as ion exchange chromatography, gel filtration chromatography, ultrafiltration, electrophoresis or immunopurification with antibodies specific for the peptide.

Nucleic acids encoding Ara h 1 and/or Ara h 2 or peptides comprising T cell core epitopic regions of Ara h 1 and/or Ara h 2 may be expressed in bacterial cells such as *E. coli*, insect cells, yeast or mammalian cells such as Chinese hamster ovary cells (CHO). Suitable expression vectors, promoters, enhancers and other expression control elements are referred to in Sambruck et al (1989). Other suitable expression vectors, promoters, enhancers and other expression elements are well known to those skilled in the art. Examples of suitable expression vectors in yeast include Yep Sec 1 (Balderi et al., 1987, *Embo J.,* 6:229-234); pMFa (Kurjan and Herskowitz, 1982, *Cell.,* 30:933-943); JRY88 (Schultz et al., 1987, *Gene.,* 54:113-123) and pYES2 (Invitrogen Corporation, San Diego, Calif.). These vectors are freely available as are baculovirus and mammalian expression systems. For example, a baculovirus system is commercially available (ParMingen, San Diego, Calif.) for expression in insect cells while the pMsg vector is commercially available (Pharmacia, Piscataway, N.J.) for expression in mammalian cells.

For expression in *E. coli* suitable expression vectors include among others, pTrc (Amann et al., 1998, *Gene.,* 69:301-315) pGex (Amrad Corporation, Melbourne, Australia); pMal (N.E. Biolabs, Beverley, Mass.); pRit5 (Pharmacia, Piscataway, N.J.); pEt-11d (Novagen, Maddison, Wis.) (Jameel et al., 1990, *J. Virol.,* 64:3963-3966) and pSem (Knapp et al., 1990, *Bio Techniques.,* 8:280-281). The use of pTRC, and pEt-11d, for example, will lead to the expression of unfused protein. The use of pMal, pRit5, pSem and pGex will lead to the expression of allergen fused to maltose E binding protein (pMal), protein A (pRit5), truncated -galactosidase (PSEM) or glutathione S-transferase (pGex). When a T cell epitope of Ara h 1 or a peptide comprising it is expressed as a fusion protein, it is particularly advantageous to introduce an enzymatic cleavage site at the fusion junction between the carrier protein and the peptide concerned. The peptide of the invention may then be recovered from the fusion protein through enzymatic cleavage at the enzymatic site and biochemical purification using conventional techniques for purification of proteins and peptides. The different vectors also have different promoter regions allowing constitutive or inducible expression or temperature induction. It may additionally be appropriate to express recombinant peptides in different *E. coli* hosts that have an altered capacity to degrade recombinantly expressed proteins. Alternatively, it may be advantageous to alter the nucleic acid sequence to use codons preferentially utilised by *E. coli*, where such nucleic acid alteration would not effect the amino acid sequence of the expressed proteins.

Host cells can be transformed to express the nucleic acids of the invention using conventional techniques such as calcium phosphate or calcium chloride co-precipitation, DEAE-dextran-mediated transfection or electroporation. Suitable methods for transforming the host cells may be found in Sambruck et al. (1989), and other laboratory texts. The nucleic acid sequence of the invention may also be chemically synthesised using standard techniques.

In addition to recombinant production of peptides according to the invention, the nucleic acids may be utilised as probes for experimental or purification purposes.

Identification and synthesis of the peptides as disclosed herein now facilitates the development of a range of prophylactic and therapeutic treatment protocols for use with respect to peanut related immune conditions. Also facilitated is the development of reagents for use therein. Accordingly, the present invention should be understood to extend to the use of the peptides or functional derivatives, homologues or analogues thereof in the therapeutic and/or prophylactic treatment of patients. Such methods of treatment include, but are not limited to:

(i) Administration of the subject peptides to a patient as a means of desensitising or inducing immunological tolerance to peanut, Ara h 1 and/or Ara h 2 or Ara h 1-like and/or Ara h 2-like molecules. This may be achieved, for example, by inducing Ara h 1 and/or Ara h 2 directed Th2 anergy or apoptosis. In a preferred embodiment, such an outcome is achieved by the use of peptides which maintain T cell epitope reactivity but which are unable to undergo IgE binding. Alternatively, one may utilise treatment protocols which are based on the administration of specific concentrations of a given peptide in accordance with a specific regimen in order to induce tolerance. Such methodology may eliminate Ara h 1 and/or Ara h 2 hypersensitivity or it may reduce the severity of Ara h 1 and/or Ara h 2 hypersensitivity or sensitivity to an allergen present in a composition comprising Ara h 1 and/or Ara h 2, such as a peanut allergy. Reference herein to the treatment of Ara h 1 and/or Ara h 2 sensitivity should be understood to encompass within its scope the treatment of conditions characterised by sensitivity to compositions which comprise Ara h 1 and/or Ara h 2, such as peanuts generally, even if the sensitivity is directed to an allergen other than Ara h 1 and/or Ara h 2.

Preferably such treatment regimens are capable of modifying the T cell response or both the B and T cell response of the individual concerned. As used herein, modification of the allergic response of the individual suffering from peanut hypersensitivity can be defined as inducing either non-responsiveness or diminution in symptoms to the Ara h 1 molecule as determined by standard clinical procedures (Varney et al. 1991 *British Medical Journal* 302:265-269). Diminution in the symptoms includes any reduction in an allergic response in an individual to Ara h 1 after a treatment regimen has been completed. This diminution may be subjective or clinically determined, for example by using standard food challenge tests or standard skin tests known in the art.

Exposure of an individual to the peptides of the present invention may tolerise or anergise appropriate T cell subpopulations such that they become unresponsive to Ara h 1 and/or Ara h 2 and do not participate in stimulating an immune response upon such exposure. Preferably the peptides according to the invention will retain immunodominant T cell epitopes but possess abrogated IgE binding. Still further, even if the allergen in issue is not Ara h 1 and/or Ara h 2, but is directed to a different allergen which is present in the same composition as Ara h 1 and/or Ara h 2 (such as a different peanut allergen) immunisation with Ara h 1 and/or Ara h 2 may nevertheless induce a bystander suppressive effect which acts to reduce the degree of hypersensitivity to that allergen.

Administration of a peptide of the invention may modify the cytokine secretion profile as compared with exposure to naturally occurring Ara h 1 and/or Ara h 2 allergen. This exposure may also influence T cell subpopulations which normally participate in the allergic response to migrate away from the site or sites of normal exposure to the allergen and towards the site or sites of therapeutic administration. This redistribution of T cell subpopulations may ameliorate or reduce the ability of an individual's immune system to stimulate the usual immune response at the site of normal exposure to the allergen, resulting in diminution of the allergic symptoms.

Modification of the B cell response may be achieved, for example, via modulation of the cytokine profile produced by T cells, as detailed above. Specifically, decreasing T cell derived IL-4 and IL-13 production thereby decreasing IgE synthesis.

(ii) The peptides of the present invention may be used in the capacity of an adsorbent to remove Ara h 1 and/or Ara h 2 directed T cells from a biological sample or from a patient.

Accordingly, in another aspect the present invention provides a method for the treatment and/or prophylaxis of a condition in a subject, which condition is characterised by the aberrant, unwanted or otherwise inappropriate immune response to Ara h 1 and/or Ara h 2 or an allergen in a composition comprising Ara h 1 and/or Ara h 2, said method comprising administering to said subject an effective amount of an immunomodulatory composition as hereinbefore defined for a time and under conditions sufficient to remove or reduce the presence or function in said subject of T cells directed to said Ara h 1 and/or Ara h 2 or other allergen.

Preferably said condition is hypersensitivity to peanuts or tree nuts which contain Ara h 1 and Ara h 2 or Ara h 1-like or Ara h 2-like molecules, such as hazelnuts, almonds or Brazil nuts.

In one embodiment, said method desensitises or induces immunological tolerance to Ara h 1 and/or Ara h 2 or other allergen of said composition.

In another embodiment, said desensitization or tolerance is achieved by inducing T cell anergy or apoptosis.

In still another embodiment, said desensitisation or tolerance is achieved by inducing Ara h 1 or Ara h 2-specific Treg cells.

An "effective amount" means an amount necessary at least partly to attain the desired immune response, or to delay the onset or inhibit progression or halt altogether, the onset or progression of a particular condition being treated. The amount varies depending upon the health and physical condition of the individual to be treated, the taxonomic group of individual to be treated, the degree of protection desired, the formulation of the composition, the assessment of the medical situation, and other relevant factors. It is expected that the amount will fall in a relatively broad range that can be determined through routine trials.

The subject of the treatment or prophylaxis is generally a mammal such as but not limited to human, primate, livestock animal (e.g. sheep, cow, horse, donkey, pig), companion animal (e.g. dog, cat), laboratory test animal (e.g. mouse, rabbit, rat, guinea pig, hamster), captive wild animal (e.g. fox, deer). Preferably the mammal is a human or primate. Most preferably the mammal is a human.

Reference herein to "treatment" and "prophylaxis" is to be considered in its broadest context. The term "treatment" does not necessarily imply that a subject is treated until total recovery. Similarly, "prophylaxis" does not necessarily mean that the subject will not eventually contract a disease condition. Accordingly, treatment and prophylaxis include amelioration of the symptoms of a particular condition or preventing or otherwise reducing the risk of developing a particular condition. The term "prophylaxis" may be considered as reducing the severity or onset of a particular condition. "Treatment" may also reduce the severity of an existing condition.

Administration of the composition of the present invention (herein referred to as "agent") in the form of a pharmaceutical composition, may be performed by any convenient means. The agent of the pharmaceutical composition is contemplated to exhibit therapeutic activity when administered in an amount which depends on the particular case. The variation depends, for example, on the human or animal and the agent chosen. A broad range of doses may be applicable. Considering a patient, for example, from about 0.01 µg to about 1 mg of an agent may be administered per dose. Dosage regimens may be adjusted to provide the optimum therapeutic response. For example, several divided doses may be administered daily, weekly, monthly or other suitable time intervals or the dose may be proportionally reduced as indicated by the exigencies of the situation. In another example, said composition is administered initially to induce tolerance and then, if necessary, booster administrations of the composition are administered to maintain tolerance. These boosters may be administered monthly, for example, and may be administered for any period of time, including the life of the patient.

The agent may be administered in a convenient manner such as by the oral, intravenous (where water soluble), intraperitoneal, intramuscular, subcutaneous, intradermal (with or without using a traditional needle or other transdermal delivery device), transdermal, intranasal, sublingual or suppository routes or implanting (e.g. using slow release molecules). Preferably, said composition is administered intradermally. The agent may be administered in the form of pharmaceutically acceptable nontoxic salts, such as acid addition salts or metal complexes, e.g. with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. If the active ingredient is to be administered in tablet form, the tablet may contain a binder such as tragacanth, corn starch or gelatin; a disintegrating agent, such as alginic acid; and a lubricant, such as magnesium stearate.

In accordance with these methods, the agent defined in accordance with the present invention may be coadministered with one or more other compounds or molecules. By "coadministered" is meant simultaneous administration in the same formulation or in two different formulations via the same or different routes or sequential administration by the same or different routes. By "sequential" administration is meant a time difference of from seconds, minutes, hours or days between the administration of the two types of molecules. These molecules may be administered in any order. It should also be understood that the peptides of the present invention may be themselves administered simultaneously or sequentially. They may be administered as one or more compositions, either simultaneously or sequentially. For example, one may formulate some of the peptides in one formulation and the others in a separate formulation; with these two formulations being given one in each arm. Alternatively, additional separate formulations could be generated and administered, either simultaneously to different sites or sequentially. It is well within the skill of the person in the art to design and generate the production of an appropriate formulation or mix of formulations.

Another aspect of the present invention contemplates the use of an immunomodulatory composition as hereinbefore defined in the manufacture of a medicament for the treatment of a condition in a mammal, which condition is characterised by an aberrant, unwanted or otherwise inappropriate immune response to Ara h 1 and/or Ara h 2.

Preferably said condition is hypersensitivity to peanuts or a tree nut which contains Ara h 1 and/or Ara h 2 or Ara h 1-like and/or Ara h 2-like molecules, such as a hazelnut.

In yet another further aspect, the present invention contemplates a vaccine comprising the composition as hereinbefore defined together with one or more pharmaceutically acceptable carriers and/or diluents. Said composition is referred to as the active ingredient.

The pharmaceutical forms suitable for injectable use include sterile aqueous solutions (where water soluble) or dispersions and sterile powders for the extemporaneous preparation of sterile injectable solutions or dispersion or may be in the form of a cream or other form suitable for topical application. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosal and the like. Tonicity adjusting agents are useful to keep the preparation isotonic with human plasma and thus avoid tissue damage. Commonly used tonicity agents include Dextrose, Trehalose, Glycerin and Mannitol. Glycerol and sodium chloride are other options but are less commonly used. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilisation. Generally, dispersions are prepared by incorporating the various sterilised active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the active ingredients are suitably protected they may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions in such that a suitable dosage will be obtained. Preferred compositions or preparations according to the present invention are prepared so that an oral dosage unit form contains between about 0.1 μg and 1000 μs of active compound.

The tablets, troches, pills, capsules and the like may also contain the components as listed hereafter: a binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound(s) may be incorporated into sustained-release preparations and formulations.

The pharmaceutical composition may also comprise genetic molecules such as a vector capable of transfecting target cells where the vector carries a nucleic acid molecule encoding a modulatory agent. The vector may, for example, be a viral vector.

Routes of administration include, but are not limited to, respiratorally (eg. intranasally or orally via aerosol), intratracheally, nasopharyngeally, intravenously, intraperitoneally, subcutaneously, intracranially, intradermally, transdermally, intramuscularly, intraoccularly, intrathecally, intracereberally, intranasally, infusion, orally, rectally, via IV drip patch, implant and sublingual. Preferably, said route of administration is subcutaneously, intradermally, transdermally or intranasally.

Yet another aspect of the present invention relates to the compositions, as hereinbefore defined, when used in the method of the present invention.

The present invention is further described by reference to the following non-limiting examples.

Example 1

Ara h 1 and Ara h 2 are the most allergenic and abundant proteins in peanut, making peptides comprising their dominant T-cell epitopes essential for inclusion in a therapy. Another important consideration when selecting peptides for immunotherapy, is whether they can be presented by different MHC class II molecules (HLA molecules in humans) and therefore be suitable for treating a genetically diverse human population. The HLA-restriction of peptide presentation to T cells was tested using blocking antibodies and HLA-genotyping and showed that every T cell epitope identified could be presented on two or more different HLA-molecules. Furthermore, it was demonstrated that the identified T cell epitopes were collectively presented on a combination of HLA-DR, HLA-DQ and HLA-DP molecules (FIG. 17). Inclusion of HLA-DQ and -DP-restricted T cell epitopes is particularly advantageous for a therapeutic since these HLA-types are more conserved in mixed populations than HLA-DR molecules, enabling broader population coverage with fewer T cell epitope sequences.

Adjacent or overlapping T cell epitopes were combined into single peptides (<20 aa long) to minimise the number of peptides in the final therapeutic set resulting in three candidate peptides from Ara h 2 and seven from Ara h 1. Since cysteine residues can be problematic for peptide stability and biological reactivity, cysteine residues were substituted with structurally conserved but less reactive serine residues. Minor changes were also made to two Ara h 1 peptides to improve stability and/or solubility (FIG. 17). In all cases it has been confirmed that T-cell reactivity to the variant peptide has been retained.

Figure 1B:
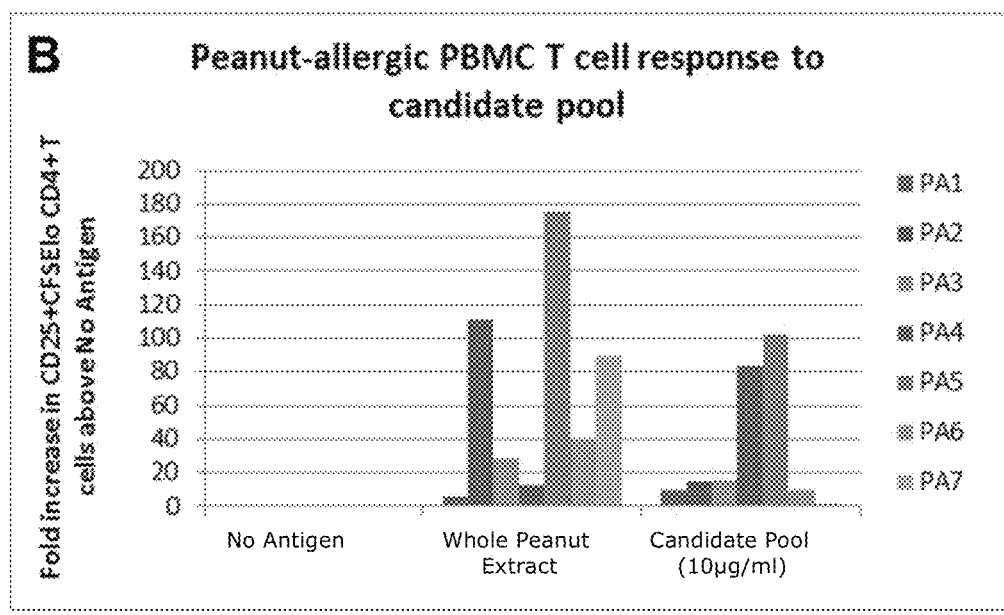

Preclinical screening of these peptides confirms PBMC T-cell reactivity (FIG. 1), lack of inflammatory cell activation (FIG. 2) and serum stability in an additional peanut-allergic cohort (n=40). It has been confirmed that PBMC T-cell recognition of one or more of these ten peptides in 100% of subjects (n=20) analysed, with 50-90% responding to each peptide. The analyses to date clearly demonstrate that the ten peptides in FIG. 17, provide a sufficient, feasible and suitable mixture.

Example 2

Brief Overview of Steps

Figure 3:
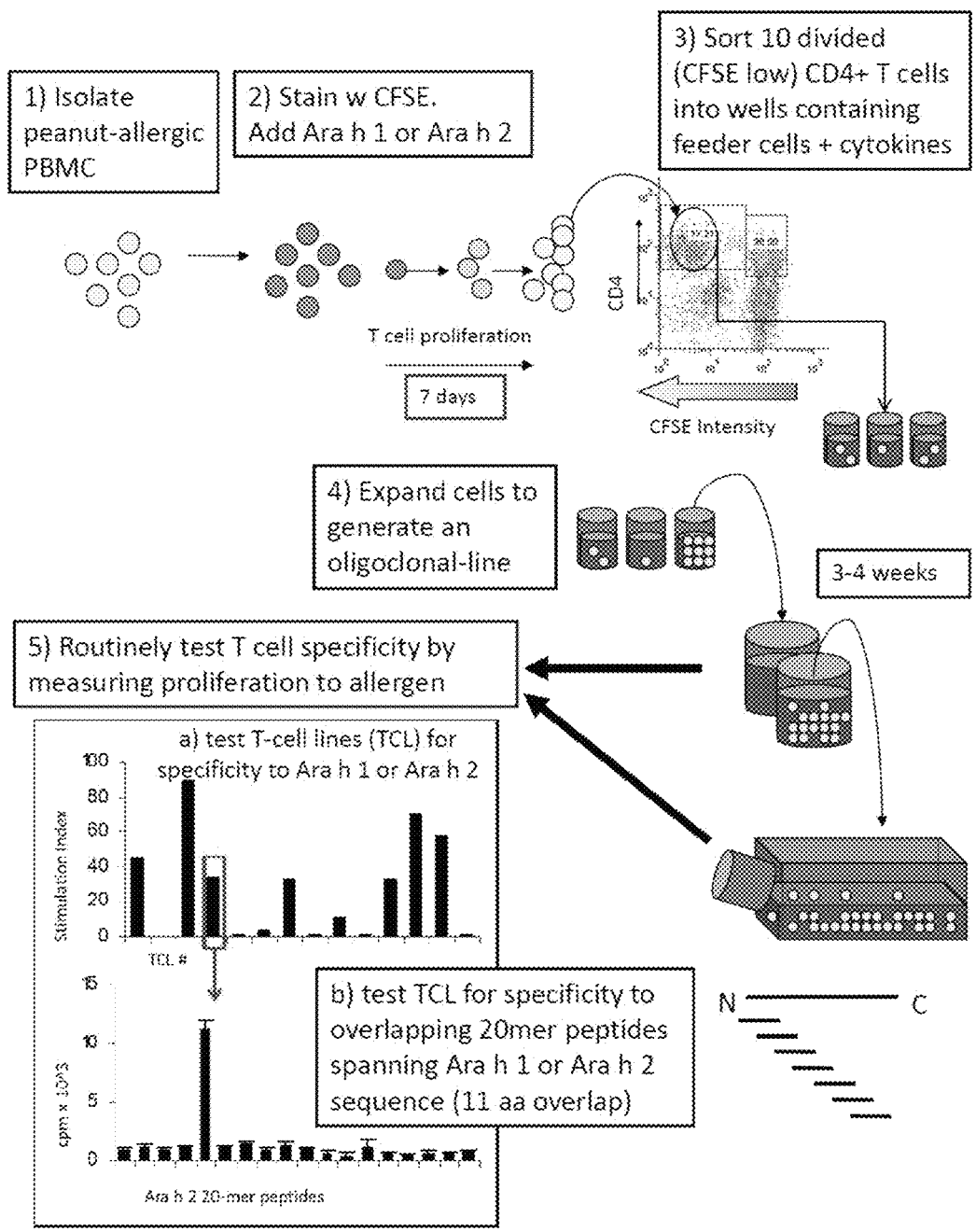
FIG. 3 is a schematic representation of the method employed to identify the dominant epitopes of the major peanut allergens Ara h 1 and Ara h 2.
Figure 4:
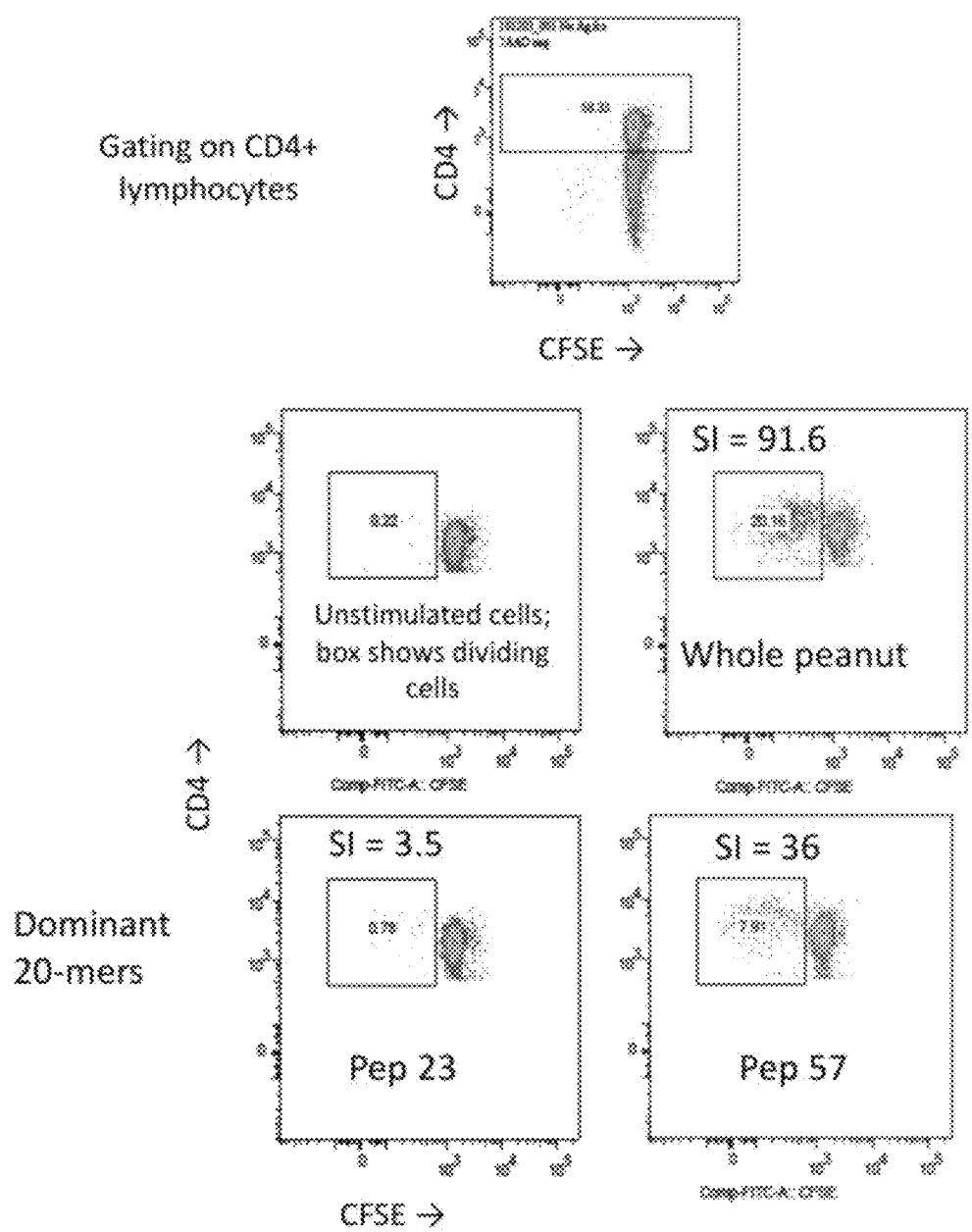
FIG. 4 is a graphical representation of a 7-day CFSE assay designed to detect the ability of dominant 20-mer peptides to induce T cell proliferation in whole PBMC of peanut-allergic donors. The numbers in the boxes indicate % of dividing (CFSE low) CD4+ T cells SI=fold increase in dividing cells above unstimulated control.
Figure 5:
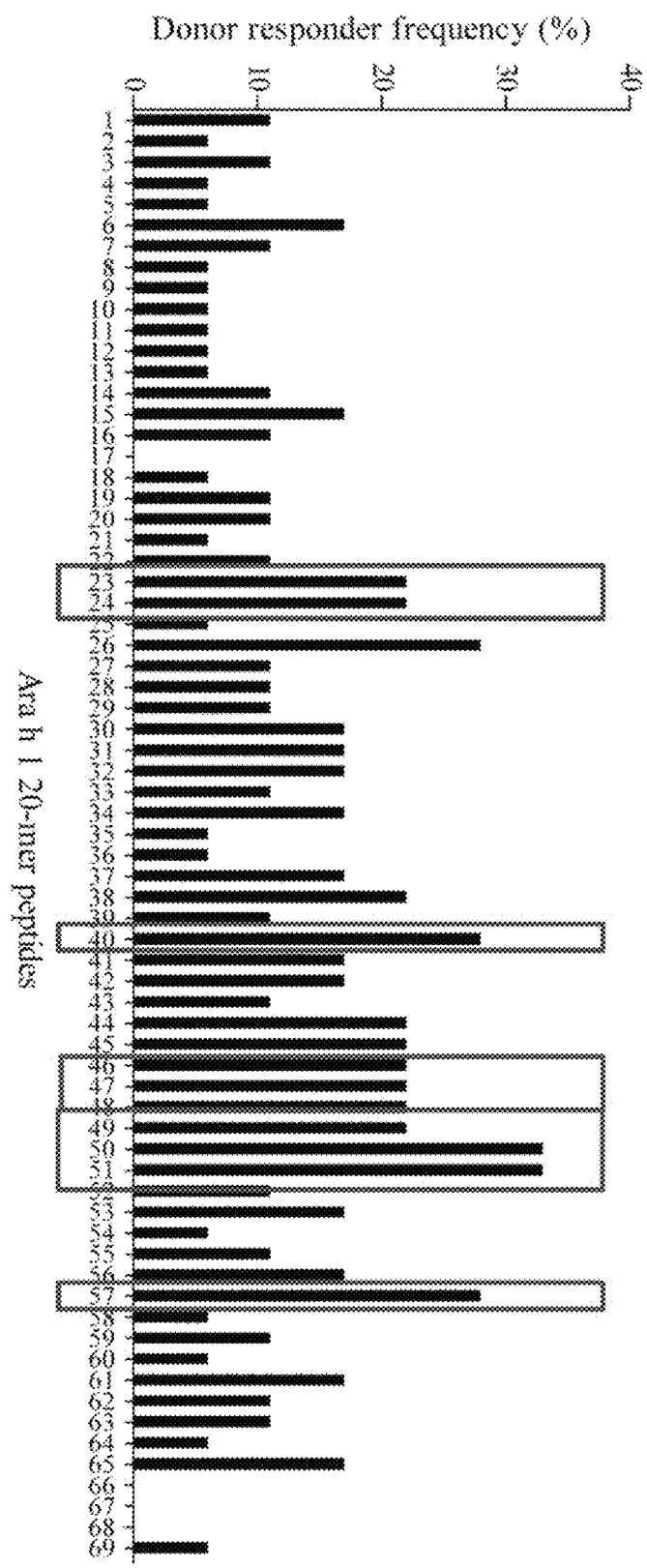
FIG. 5 is a graphical representation demonstrating responder frequency of T-cell lines to Ara h 1 20-mer peptides. Boxes indicate the 9 dominant 20-mers ultimately selected (based on multiple parameters).
Figure 6:
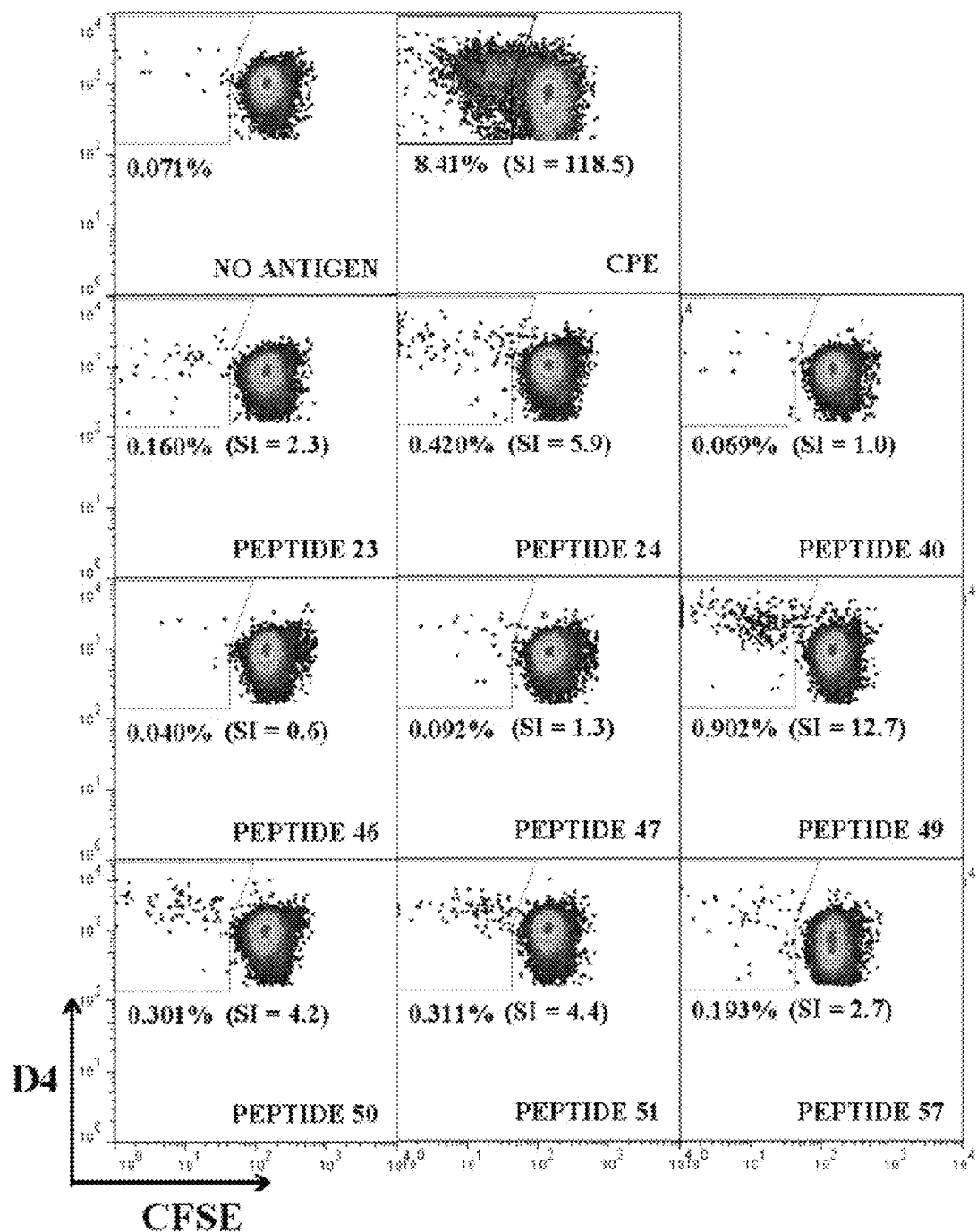
FIG. 6 is a graphical representation of PBMC screening with dominant Ara h 1 20-mers. The ability of dominant 20-mers to target specific CD4+ T-cells in PBMC from peanut-allergic donors was tested.
Figure 7:
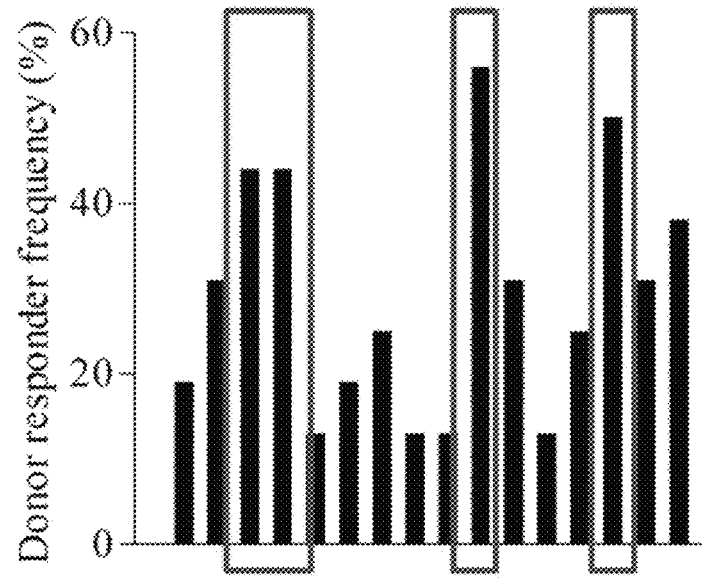
FIGS. 7A and 7B are graphical representations demonstrating responder frequency of T-cell lines to Ara h 2 20-mer peptides and number of specific TCL per 20-mer. Boxes indicate 4 dominant 20-mer peptides ultimately selected based on multiple parameters.
Figure 8:
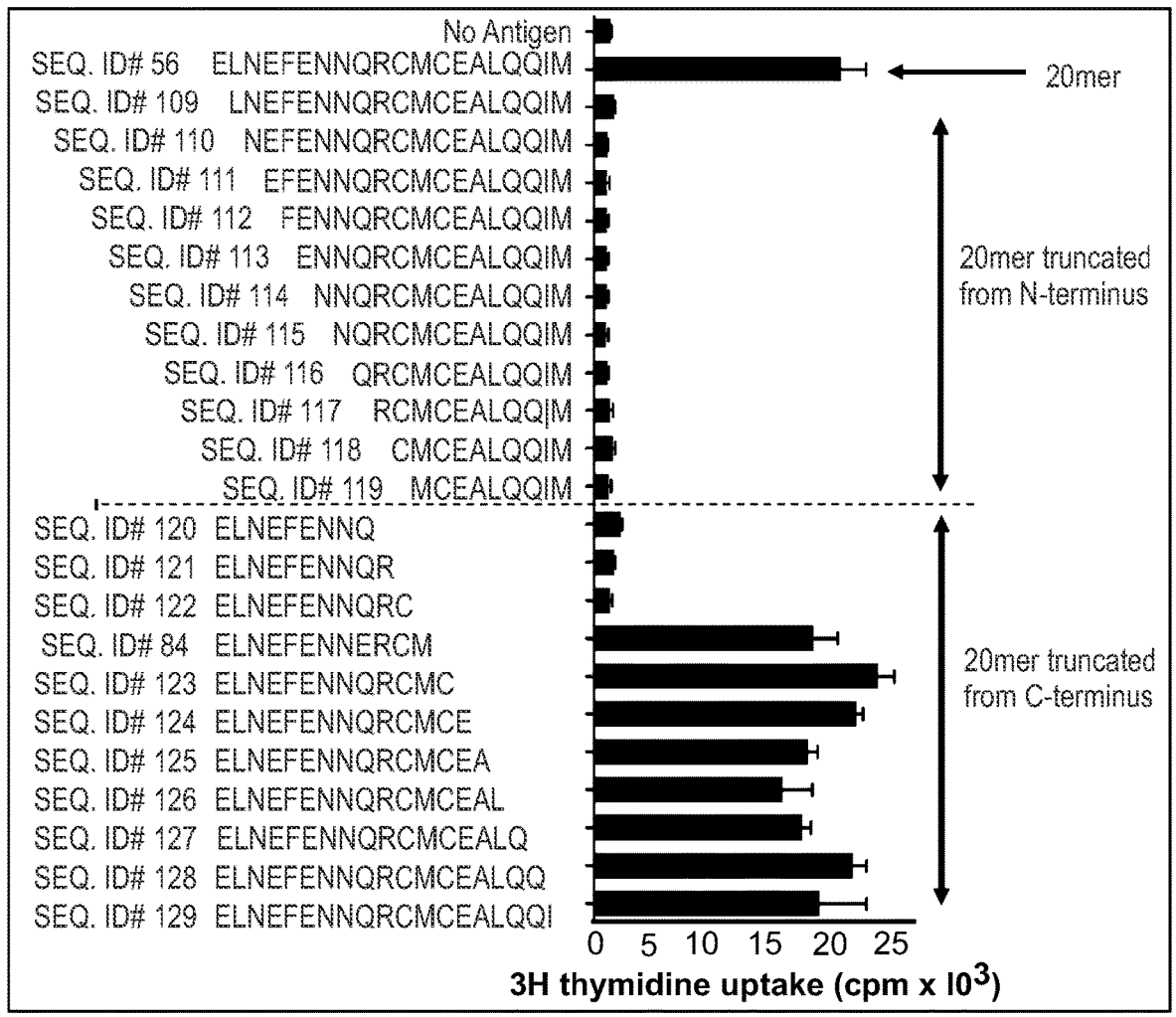
FIG. 8 is a graphical representation of the core T cell epitope mapping results.

| 1) Identification of dominant T cell epitopes of major peanut allergens Ara h 1 and Ara h 2 (FIGS. 3 and 4) |
|---|
| Isolated CD4+ T cells specific for Ara h 1 or Ara h 2 from PBMC of peanut-allergic subjects<br>Determined T cell specificity to overlapping 20-mer peptides spanning full Ara h 1 (FIGS. 5 and 6) or 2 (FIG. 7) sequence<br>Selected dominant 20-mers and mapped core T cell epitope sequences within them (FIG. 8)<br>2) Determining HLA-restriction of core T cell epitopes |
| Blocked T cell epitope presentation to specific T cells using anti-HLA antibodies (FIG. 9)<br>HLA-genotyped subjects used for T cell epitope-mapping<br>Further assessed HLA-binding degeneracy of T cell epitopes with algorithms<br>3) Design of therapeutic candidate peptides |
| Replaced cysteine residues with serine residues<br>Combined overlapping T cell epitopes into single peptides 20 aa long (10 peptides) (Tables 16-18)<br>Designed shorter peptide variants based on single T cell epitopes (13 peptides)<br>Synthesised all 23 peptides to >95% GLP-grade purity & determined solutions for solubility<br>4) Selection and testing of final therapeutic mixture |
| Compared PBMC T cell reactivity to all 23 peptides in peanut-allergic cohort and selected final 7-peptide therapeutic<br>Assessed PBMC T cell response to 7-peptide mix at 2 therapeutic doses in peanut-allergic cohort<br>Tested basophil response to 7-peptide mix at 4-log dose range in peanut-allergic cohort |

Materials and Methods

Subjects: Peanut-allergic adult subjects were recruited from The Alfred Allergy Clinic, Melbourne, Australia. Peanut-allergic subjects had clinical symptoms of IgE-mediated peanut allergy and peanut-specific IgE CAP score≥2 (≥1.16 kUA/1; Pharmacia CAP System™, Pharmacia Diagnostics, Uppsala, Sweden) and many had a history of anaphylaxis. Some subjects were genotyped (HLA-DRB1, -DQB1 and -DPB1, exon 2) by the Victorian Transplantation and Immunogenetics Service. The study was approved by The Alfred and Monash University Ethics Committees and informed written consent obtained from each subject.

Antigens: Crude peanut extract (CPE) was prepared from commercial unsalted, dry-roasted peanuts as described elsewhere, (de Leon et al. *Clin Exp Allergy*. 2003; 33(9):1273-80) dialyzed against phosphate-buffered saline (PBS) and filter-sterilized (0.2 µm). Natural Ara h 1 and Ara h 2 were enriched from CPE based on published methodology. (de Jong E C et al. *Clin Exp Allergy*. 1998; 28(6):743-51) Briefly, CPE was buffer exchanged into 20 mM TRIS-bis-propane (TBP), pH 7.2, using Vivaspin columns (Sartorius Stedim Biotech S.A., Aubagne, France) and applied onto a 5 mL Mono-Q 10/10 column (Pharmacia FPLC System, St Albans, UK) equilibrated with TBP. After washing with TBP, a linear gradient of 30 mL 0-1 M NaCl/TBP was applied to elute bound proteins (1 mL/min). Fractions, 0.5 mL, were analyzed by SDS-PAGE and those containing Ara h 1 or Ara h 2 with minimal other proteins pooled and dialyzed against PBS. Endotoxin contents were 1.7, 4.0 and 78.0 EU/mg for CPE, Ara h 1 and Ara h 2 respectively (Endpoint Chromogenic LAL assay, Lonza, Walkersville, USA). Peptides (Mimotopes, Victoria, Australia and Gen-Script USA Inc, New Jersey, USA) were reconstituted at 1-4 mg/ml in 10% dimethyl sulfoxide/PBS (20-mers and truncated peptide sets) or PBS, 1-2% acetic acid or 0.1M ammonium bicarbonate buffers as specified (custom-synthesized core epitope peptides). All antigens were confirmed to be neither mitogenic nor toxic as described (Eusebius N P et al., *Int Arch Allergy Immunol.* 2002; 127(3):234-44).

Generation of Ara h 1 and Ara h 2-specific CD4+ T-cell lines (TCL): Ara h 1 or Ara h 2-specific oligoclonal TCL were generated from peripheral blood mononuclear cells (PBMC) of peanut-allergic subjects using 5,6-carboxyfluorescein diacetate succinimidylester (CFSE)-based methodology. (Mannering S I et al., *J Immunol Methods.* 2005;298 (1-2):83-92; Prickett S R, et al., *J Allergy Clin Immunol.* 2011; 127(3):608-15 el-5). Briefly, culturing was performed in RPMI-1640 containing 2 mM L-glutamine, 100 IU/mL penicillin-streptomycin and 5% human AB serum (Sigma-Aldrich, St Louis, USA) (cRPMI). PBMC were labelled with 0.1 μM CFSE (Molecular Probes, Eugene, USA) and cultured (2.5×106/mL) with cRPMI alone, CPE (100 μg/mL), Ara h 1 or Ara h 2 (10 μg/mL), Ara h 1 or Ara h 2 20-mer-peptide pools (10 μg/mL/peptide) or as a control, tetanus toxoid (TT; 10 LfU/mL; Statens Serum Institute, Copenhagen, Denmark) for 7 days at 37° C. After staining with CD4-PE and 7AAD (BD Pharmingen, San Diego, USA), CD4+CFSEdim7AAD− cells were sorted (10 cells/well) into 96-U-well plates containing irradiated allogeneic feeder-cells, anti-CD3 (OKT-3), rIL-2 (Cetus, Emeryville, USA) and Fungizone (Invitrogen, Carlsbad, USA) as described. Cells were fed with rIL-2 as required and after 10-14 days, transferred to 48-well plates and tested for proliferation to Ara h 1 or Ara h 2 (10 μg/mL). Ara h 1 or Ara h 2-positive TCL were expanded with anti-CD3 and rIL-2 in T25 culture flasks (BD, Franklin Lakes, USA) for 10-12 days then tested for specificity (proliferation) to overlapping 20-mer peptides spanning the respective sequence (10 μg/mL). Core epitope sequences were mapped within selected 20-mers using peptide sets truncated from the N- or C-terminus of the 20-mer as described (Prickett S R, et alc. *J Allergy Clin Immunol.* 2011; 127(3):608-15 el-5). T-cell assays:All culturing was performed in RPMI-1640 containing 2 mM L-glutamine, 100 IU/mL penicillin-streptomycin and 5% heat-inactivated human AB serum (Sigma-Aldrich, St Louis, USA) (cRPMI). Antigen-induced TCL proliferation was assessed by 3H-thymidine ($^3$H-TdR) uptake assays as follows: assays were performed on 72-hour duplicate or triplicate cultures in 96-U-well plates containing $1×10^4$ T cells/well, $1×10^4$ irradiated (5000 rads) autologous EBV-transformed PBMC (EBV-B cells) as antigen presenting cells and antigens as specified. Negative control was cRPMI alone. Cells were pulsed with $^3$H-thymidine ($^3$H-TdR; 0.5 μCi/well) for the last 16 hours and uptake recorded as mean counts per minute (cpm) of replicate cultures. A stimulation index (SI; cpm antigen-stimulated T cells/cpm unstimulated T cells)≥2.5 was considered positive and all positive responses confirmed in ≥2 assays. To allow detection of peptide-induced CD4+ T-cell proliferation within whole PBMC, 7-day cultures of CFSE-labelled PBMC were set up as described for TCL generation, with addition of anti-CD25 antibodies (BD) to assess T cell activation in addition to proliferation. At least 10,000 CD4+ T cells were analyzed per sample and SI calculated as percentage of CD4+CFSElo (proliferated), CD4+CD25+ (activated) or CD4+CD25+CFSElo (activated and proliferated) cells with antigen divided by the percentage of the same population without antigen (background). Analysing CD4+CD25+CFSElo (activated and proliferated) cells provided the most sensitive method for detection of T cell responses with designation of an SI≥1.5 as positive.

HLA class II blocking assays: T cells and irradiated EBV-B cells ($1×10^4$ of each) were incubated with 0.1-10 μg/mL blocking monoclonal antibody (mAb) against HLA-DR (L243, BD Pharmingen), HLA-DQ (SVP-L3) or HLA-DP (B7/21) or isotype-control antibodies (IgG2a: BD Pharmingen; IgG1: BioLegend, San Diego, USA) for 1 hour at 37° C. prior to addition of peptides (2-10 μg/mL) or CPE (100 μg/mL) and testing proliferative response as above. Cytokine ELISPOT assays: MAW ELISPOT plates (Millipore, Billerica, USA) were coated overnight at 4° C. with 10 μg/mL IL-4, IL-5, IFN-γ or IL-5 antibodies (eBioscience, San Diego, USA) in PBS. Wells were blocked (cRPMI, 1 hour, 37° C.) then PBMC ($3.5×10^5$) or T cells and irradiated EBV-B cells (1×104 of each) added in duplicate 100 μL cultures with CPE (100 μg/mL), nAra h 2 (10 μg/mL) or peptides (10 μg/mL). Controls were cRPMI alone, TT (10 lfU/ml) and phytohaemagglutinin (1 μg/mL; Sigma-Aldrich). After 48 hours culture at 37° C., plates were incubated with biotinylated IL-4, IL-5 or IFN-γ antibodies (eBioscience) (1 μg/ml PBS, 2 hours) followed by ExtrAvidin®-alkaline phosphatase (Sigma-Aldrich) (1/3,000 PBS, 2 hours) before developing with alkaline phosphatase substrate (Bio-Rad). When spots appeared in positive-control wells, plates were washed, air dried and read (AID ELISPOT 4.0 h reader, Autoimmun Diagnostika, Strassberg, Germany).

Basophil activation test: Basophil activation was assessed by CD63 upregulation detected by flow cytometry as described (Drew A C, et al., *J Immunol.* 2004; 173(9):5872-9). Positive controls were rabbit anti-human IgE antibody (7.5 μg/mL; DAKO Corporation, CA, USA), N-formyl-methionine-leucine-phenylalanine (fMLP) (0.4 μg/mL; Sigma) and CPE. CPE was tested over a 3 log concentration range (50, 5 and 0.5 μg/mL) and the peptide pool was tested over a 4-log concentration range (50, 5, 0.5 and 0.05 μg/mL). Histamine release was assessed using Histamine Release and the Histamine ELISA kits (IBL International GmbH, Hamburg, Germany) as per manufacturer's instructions.

Results

The factors considered in dominant 20-mer selection included:

Responder frequency

Number of specific TCL generated per patient/prevalence of specific T cells in patient PBMC Magnitude of T cell response Patterns of T cell responses (peptide combinations recognised within and between subjects)

Ability to directly target specific T cells amongst the whole PBMC population with peptide (CFSE screening)

Consistency of T cell responses

Identification of core T cell epitope(s) within the 20-mer peptide

Ara h 1 Dominant 20-Mer Selection

Figure 18:
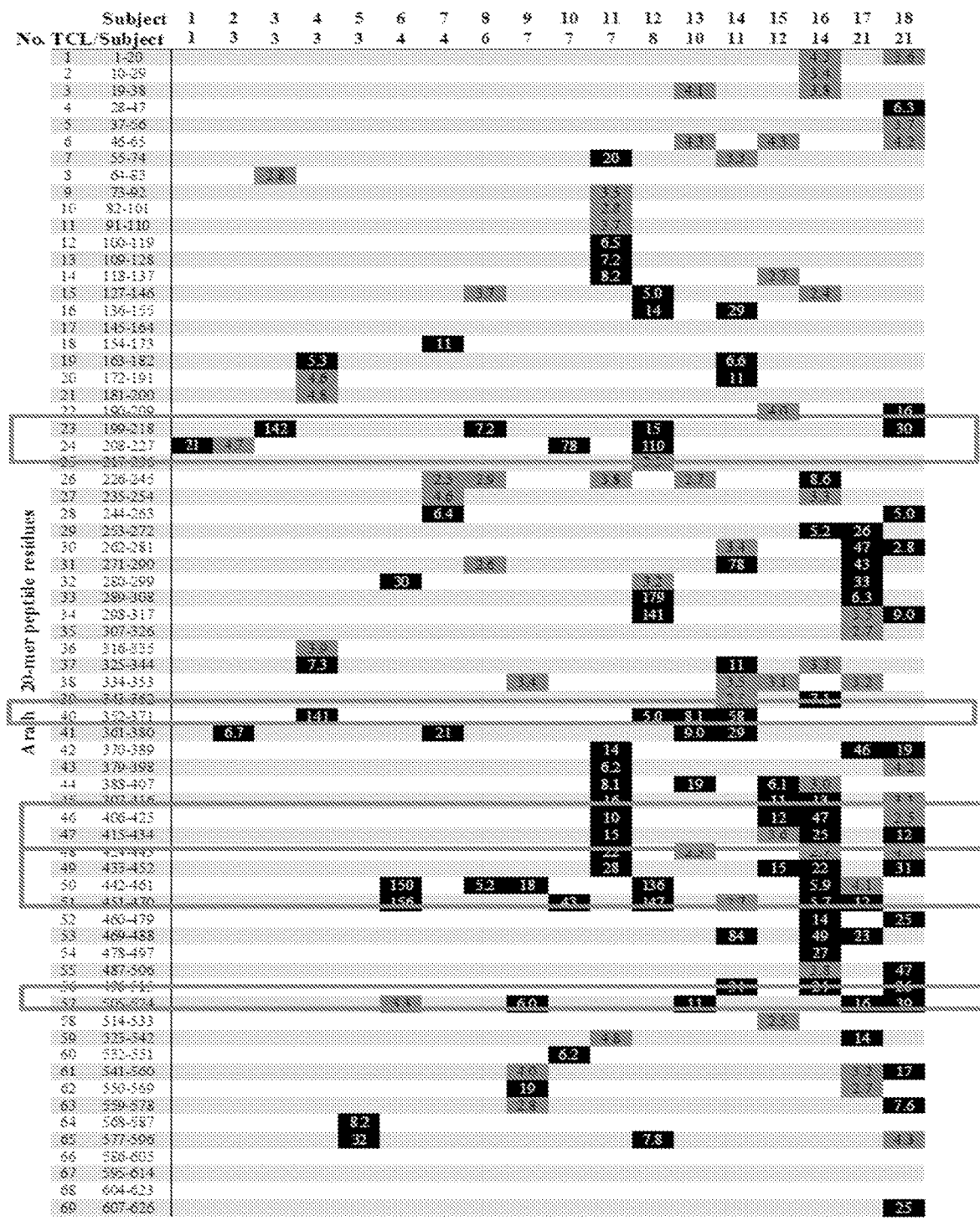
FIG. 18 is a table showing the proliferative responses (thymidine uptake) of TCL to Ara h 1 20-mer peptides. The table shows SI values (=fold increase in TCL proliferation with peptide above proliferation in unstimulated TCL). Only stimulation indices (SI)≥2.5 are shown. For subjects with multiple TCL specific for a given 20-mer, the highest SI is shown. Dark grey, SI≥2.5<5.0; SI≥5.0.

145 Ara h 1-specific T cells lines (TCL) were generated from 18 peanut-allergic donors and 65/69 overlapping 20-mer peptides spanning Ara h 1 were recognised by these TCL (see FIG. 18 and FIG. 5). 14 of these 65 20-mers were selected as most frequently recognised (4-6 responders of 18; 22-33%) (peptide numbers 23, 24, 26, 38, 40, 44-51 and 57). Of these 14 peptides, 9 were selected for further analysis (peptide numbers 23, 24, 40, 46, 47, 49, 50, 51 and 57) (Table 2).

These selections were made based on number of specific TCL per subject, magnitude of TCL response, reproducibility of TCL response and ability to target specific T cells in PBMC. The 9 20-mers which were selected were:
- collectively recognised by TCL from 16 of 18 subjects (89%) in this cohort
- typically induced strong and consistent responses in specific TCL
- each recognised by multiple TCL from many responders
- each able to target specific T cells in donor PBMC (collectively inducing detectible PBMC T cell responses in 18/20 additional subjects with 8-16 responders (40-80%) per 20-mer. One or more of the nine 20-mers was recognised by T cells in 35 (92%) of 38 subjects analysed by TCL isolation and/or CFSE-screening (FIG. 18).

The 9 dominant peptides ultimately selected are shown in Table 2.

TABLE 2

Summary of dominant Ara h 1 20-mer selection

| Peptide No. | Residues | Sequence |
|---|---|---|
| 23 | 199-218 | FDQRSRQFQNLQNHRIVQIE (SEQ ID NO: 45) |
| 24 | 208-227 | NLQNHRIVQIEAKPNTLVLP (SEQ ID NO: 46) |
| 40 | 352-371 | RWSTRSSENNEGVIVKVSKE (SEQ ID NO: 47) |
| 46 | 406-425 | DLSNNFGKLFEVKPDKKNPQ (SEQ ID NO: 48) |
| 47 | 415-434 | FEVKPDKKNPQLQDLDMMLT (SEQ ID NO: 49) |
| 49 | 433-452 | LTCVEIKEGALMLPHFNSKA (SEQ ID NO: 50) |
| 50 | 442-461 | ALMLPHFNSKAMVIVVVNKG (SEQ ID NO: 51) |
| 51 | 451-470 | KAMVIVVVNKGTGNLELVAV (SEQ ID NO: 95) |
| 57 | 505-524 | KEGDVFIMPAAHPVAINASS (SEQ ID NO: 53) |

PBMC Screening with Dominant Ara h 1 20-Mers

FIG. 19 shows that ≥1 dominant 20-mer peptide is recognised by 18/20 (or 22/24 of all data). Each 20-mer peptide is recognised by at least 7 subjects. CFSE and TCL data combined: recognition confirmed in 43/45 subjects.

Ara h 2 Dominant 20-Mer Selection

69 Ara h 2-specific T cells lines (TCL) were generated from 16 peanut-allergic donors and 16/17 overlapping 20-mer peptides spanning Ara h 2 were recognised by these TCL (FIG. 20). 4 of these 16 20-mers were selected as most frequently recognised (each with 7-9 responders of 16; 44-46%) (peptide numbers 4, 5, 11, 15) (FIG. 7). These selections were made based on number of specific TCL per subject, magnitude of TCL response, reproducibility of TCL response and ability to target specific T cells in PBMC. The 4 20-mer peptides which were selected were:

collectively recognised by TCL from all 16 subjects (100%) in this cohort typically induced strong and consistent responses in specific TCL each recognised by multiple TCL from many responders collectively recognised by ~80% of all 69 TCL each able to target specific T cells in donor PBMC (detectible PBMC T cell responses demonstrated in 6 subjects tested).

One or more of the four 20-mers was recognised by T cells in 16/16 (100%) of subjects analysed by TCL isolation and/or CFSE-screening (FIG. 20).

The dominant 20-mers are indicated in Table 3.

TABLE 3

Summary of dominant Ara h 2 20-mer selection

| Name | Residues | Sequence |
|---|---|---|
| 20-mer 4 | 28-47 | RRCQSQLERANLRPCEQHLM (SEQ ID NO: 54) |
| 20-mer 5 | 37-56 | ANLRPCEQHLMQKIQRDEDS (SEQ ID NO: 55) |
| 20-mer 11 | 91-110 | ELNEFENNQRCMCEALQQIM (SEQ ID NO: 56) |
| 20-mer 15 | 127-146 | KRELRNLPQQCGLRAPQRCD (SEQ ID NO: 57) |

Core T-Cell Epitope Mapping

Technical Approach

TCL from different subjects were used to map each core T cell epitope. Exact T cell epitopes varied between TCL and subjects. The minimum T-cell stimulatory sequence (core epitope) within each selected 20-mer was determined by testing proliferation of reactive TCL from different subjects to truncated peptide sets (FIG. 8). The number of residues required to induce maximal T-cell proliferation varied from 6-19 aa between different TCL and/or subjects (FIGS. 21 and 22). Due to variation in the number of flanking-residues required for optimal epitope recognition, TCL were considered to recognize the same epitope if peptides containing a common core sequence induced recognition. Based on this criterion, ten distinct Ara h 1 and 5 distinct Ara h 2 $CD4^+$ T-cell epitopes were identified ('consolidated epitopes', FIGS. 21 and 22), with common 'minimal core epitope' sequences varying from 5-12 aa (underlined sequences, FIGS. 21 and 22). 'Consolidated epitope' sequences were the minimum sequences encompassing all residues required for optimal T cell reactivity across different subjects to ensure broadest possible recognition.

(i) Core T Cell Epitopes Found in Dominant Ara h 1 20-Mers

Core T-cell epitope sequences were mapped within the dominant Ara h 1 20-mer peptides. 10 Ara h 1 T cell epitopes were identified ('consolidated T cell epitope'), including 4 pairs of overlapping T cell epitopes. (FIG. 21)

(ii) Core T Cell Epitopes Found in Dominant Ara h 2 20-Mers

Core T-cell epitope sequences were mapped within dominant Ara h 2 20-mer peptides. 5 Ara h 2 T cell epitopes were identified ('consolidated T cell epitopes'), including 2 pairs of overlapping T cell epitopes (FIG. 22)

HLA-Restriction of Ara h 1 and Ara h 2 T Cell Epitopes

Figure 9:
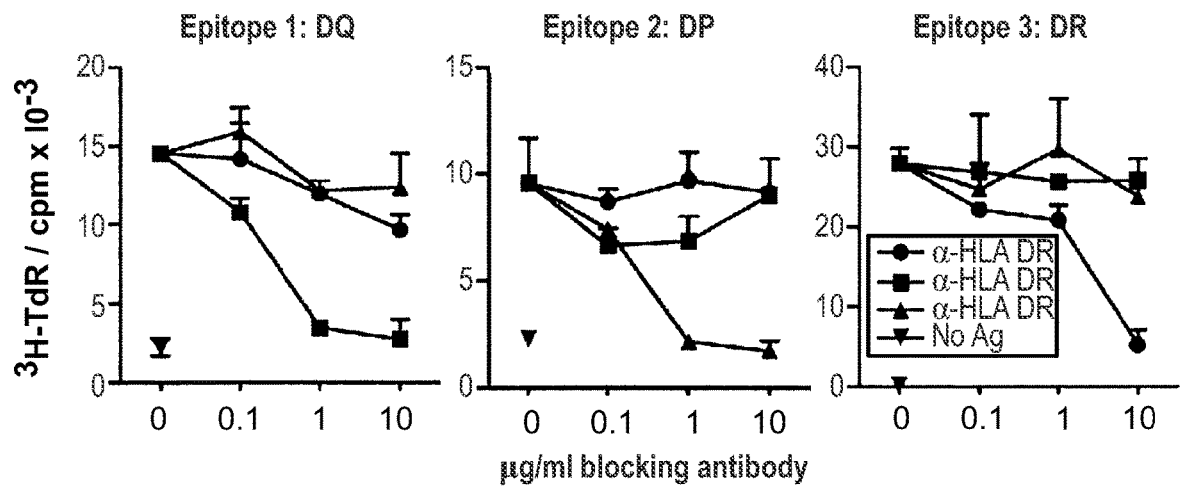
FIG. 9 is a graphical representation of the HLA restriction of the dominant Ara h 1 and Ara h 2 T cell epitopes.

T cell recognition of dominant T cell epitopes was blocked with monoclonal antibodies against HLA-DP, HLA-DQ or HLA-DR (FIG. 9). Some T cell epitopes presented on both HLA-DR and HLA-DQ molecules while the T cell epitopes were collectively presented on HLA-DP, HLA-DQ and HLA-DR (Table 4).

cell epitope must be presented by multiple HLA-DQB1 molecules. Similarly, the diversity in HLA-DRB1 alleles between subjects for whom recognition of Ara h 2 T cell epitopes (127-141) or (37-47) was blocked by anti-HLA-DR indicated binding-degeneracy of both T-cell epitopes for multiple HLA-DRB1 molecules.

In addition to presentation by at least 2 HLA-DR molecules, Ara h 2 T cell epitope (37-47) was also presented by HLA-DQB1*06:09 as both subjects who recognised this T

TABLE 4

| Peptide info | T cell Epitope Sequence | Residues | length | HLA-restriction |
|---|---|---|---|---|
| Ara h 1 dominant T cell epitopes | | | | |
| 23 core | FQNLQNHRIV (SEQ ID NO: 21) | 206-215 | 10 aa | HLA-DR |
| 24 core | RIVQIEAKPNTLV (SEQ ID NO: 22) | 213-225 | 13 aa | HLA-DR |
| 40 core | WSTRSSENNEGVIVKVSKE (SEQ ID NO: 59) | 353-371 | 19 aa | HLA-DQ |
| 46 core | NNFGKLFEVKPDKKNPQ (SEQ ID NO: 34) | 409-425 | 17 aa | HLA-DR |
| 47 core | EVKPDKKNPQLQ (SEQ ID NO: 4) | 416-427 | 12 aa | HLA-DR |
| core 49 | VEIKEGALMLPHFNSKA (SEQ ID NO: 13) | 436-452 | 17 aa | HLA-DQ |
| 50 core | ALMLPHFNSKAMVIVVV (SEQ ID NO: 33) | 442-458 | 17 aa | HLA-DR |
| 50/51 core | KAMVIVVVNKG (SEQ ID NO: 42) | 451-461 | 11 aa | HLA-DR |
| 51 'core' | KAMVIVVVNKGTGNLELVAV (SEQ ID NO: 95) | 451-470 | 20 aa | HLA-DR |
| 57 core | GDVFIMPAAHPVAINASS (SEQ ID NO: 29) | 507-525 | 19 aa | HLA-DR or HLA-DQ |
| Ara h 2 dominant T cell epitopes | | | | |
| 4 core | SQLERANLRPCEQ (SEQ ID NO: 77) | 32-44 | 13 aa | HLA-DP |
| 4/5 core | ANLRPCEQHLM (SEQ ID NO: 82) | 37-47 | 11 aa | HLA-DR or HLA-DQ |
| 10 core | ELNEFENNQRCM (SEQ ID NO: 84) | 91-102 | 12 aa | HLA-DR |
| 10/11 core | EFENNQRCMCEALQ (SEQ ID NO: 86) | 94-107 | 14 aa | HLA-DQ |
| 15 core | RELRNLPQQCGLRA (SEQ ID NO: 94) | 128-141 | 14 aa | HLA-DR |

HLA-Restriction of Ara h 1 and Ara h 2 T Cell Epitope Presentation

HLA-typing was performed on subjects, with TCL recognising dominant T cell epitopes, in order to assess HLA-subtypes potentially able to T cell present epitopes. The absence of shared HLA alleles for subjects recognising a T cell epitope with confirmed HLA-DR/DQ/DP restriction indicated T cell epitope HLA-binding degeneracy. The Ara h 1 results are shown in FIG. 23 and the Ara h 2 results in FIG. 24.

The absence of a shared HLA-DQB1 allele between all subjects from whom recognition of Ara h 2 T cell epitope (95-107) was blocked by anti-HLA-DQ indicated that this T cell epitope in the context of HLA-DQ had this allele, and for subject 9 it was the only DQB1 allele present.

As DPB1*04:01 or DRB1*15:01 alleles were present in all subjects recognising Ara h 2 T cell epitopes (32-44) (blocked by anti-HLA-DP) or (95-107) (blocked by anti-HLA-DR) respectively, degeneracy of these T cell epitopes could not be determined. However, as DPB1*0401 and DRB1*1501 are prevalent in populations worldwide, T cell epitopes presented by these HLA-molecules would still be broadly recognized.

There were no shared alleles between two or more subjects recognising the dominant consolidated Ara h 1 T cell epitopes on a given HLA-type, thus demonstrating that each of the identified Ara h 1 T cell epitopes was also presented by 2 or more different HLA-molecules.

Predicting HLA-Binding Motifs: Ara h 1 20-Mer Peptides

Figure 25:
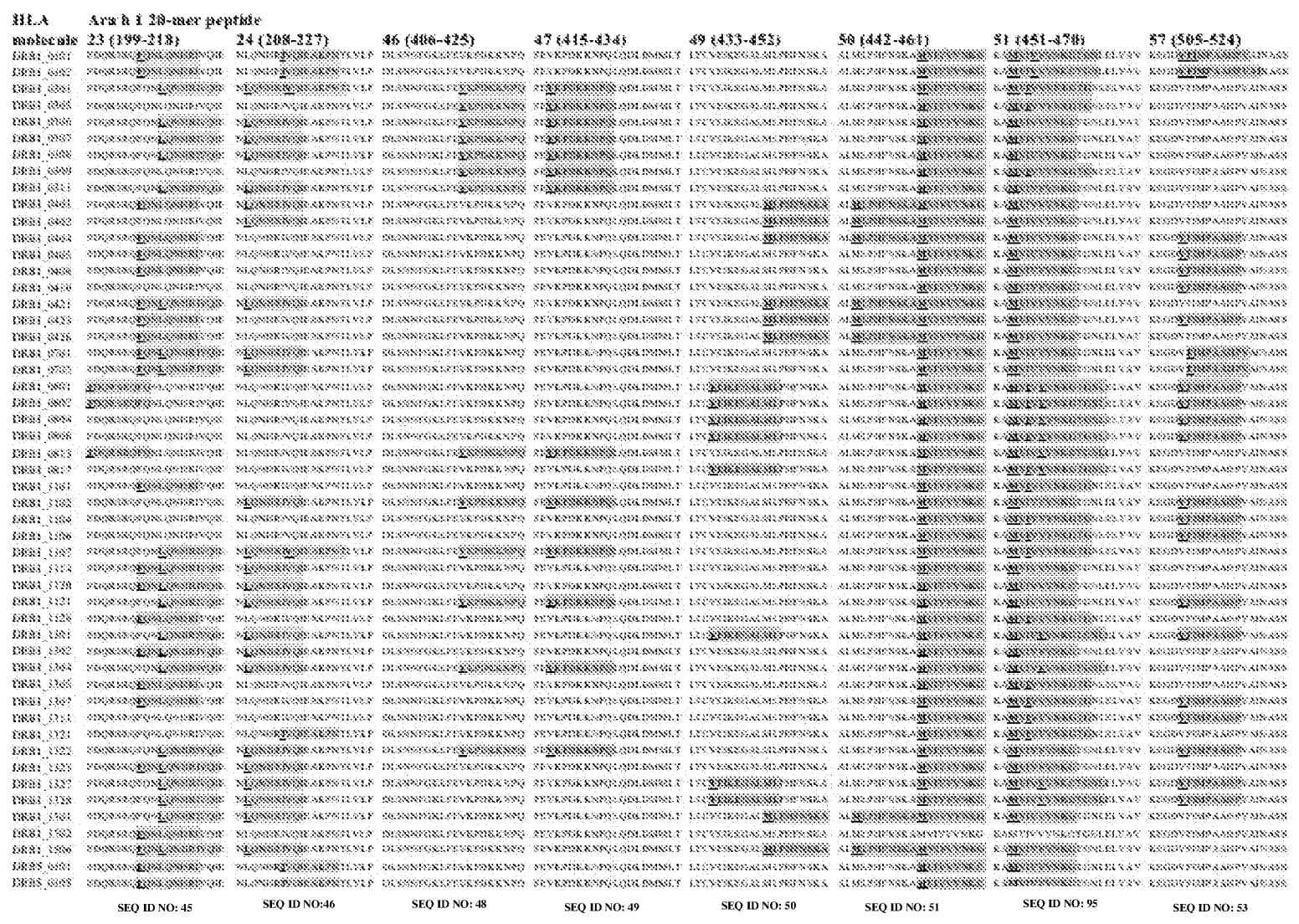

FIG. 25 provides a results summary for an HLA-DR prediction algorithm for binding motifs within dominant Ara h 1 20-mers.

Predicting HLA-Binding Motifs: Ara h 2 20-Mer Peptides

Table 5 provides a results summary for 2 HLA-DR prediction algorithms for binding motifs within 3 dominant Ara h 2 20-mers (NB dominant '20-mer 5' not shown as predicted and actual epitopes fall in overlap with '20-mer 4').

TABLE 5

| 20-mer name | Sequence | Residues |
|---|---|---|
| Ara h 2 pep 4 | RRCQSQLERANLRPCEQHLM (SEQ ID NO: 54) | 28-47 |
| Ara h 2 pep 11 | ELNEFENNQRCMCEALQQIM (SEQ ID NO: 56) | 91-110 |
| Ara h 2 pep 15 | KRELRNLPQQCGLRAPQRCD (SEQ ID NO: 57) | 127-146 |

Refining Peptides for Therapeutic Delivery

Figure 10:
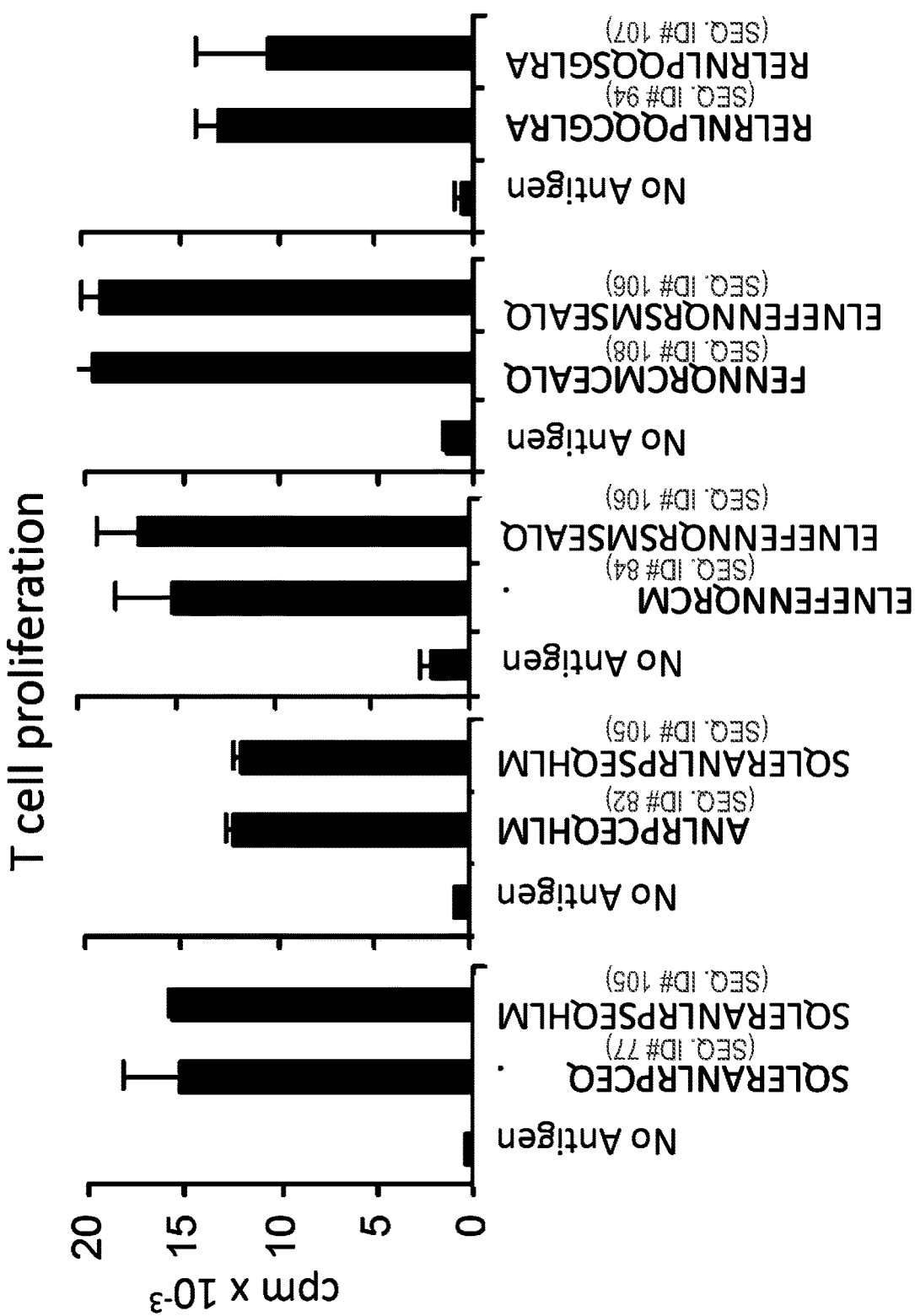
FIG. 10 is a graphical representation of T cell recognition of peptides in which selected cysteine residues were replaced with serine residues. TCL proliferation in response to 'parent' (cysteine containing) or serine-substituted Ara h 2 peptides as determined by $^3$H thymidine uptake. Graphs show representative TCL for each epitope (mean cpm replicate wells+SD). A) Ara h 2(32-44), B) Ara h 2(37-47); C) Ara h 2(91-102); D) Ara h 2(95-107); E) Ara h 2(128-141).
Figure 11:
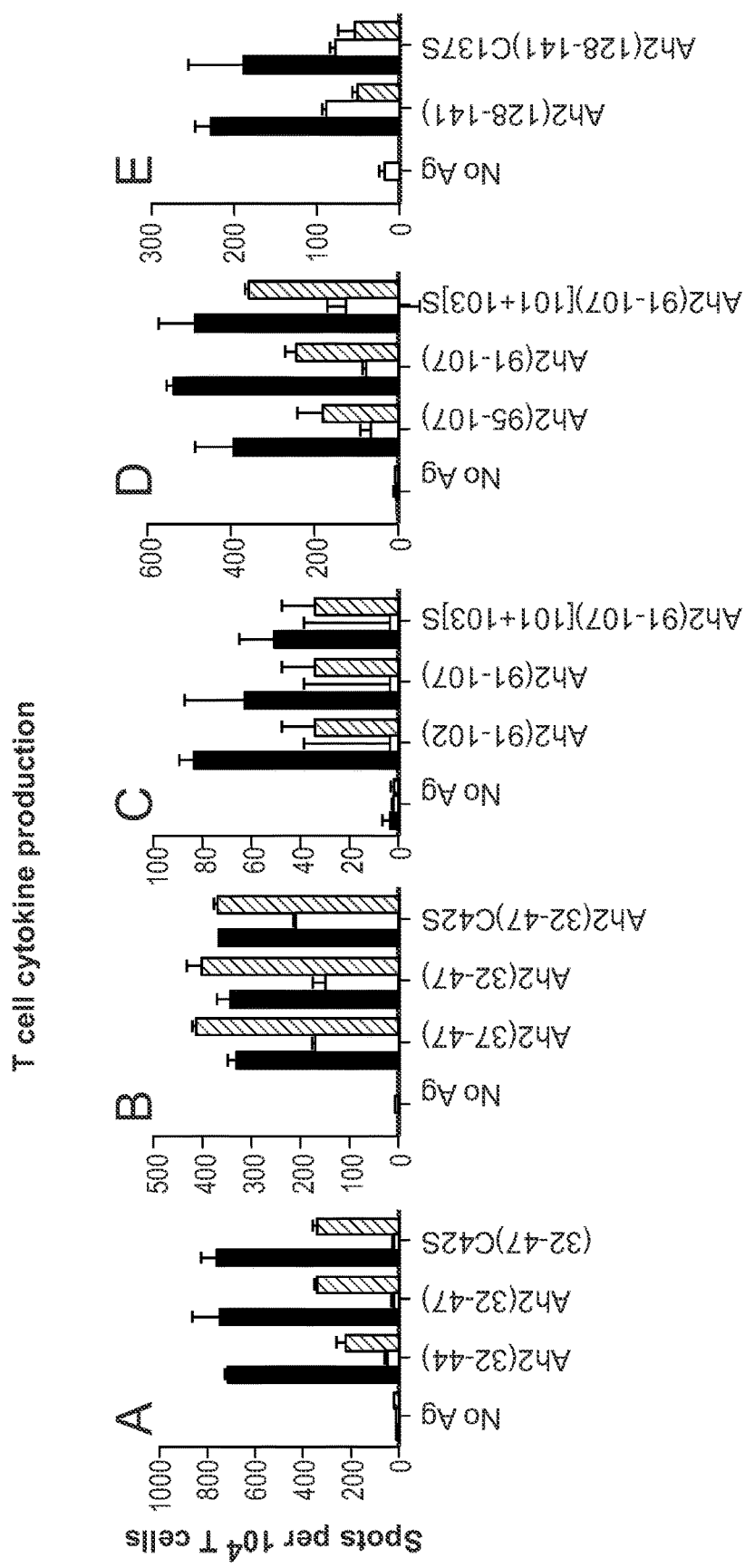
FIG. 11 is a graphical representation of T cell cytokine production in response to peptides in which selected cysteine residues were replaced with serine residues. Cytokine secretion in response to 'parent' or cysteine-substitute Ara h 2 peptides determined by ELISPOT. Graphs show representative TCL specific for each epitope (means spots of replicate wells+SD). IL-4, black bars; IL-5, hatched bars; IFN-γ, white bars; A) Ara h 2(32-44), B) Ara h 2(37-47); C) Ara h 2(91-102); D) Ara h 2(95-107); E) Ara h 2(128-141).

Potentially problematic cysteine residues were replaced with structurally conserved, but less chemically reactive serine residues. Retained T cell reactivity was confirmed (FIGS. 10 and 11). Serine-containing T cell epitope peptides showed comparable T cell responses to native cysteine-containing peptides.

Combining Overlapping Ara h 2 T Cell Epitopes into Single Peptides≤20 Aa Long

TABLE 6

| Dominant 20-mers | | Core Epitopes | | Candidate Peptides | |
|---|---|---|---|---|---|
| Residues | Sequence | Residues | Sequence | Residues | Sequence |
| 28-47 | RRCQSQLERANLRPCEQHLM (SEQ ID NO: 54) | 32-44 | SQLERANLRPCEQ (SEQ ID NO: 77) | 32-47 C42S | SQLERANLRPSEQHLM (SEQ ID NO: 105) |
| | | 37-47 | ANLRPCEQHLM (SEQ ID NO: 82) | | |
| 82-101 | SQHQERCCNELNEFENNQRC (SEQ ID NO: 104) | 91-102 | ELNEFENNQRCM (SEQ ID NO: 84) | 91-107 C[101 + 103]S | ELNEFENNQRSMSEALQ (SEQ ID NO: 106) |
| 91-110 | ELNEFENNQRCMCEALQQIM (SEQ ID NO: 56) | 95-107 | EFENNQRCMCEALQ (SEQ ID NO: 86) | | |
| 127-146 | KRELRNLPQQCGLRAPQRCD (SEQ ID NO: 57) | 128-141 | RELRNLPQQCGLRA (SEQ ID NO: 94) | 128-141 C137S | RELRNLPQQSGLRA (SEQ ID NO: 107) |

Ara h 1 and Ara h 2 Candidate Peptides Summarised

There are 10 candidate peptides: 7 from Ara h 1 and 3 from Ara h 2 (Table 7)

TABLE 7

| Peptide info | Sequence | Residues | length | HLA-restriction |
|---|---|---|---|---|
| *Ara h 1 dominant T cell epitopes* | | | | |
| 23 + 24 core | FQNLQNHRIVQIEAKPNTLV (SEQ ID NO: 11) | 206-225 | 20 aa | HLA-DR |
| 40 core | WSTRSSENNEGVIVKVSKE (SEQ ID NO: 59) | 353-371 | 19 aa | HLA-DQ |
| 46 + 47 core | NNFGKLFEVKPDKKNPQLQ (SEQ ID NO: 17) | 409-427 | 19 aa | HLA-DR |
| core 49 | VEIKEGALMLPHFNSKA (SEQ ID NO: 13) | 436-452 | 17 aa | HLA-DQ |
| 50 core | ALMLPHFNSKAMVIVV (SEQ ID NO: 33) | 442-458 | 17 aa | HLA-DR |
| 51 'core' | KAMVIVVVNKGTGNLELVAV (SEQ ID NO: 40) | 451-470 | 20 aa | HLA-DR |
| 57 core | GDVFIMPAAHPVAINASS (SEQ ID NO: 29) | 507-525 | 19 aa | HLA-DR or HLA-DQ |
| *Ara h 2 dominant T cell epitopes* | | | | |
| 4 + 4/5 core | SQLERANLRPSEQHLM (SEQ ID NO: 105) | 32-47 C42S | 16 aa | HLA-DP, -DQ or DP |

TABLE 7-continued

| Peptide info | Sequence | Residues | length | HLA-restriction |
|---|---|---|---|---|
| 10 + 10/11 core | ELNEFENNQRSMSEALQ (SEQ ID NO: 106) | 91-107 C[101 + 103]S | 17 aa | HLA-DR or -DQ |
| 15 core | RELRNLPQQSGLRA (SEQ ID NO: 107) | 128-141 | 14 aa | HLA-DR |

Also designed are 13 additional shorter peptide variants (based on single T cell epitopes) for comparison. Some sequences have been lengthened or shortened (in line with native sequences and critical residues for T cell recognition) to improve peptide properties for production and solubility. This resulted in a panel of 23 candidate peptides for comparison. Peptide details are summarised in FIG. 28.

All of the peptides in Table 7 were produced at 95-99.9% purity and solutions determined for solubility. T cell responses were then compared to each of these peptides at 2 doses in PBMC from 25 peanut-allergic subjects in order to select a final therapeutic combination.

NB Buffers: all peptides tried in PBS first; then 0.1M NH4HCO3 if sequence suggested preference for high pH, or 1% acetic acid for low pH; if not soluble in 1% acetic acid, increased to 2, 5, 10% etc.

N-terminal 'W' omitted from 'peptide 2 to improve stability and ease of synthesis
C-terminal 'E' added to 'peptide 7 to improve solubility (otherwise peptide insoluble except in toxic buffers)

Considerations for Selecting Final Peptides
Aims:
Maximise population coverage and/or T cell reactivity whilst minimising sequence number and/or length.
Broad Considerations for Peptide Selection:
Comparison of T cell responses in 23-peptide screen
Prior T cell reactivity data (for individual T cell epitopes/peptides)
Sequence (ease of production/solubility)
HLA-restriction (most degenerate and HLA-DQ-restricted T cell epitopes)
Considerations for Selection Based on Data from 23-Peptide Screen:
Main assessment criteria based on SI values for CD25+ CFSE-low cells
Donor responder frequency per peptide at one or both concentrations
Compare responses to long versus short variants
Strength/consistency of responses (i.e. those subjects who respond to both concentrations vs those who respond to just one concentration)

Figure 29:
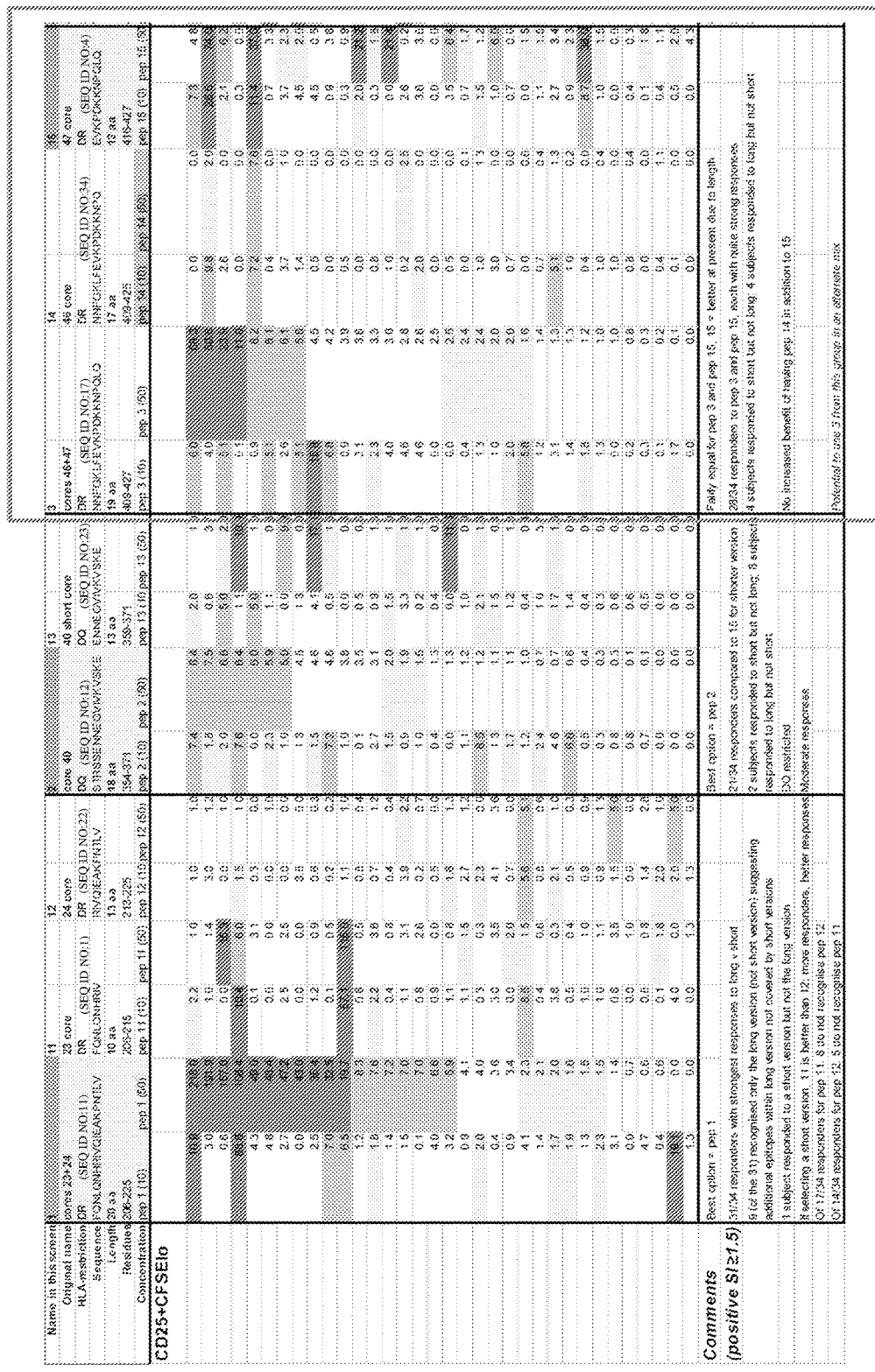
FIG. 29 is a table showing a summary of responses to 23-peptide panel in expanded cohort of 34. Dark grey boxes indicate groups with feasible alternate peptides to add/substitute into current pool. The data indicate that the selected 7 peptides are the best combination, but boxes indicate groups containing other viable peptides as substitutions (or additions) to the current pool: For example: 1) Peptide 3 could replace peptide 15; 2) Peptide 8 could replace peptide 21; 3) Peptide 9 could replace peptide 23.
Figure 29:
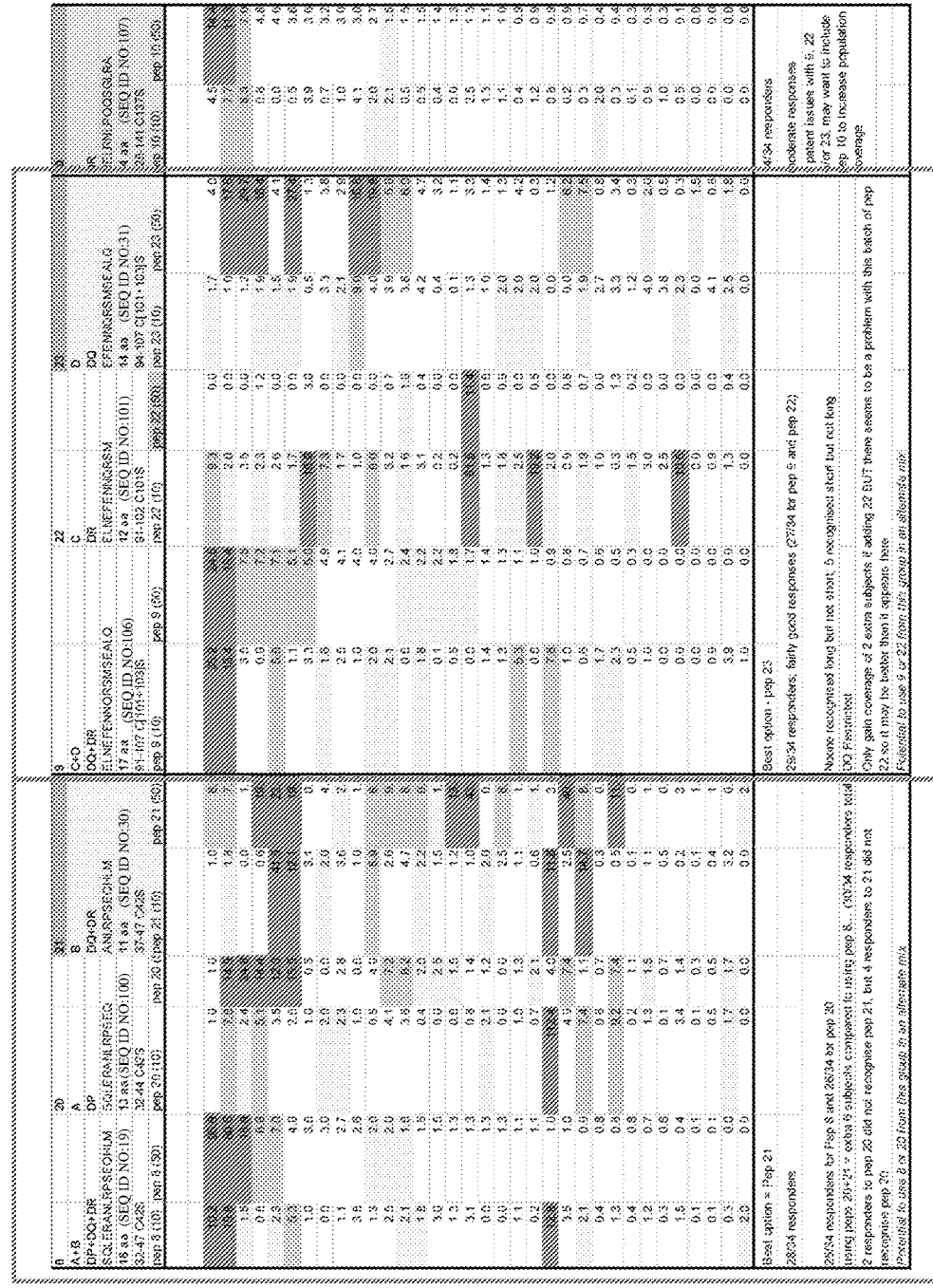

Patterns of responses
FIG. 29 shows the analysis of PBMC T cell responses to the full set of 23 candidate peptides in 34 peanut-allergic subjects. These data show SI values for % CD25+CFSElow CD4+ T cells with peptide/unstimulated.

Data are grouped into a long and short version of each T cell epitope-containing region (see column borders; e.g. 1$^{st}$ 'group'=peptides 1, 23 and 24 [Pep 1 combines overlapping peps 23 and 24 which each contain a separate T cell epitope]). The summary at the bottom of each group comments on the optimal peptide selected from that group. (Data show SI values for % CD25+CFSElow CD4+ T cells with peptide/unstimulated).

Data are sorted by descending value for 50 μg sample of long version for each peptide 'group' (or 10 μg sample where responses are better to this dose). Each row within in a peptide group shows data for a single subject, but the order of subjects varies in each peptide group.

Summary of Responses to 23-Peptide Panel in Cohort of 34
The data indicate that the selected 7 peptides are the best combination, but boxes indicate groups containing other viable peptides as substitutions (or additions) to the current pool:
For example:
1) Peptide 3 could replace peptide 15
2) Peptide 8 could replace peptide 21
3) Peptide 9 could replace peptide 23

Summary of Responses to Each Peptide of 7-Peptide Mix in Cohort of 39
All recognised 1 or more peptides
13/39 (33%) recognise 100% of peptides
21/39 (54%) recognise>85% (6 or more) peptides
31/39 (79%) recognise>70% (5 or more) peptides
Each peptide recognised by at least 25/39 subjects (64%)
Of the 74 subjects tested, all reacted to at least 1 peptide of the 7 selected peptides.

Figure 28:
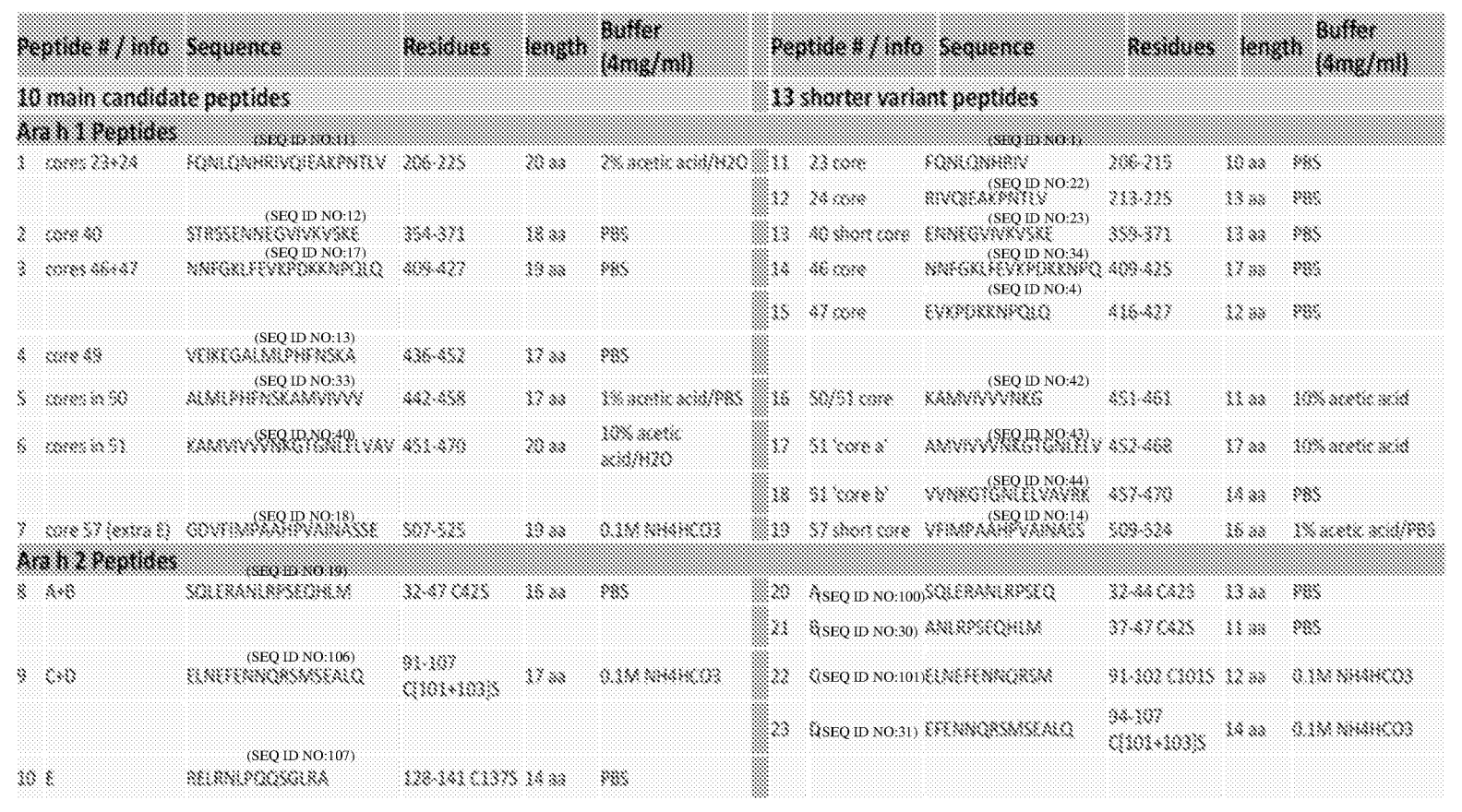

Responses to Different Peptide Pools
NB: FIG. 28 provides the sequences for each of peptides 1-23.
Pool 1=7×original Ara h 1 'candidates'
Pool 2=3×original Ara h 2 'candidates'
Pool 3=10×mix of above 2 pools (Ara h 1 & 2)
Pool 4=3×Ara h 1 'candidates'+5×shorter variants (equivalent Ara h 1 sequence coverage to pool 1)
Pool 5=5×shorter (single epitope) variants of Ara h 2 candidates (equivalent Ara h 2 sequence coverage to pool 2)

TABLE 8

Refined peptide pool
Peptide Vax

| Original name | # | HLA | Sequence | Residues | aa | Notes |
|---|---|---|---|---|---|---|
| Cores 23 + 24 | 1 | DR | FQNLQNHRIVQIEAKPNTLV (SEQ ID NO: 11) | Ara h 1 [206-225] | 20 | Contains 2 major Ara h 1 epitopes Present in Ara h 1 T cell patent |

TABLE 8-continued

Refined peptide pool
Peptide Vax

| Original name | # HLA | Sequence | Residues | aa | Notes |
|---|---|---|---|---|---|
| Core 40 | 2 DQ | STRSSENNEGVINKVSKE (SEQ ID NO: 12) | Ara h 1 [354-371] | 18 | *key sequence flagged in Ara h 1 patent, but one residue shorter to facilitate stability; contains one major Ara h 1 T cell epitope |
| Core 47 | 15 DR | EVKPDKKNPQLQ (SEQ ID NO: 4) | Ara h 1 [416-427] | 12 | Shortened version of a candidate peptide in Ara h 1 patent; contains 1 Ara h 1 T cell epitope Induced equivalent T cell responses to longer version containing an additional T cell epitope in screen of 25 new subjects |
| Core 49 | 4 DR/DQ | VEIKEGALMLPHFNSKA (SEQ ID NO: 13) | Ara h 1 [436-452] | 17 | *key sequence flagged in Ara h 1 patent |
| Core 57 (short) | 19 DR/DQ | VFIMPAAHPVAINASS (SEQ ID NO: 14) | Ara h 1 [509-524] | 16 | *shortened version of key sequence flagged in Ara h 1 patent; Easier to produce and more soluble Induced equivalent T cell responses to longer version containing an additional epitope in screen of 25 new subjects |
| B | 21 DR/DQ | ANLRPSEQHLM (SEQ ID NO: 30) | Ara h 2 [37-47] C42S | 11 | Induced equivalent T cell responses to longer vemion containing an additional T cell epitope in screen of 25 new subjects |
| D | 23 DQ | EFENNQRSMSEALQ (SEQ ID NO: 31) | Ara h 2 [94-107] C[101 + 103]S | 14 | Induced equivalent T cell responses to longer version containing an additional T cell epitope in screen of 25 new subjects; One residue longer than core T cell epitope reported in Ara h 2 paper. |

Pool 7a=5×Ara h 1+3×Ara h 2 for 'refined' pool (same as final pool but with additional Ara h 2 T cell epitope)
Pool 7b=5×Ara h 1+3×Ara h 2 for 'refined' pool of 7
Basophil Responses to 7-Peptide Pool (Pool 7b)

Figure 2A:
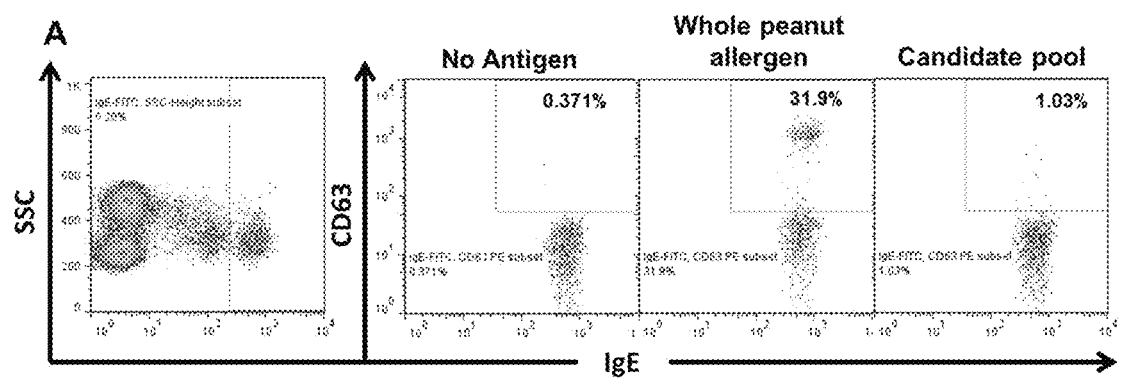
FIGS. 2A-2C are graphical representations of a basophil activation test (BAT) (FIG. 2A) FACS plots showing blood from a peanut-allergic subject incubated with whole peanut extract or the Vax (7 peptide compilation). Basophils are identified as IgEhi cells (box, first plot) and activated basophils as CD63hi (boxes, plots 2-4).
Figure 2B:
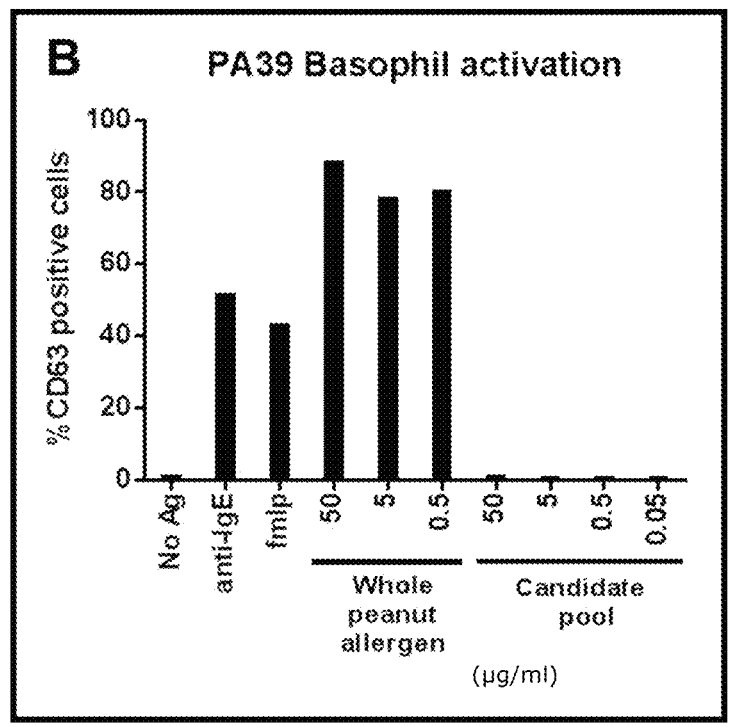
Figure 2C:
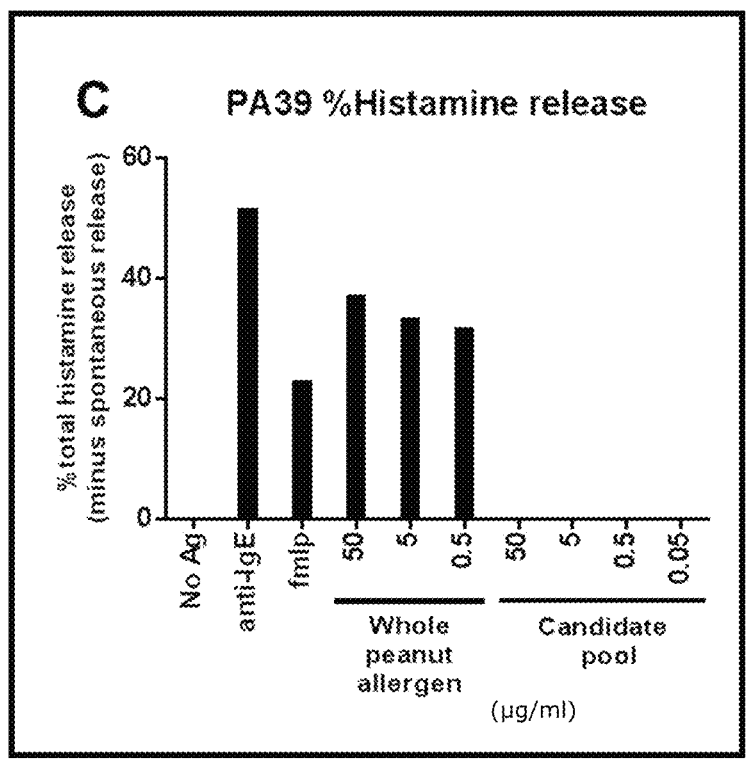

Basophil reactivity data was collected from 14 peanut-allergic subjects following incubation with peanut (CPE) or the 7-peptide pool (pool 7b) over a 3-4 log concentration range (m/ml)(FIG. 2). In these subjects, basophil activation and histamine release was induced by whole peanut and positive controls, but not by the 7-peptide mixture.

Prior to selection of pools 7a and 7b. Pools 7a and 7b were subsequently designed and tested.

PBMC T cell responses were compared to whole peanut and peptide pools 1-5 of FIG. 32. (FIGS. 12 and 13). In relation to pools 1-5, none of the pools were able to induce a positive T cell response in all subjects tested. Nearly all responses were considerably lower to the peptide pool than to whole peanut (at the concentrations tested) and only one subject of each of pools 2, 3 and 4 showed a greater or equal response to the peptides as to whole peanut. In relation to pools 7a and 7b, 100% response was described to pools 7a and 7b (SI>1.5). Pools 7a and 7b induced comparable or greater responses to whole peanut in many subjects 6/30=≥100 CPE response, 6/30=50-80% of CPE response.

When comparing PBMC T cell responses to the 7-peptide pool (FIG. 14), there was no significant difference between pools 7a and 7b (comparing paired data; n=15 per group; no advantage adding 3rd Ara h 2 peptide). There was still no significant difference when comparing full data set for pool 7b (n=30) with cohort for pool 7a using non-paired Mann Whitney test for non-parametric data; p=0.9).

In summary, pools 7a and 7b were both significantly better than the other 5 pools tested. There was no significant difference in pool 7a over pool 7b. Pool 7b was recognised by 100% of subjects tested and induced comparable or greater PBMC T cell responses than peanut in over 33% of subjects. Pools 1-5 were not recognised by 100% of subjects and very rarely induced responses equal to whole peanut.

TABLE 9

More detailed summary of steps and data

| Approach | Results |
|---|---|
| 1) Identification of dominant T cell epitopes of major peanut allergens Ara h 1 and Ara h 2 | |
| Isolated CD4+ T cells specific for Ara h 1 or Ara h 2 from PBMC of peanut-allergic subjects | 145 Ara h 1-specific T cell lines (TCL) (18 subjects)<br>69 Ara h 2-specific TCL (16 subjects)<br>Total = 214 TCL from 20 subjects |
| Determined specificity to overlapping 20-mer peptides spanning whole Ara h 1 or 2 sequence & selected dominant 20-mers | 9 (of 69) dominant Ara h 1 20-mers<br>4 (of 17) dominant Ara h 2 20-mers |
| Confirmed dominant 20-mers could target PBMC T cells in peanut-allergic subjects (CFSE screens) | 1 Ara h 1 20-mer detected in 17/19<br>1 Ara h 2 20-mer detected in 6/6 |
| Assessed total frequency of responders (combined data from TCL data and CFSE screens) | 1 dominant Ara h 1 20-mer recognised by 43/45. 1 dominant Ara h 2 20-mer recognised by 16/16 |
| Mapped core T cell epitope sequences within dominant 20-mers | 10 dominant Ara h 1 core T cell epitopes<br>5 dominant Ara h 2 core T cell epitopes |
| 2) Determining HLA-restriction of core T cell epitopes | |
| Blocked T cell epitope presentation to specific TCL using anti-HLA antibodies | Ara h 1 T cell epitopes HLA-DR &/or -DQ restricted |
| HLA-genotyped subjects used for TCL generation | Ara h 2 T cell epitopes HLA-DR, -DQ &or -DP restricted<br>All T cell epitopes presented by 1 HLA-molecule |
| Assessed HLA-binding degeneracy with algorithms | Strong & degenerate binding motifs in all T cell epitopes |
| 3) Design of therapeutic candidate peptides | |
| Replaced cysteine residues with serine residues | All serine variants still T cell reactive |
| Combined overlapping T cell epitopes into peptides 20 aa long | 7 candidate Ara h 1 peptides (Prickett et al 2013) |
| Designed shorter variants with single T cell epitopes | 3 candidate Ara h 2 peptides (Prickett et al 2011)<br>13 shorter variants of above candidate peptides |
| Synthesised all 23 peptides to GLP-grade purity. Determined suitable solutions for solubility. | All peptides obtained at 95-99.9% purity<br>22/23 peptides soluble in PBS, 0.1M NH4HCO3, or 1-2% acetic acid (1 insoluble peptide redesigned and new version now soluble; peptide 7 in Table 18) |
| 4) Selection and testing of final therapeutic mixture | |
| Compared PBMC T cell reactivity to all 23 peptides (2 doses) in new peanut-allergic cohort | 34 subjects screened with all 23 peptides<br>Optimal peptide combinations determined |
| Peptides selected for final therapeutic (considered T cell responses, peptide properties, responder frequency, HLA-restriction, patents) | 7 peptides selected (5xAra h 1 and 2xAra h 2)<br>Presented on HLA-DR (5/7) and/or HLA-DQ (5/7)<br>1-7 of peptides recognised by 56/56 donors |
| Assessed PBMC T cell response to 7-peptide mix at 2 therapeutic doses in peanut-allergic cohort | T cell response seen its 24/25 subjects (often comparable or greater than response to peanut) |

Example 3

Figure 15:
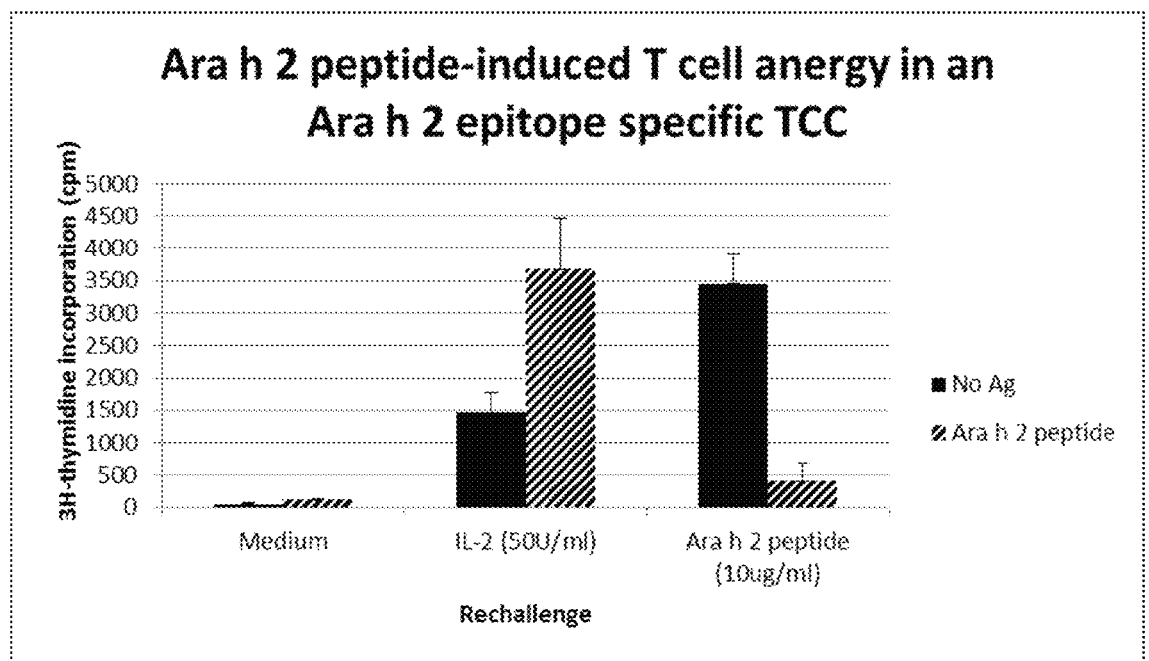
FIG. 15 is a graphical representation of Ara h 2 peptide-induced inhibition of T cell proliferation.

Ara h 2 Peptide-Induced T Cell Anergy in an Ara h 2 Epitope Specific TCC (FIG. 15)

T cells (1×10$^6$/ml) of an Ara h 2 peptide specific human T cell clone were cultured for 16 hours in the presence of Ara h 2 peptide (ANLRPSEQHLM (SEQ ID NO:30; hatched) at 100 µg/ml in the absence of accessory cells or in complete medium* alone (No Ag). The T cells were then washed thoroughly and rechallenged (10$^4$/well) with complete medium alone, IL-2 50 U/ml or an immunogenic concentration of the Ara h 2 peptide (10 µg/ml) in the presence of irradiated autologous PBMC (10$^5$/well) as accessory cells. Proliferation as correlated with tritiated thymidine incorporation was determined at 72 hours. Results are expressed as mean cpm+SD for triplicate cultures. *Complete medium: RPMI+5% AB serum+Pen/Strep/L-glutamine+10 U/mL of IL-2.

Figure 16:
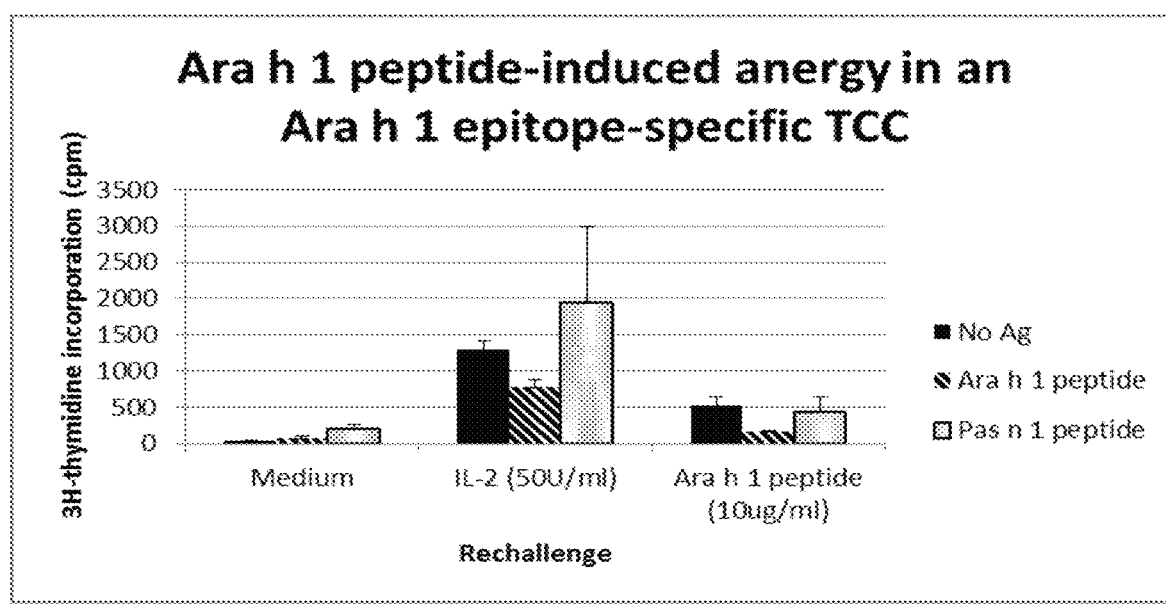
FIG. 16 is a graphical representation of Ara h 1 peptide-induced inhibition of T cell proliferation.

Ara h 1 Peptide-Induced Anergy in an Ara h 1 Epitope-Specific TCC (FIG. 16)

T cells (1×10$^6$/ml) of an Ara h 1 peptide specific human T cell clone were cultured for 16 hours in the presence of Ara h I peptide (STRSSENNEGVIVKVSKE (SEQ ID NO:12; hatched) or an irrelevant Bahia grass Pas n 1 peptide (stippled) at 100 µg/ml in the absence of accessory cells or in complete medium* alone (No Ag). The T cells were then washed thoroughly and rechallenged (10$^4$/well) with complete medium alone, IL-2 50 U/ml or an immunogenic concentration of the Ara h I peptide (10 µg/ml) in the presence of irradiated autologous PBMC (10$^5$/well) as accessory cells. Proliferation as correlated with tritiated thymidine incorporation was determined at 72 hours. Results are expressed as mean cpm for triplicate cultures.
*Complete medium: RPMI+5% AB serum+Pen/Strep/L-glutamine+10 U/mL of IL-2.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

BIBLIOGRAPHY

Akdis & Akdis, *J Allergy Clin Immunol.* 123:735-46, 2009
Akdis & Akdis, *Nature Reviews: Drug Discovery.* 8:645-60. 2009
Akdis & Akdis, *J Allergy Clin Immunol.* 127:18-27, 2011
Alexander et al. *Clin Exp Allergy* 35: 52-8, 2004
Alexander et al. *Allergy* 60:1269-74, 2005
Allen & O'Hehir. *Clin Exp Allergy.* 41(9):1172-4, 2011
Amann et al., 1998, *Gene.,* 69:301-315
Anagnostou et al. *Clin Exp Allergy.* 41(9):1273-81, 2011
Apostolou E et al. 2006. Anaphylaxis to Gelofusine confirmed by an in vitro basophil activation test: a case series. *Anaesthesia;* 61(3):264
Asarnoj et al. *Allergy.* 2010, 65(9):1189-95
Balderi et al., 1987, *Embo J.,* 6:229-234
Blanc et al. *Clin Exp Allergy.* 2009; 39(8):1277-85
Blumchen et al. *J Allergy Clin Immunol.* 126(1):83-91, 2010
Bock et al. *J Allergy Clin Immunol.* 119(4):1016-8, 2007
Burks et al, *Int Arch Allergy Immunol* 119:165-172, 1992
Burks et al., *Allergy* 53: 725-30, 1998
Burks A W. 2008. Peanut allergy. *Lancet;*371(9623):1538
Chiang et al. *Pediatr Allergy Immunol.* 2009; 21(2 Pt 2):e429-38
Clarke et al., *Clin Exp Allergy* 28: 1251-7, 1998
Clark et al. *Allergy* 64, 1218, 2009
de Jong et al., *Clin Exp Allergy* 28: 743-51, 1998
de Leon M P et al., Suphioglu, C. 2003. Immunological analysis of allergenic cross-reactivity between peanut and tree nuts. *Clin Exp Allergy;* 33(9):1273
Drew A C et al. 2004. Hypoallergenic variants of the major latex allergen Hev b 6.01 retaining human T lymphocyte reactivity. *J Immunol:* 173(9):5872-9
Eusebius N P, Papalia L, Suphioglu C, McLellan S C, Varney M, Rolland J M, et al. Oligoclonal analysis of the atopic T cell response to the group 1 allergen of *Cynodon dactylon* (bermuda grass) pollen: pre- and post-allergen-specific immunotherapy. *Int Arch Allergy Immunol.* 2002; 127(3):234-44
Fellrath et al. *J Allergy Clin Immunol.* 111: 854-61, 2003
Glaumann et al. *Allergy.* 2012; 67(2):242-7
Hall et al. *Vaccine.* 21(5-6):549-61, 2003
Hofmann et al. *J. Allergy, Clin. Immunol.* 124, 286, 2009
Hourihane et al., *J Allergy Clin Immunol* 100: 596-600, 1997
Hoyne et al. *J Exp Med.* 178(5):1783-8, 1993
Husain Z, Schwartz R A. 2012. Peanut allergy: an increasingly common life-threatening disorder. J Am Acad Dermatol; 66(1):136
Jameel et al., 1990, *J. Virol.,* 64:3963-3966
Jones et al. *J. Allergy Clin. Immunol.* 24, 292, 2009
Kemp et al. *Med. J. Aust.* 188(9):503-4, 2008
Kleber-Janke et al., *Int Arch Allergy Immunol* 119: 265-274, 1999
Knapp et al., 1990, *Bio Techniques.,* 8:280-281
Koppelman et al. *Allergy.* 2001; 56(2):132-7
Koppelman et al. *Clin Exp Allergy.* 2004; 34(6):583-90
Kurjan and Herskowitz., 1982, *Cell.,* 30:933-943
Larch M. 2008. Of cats and men: immunodominance and the role of HLA-DP/DQ. *Clin Exp Allergy;* 38(11):1709
Lin et al. *J Microbiol Immunol Infect.* 2012
Litwin et al., *Int Arch Allergy Appl Immunol* 87: 361-61, 998
Mannering S I, Dromey J A, Morris J S, Thearle D J, Jensen K P, Harrison L C. An efficient method for cloning human autoantigen-specific T cells. *J Immunol Methods.* 2005; 298(1-2):83-92
Marazuela et al. *Mol Immunol.* 45(2):438-45, 2008
Marcotte et al., *J Allergy Clin Immunol* 101: 506-13, 1998
Mittag D, et al. 2010. The effector T cell response to ryegrass pollen is counter-regulated by simultaneous induction of regulatory T cells. *J Immunol;* 184(9); 4708
Moldaver & Larche, *Allergy* 66: 784-91, 2011
Moverare et al. *Int Arch Allergy Immunol* 2011; 156(3):282-90
Muller et al. *J Allergy Clin Immunol.* 101: 747-54, 1998
Nelson et al., *J Allergy Clin Immunol* 99: 744-51, 1997
Nopp A, et al. 2006. Basophil allergen threshold sensitivity: a useful approach to anti-IgE treatment efficacy evaluation. *Allergy;* 61(3):298
Norman et al., *Am J Respir Crit Care Med* 154: 1623-8, 1996
O'Hehir R E, et al. 2009. House dust mite sublingual immunotherapy: the role of TGF-beta and functional regulatory T cells. *Am J Respir Crit Care Med;* 180(10): 936
Oldfield et al. *Lancet* 360:47-53, 2002
Oppenheimer et al., *J Allergy Clin Immunol* 90: 256-62, 1992
Palmer et al. *Clin Immunol.* 2005; 115(3):302-12
Peeters et al. *Clin Exp Allergy.* 2007; 37(1):108-15
Pene et al., *J Allergy Clin Immunol* 102: 571-8, 1998
Pomés et al. 2006, *Clin. Exp. Allergy* 36(6):824-30
Prickett S R et al. 2011. Ara h 2 peptides containing dominant CD4+ T-cell epitopes: candidates for a peanut allergy therapeutic. *J Allergy Clin Immunol;* 127(3):608
Primeau et al., *Clin Exp Allergy* 30: 1135-43, 2000
Pumphrey, *Current Opinion in Allergy & Immunology.* 4(4): 285-90, 2004
Rolland et al. *Pharmacology & Therapeutics* 121:273-284, 2009
Rupa et al. *Allergy.* 67(1):74-82, 2012
Sambruck et al (1989)
Santambrogio et al. *Proc Natl Acad Sci USA,* 1999, 96:15056-61
Schultz et al., 1987, *Gene.,* 54:113-123
Sicherer et al., *Paediatrics* 102: e6, 1998
Tarzi et al. *Clin Exp Allergy.* 36: 465-74, 2006
Thyagarajan et al. *J Allergy Clin Immunol.* 126(1):31-2, 2010
Varney et al. 1991 *British Medical Journal* 302:265-269
Varshney et al. *J Allergy Clin Immunol.* 124(6):1351-2, 2009
Varshney et al. *J Allergy Clin Immunol.* 127(3):654-60, 2011
Worm et al. *J Allergy Clin Immunol.* 127: 89-97, 2011
Worm et al. *Expert Opin. Investig. Drugs.* 22(10): 1347-1357, 2013
Yang et al. *Clin Exp Allergy* 40(4):668-78, 2010
Yoshitomi et al. *J Pept Sci.* 13(8):499-503, 2007
Yu et al. *Int Arch Allergy Immunol.* 159(2):179-182, 2012
Zaunders J J, et al. 2009. High levels of human antigen-specific CD4+ T cells in peripheral blood revealed by stimulated coexpression of CD25 and CD134 (OX40). *J Immunol;* 183(4):2827

The invention claimed is:

1. An immunomodulatory composition comprising peptides, wherein the peptides in the composition are selected from the group consisting of:

(i) FQNLQNHRIVQIEAKPNTLV; (SEQ ID NO: 11)

(ii) STRSSENNEGVIVKVSKE; (SEQ ID NO: 12)

(iii) EVKPDKKNPQLQ; (SEQ ID NO: 4)

(iv) VEIKEGALMLPHFNSKA; (SEQ ID NO: 13)

(v) VFIMPAAHPVAINASS; (SEQ ID NO: 14)

(vi) ANLRPSEQHLM; (SEQ ID NO: 30)

(vii) EFENNQRSMSEALQ; (SEQ ID NO: 31) and (viii) RELRNLPQQSGLRA, (SEQ ID NO: 107)

wherein said composition comprises at least four peptides selected from SEQ ID NOS: 11-12, 4, and 13-14; and at least two peptides selected from SEQ ID NOS: 30-31 and 107.

2. The composition according to claim 1 wherein said composition comprises at least 7 peptides.

3. The composition according to claim 1 wherein said composition comprises each of said 8 peptides.

4. The composition according to claim 1, wherein said composition comprises peptides selected from the list consisting of:

(i) FQNLQNHRIVQIEAKPNTLV (SEQ ID NO: 11)

(ii) EVKPDKKNPQLQ (SEQ ID NO: 4)

(iii) VEIKEGALMLPHFNSKA (SEQ ID NO: 13)

(iv) VFIMPAAHPVAINASS (SEQ ID NO: 14)

(v) ANLRPSEQHLM (SEQ ID NO: 30)

(vi) EFENNQRSMSEALQ (SEQ ID NO: 31)

and (vii) RELRNLPQQSGLRA. (SEQ ID NO: 107)

5. The composition according to claim 1, wherein said peptides are capable of reducing Ara h 1 and/or Ara h 2 hypersensitivity or hypersensitivity to a composition comprising Ara h 1 and/or Ara h 2 when administered to a subject having a condition characterised by said hypersensitivity.

6. The composition according to claim 1, wherein said composition further comprises:

(i) FQNLQNHRIVQIEAKPNTLV; (SEQ ID NO: 11)

(ii) STRSSENNEGVIVKVSKE; (SEQ ID NO: 12)

(iii) VEIKEGALMLPHFNSKA; (SEQ ID NO: 13)

(iv) VFIMPAAHPVAINASS; (SEQ ID NO: 14)

(v) ANLRPXEQHLM; (SEQ ID NO: 15)

(vi) EFENNQRXMXEALQ (SEQ ID NO: 16)

wherein residue X of SEQ ID NO: 15 or 16 is cysteine or serine.

7. The composition according to claim 1, wherein said composition further comprises:

(i) FQNLQNHRIVQIEAKPNTLV; (SEQ ID NO: 11)

(ii) STRSSENNEGVIVKVSKE; (SEQ ID NO: 12)

(iii) VEIKEGALMLPHFNSKA; (SEQ ID NO: 13)

(iv) VFIMPAAHPVAINASS; (SEQ ID NO: 14)

(v) ANLRPXEQHLM; (SEQ ID NO: 15)

(vi) EFENNQRXMXEALQ; (SEQ ID NO: 16)

(vii) RELRNLPQQXGLRA (SEQ ID NO: 43)

wherein residue X of SEQ ID NO: 15, 16, or 43 is cysteine or serine.

* * * * *

SEQUENCE LISTING

<160> NUMBER OF SEQ ID NOS: 129

<210> SEQ ID NO 1
<211> LENGTH: 8
<212> TYPE: PRT
<213> ORGANISM: Arachis hypogaea

<400> SEQUENCE: 1

Phe Gln Asn Leu Gln Asn His Arg
1               5

<210> SEQ ID NO 2
<211> LENGTH: 6
<212> TYPE: PRT
<213> ORGANISM: Arachis hypogaea

<400> SEQUENCE: 2

Ile Val Gln Ile Glu Ala
1               5

<210> SEQ ID NO 3
<211> LENGTH: 10
<212> TYPE: PRT
<213> ORGANISM: Arachis hypogaea

<400> SEQUENCE: 3

Asn Glu Gly Val Ile Val Lys Val Ser Lys
1               5                   10

<210> SEQ ID NO 4
<211> LENGTH: 12
<212> TYPE: PRT
<213> ORGANISM: Arachis hypogaea

<400> SEQUENCE: 4

Glu Val Lys Pro Asp Lys Lys Asn Pro Gln Leu Gln
1               5                   10

<210> SEQ ID NO 5
<211> LENGTH: 6
<212> TYPE: PRT
<213> ORGANISM: Arachis hypogaea

<400> SEQUENCE: 5

Glu Gly Ala Leu Met Leu
1               5

<210> SEQ ID NO 6
<211> LENGTH: 7
<212> TYPE: PRT
<213> ORGANISM: Arachis hypogaea

<400> SEQUENCE: 6

Ile Met Pro Ala Ala His Pro
1               5

<210> SEQ ID NO 7
<211> LENGTH: 9
<212> TYPE: PRT
<213> ORGANISM: Arachis hypogaea
<220> FEATURE:
<221> NAME/KEY: misc_feature
<222> LOCATION: (4)..(4)
<223> OTHER INFORMATION: Xaa can be any naturally occurring amino acid

<400> SEQUENCE: 7

```
Leu Arg Pro Xaa Glu Gln His Leu Met
1               5
```

<210> SEQ ID NO 8
<211> LENGTH: 10
<212> TYPE: PRT
<213> ORGANISM: Arachis hypogaea
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 8

```
Glu Asn Asn Gln Arg Xaa Met Xaa Glu Ala
1               5                   10
```

<210> SEQ ID NO 9
<211> LENGTH: 626
<212> TYPE: PRT
<213> ORGANISM: Arachis hypogaea

<400> SEQUENCE: 9

```
Met Arg Gly Arg Val Ser Pro Leu Met Leu Leu Leu Gly Ile Leu Val
1               5                   10                  15

Leu Ala Ser Val Ser Ala Thr His Ala Lys Ser Ser Pro Tyr Gln Lys
                20                  25                  30

Lys Thr Glu Asn Pro Cys Ala Gln Arg Cys Leu Gln Ser Cys Gln Gln
            35                  40                  45

Glu Pro Asp Asp Leu Lys Gln Lys Ala Cys Glu Ser Arg Cys Thr Lys
    50                  55                  60

Leu Glu Tyr Asp Pro Arg Cys Val Tyr Asp Pro Arg Gly His Thr Gly
65                  70                  75                  80

Thr Thr Asn Gln Arg Ser Pro Pro Gly Glu Arg Thr Arg Gly Arg Gln
                85                  90                  95

Pro Gly Asp Tyr Asp Asp Asp Arg Arg Gln Pro Arg Arg Glu Glu Gly
            100                 105                 110

Gly Arg Trp Gly Pro Ala Gly Pro Arg Glu Arg Glu Arg Glu Glu Asp
        115                 120                 125

Trp Arg Gln Pro Arg Glu Asp Trp Arg Arg Pro Ser His Gln Gln Pro
    130                 135                 140

Arg Lys Ile Arg Pro Glu Gly Arg Glu Gly Glu Gln Glu Trp Gly Thr
145                 150                 155                 160

Pro Gly Ser His Val Arg Glu Glu Thr Ser Arg Asn Asn Pro Phe Tyr
                165                 170                 175

Phe Pro Ser Arg Arg Phe Ser Thr Arg Tyr Gly Asn Gln Asn Gly Arg
            180                 185                 190

Ile Arg Val Leu Gln Arg Phe Asp Gln Arg Ser Arg Gln Phe Gln Asn
        195                 200                 205

Leu Gln Asn His Arg Ile Val Gln Ile Glu Ala Lys Pro Asn Thr Leu
    210                 215                 220

Val Leu Pro Lys His Ala Asp Ala Asp Asn Ile Leu Val Ile Gln Gln
225                 230                 235                 240

Gly Gln Ala Thr Val Thr Val Ala Asn Gly Asn Asn Arg Lys Ser Phe
                245                 250                 255
```

Asn Leu Asp Glu Gly His Ala Leu Arg Ile Pro Ser Gly Phe Ile Ser
            260                 265                 270

Tyr Ile Leu Asn Arg His Asp Asn Gln Asn Leu Arg Val Ala Lys Ile
            275                 280                 285

Ser Met Pro Val Asn Thr Pro Gly Gln Phe Glu Asp Phe Pro Ala
290                 295                 300

Ser Ser Arg Asp Gln Ser Ser Tyr Leu Gln Gly Phe Ser Arg Asn Thr
305                 310                 315                 320

Leu Glu Ala Ala Phe Asn Ala Glu Phe Asn Glu Ile Arg Arg Val Leu
                325                 330                 335

Leu Glu Glu Asn Ala Gly Gly Glu Gln Glu Arg Gly Gln Arg Arg
            340                 345                 350

Trp Ser Thr Arg Ser Ser Glu Asn Asn Glu Gly Val Ile Val Lys Val
            355                 360                 365

Ser Lys Glu His Val Glu Leu Thr Lys His Ala Lys Ser Val Ser
            370                 375                 380

Lys Lys Gly Ser Glu Glu Gly Asp Ile Thr Asn Pro Ile Asn Leu
385                 390                 395                 400

Arg Glu Gly Glu Pro Asp Leu Ser Asn Asn Phe Gly Lys Leu Phe Glu
                405                 410                 415

Val Lys Pro Asp Lys Lys Asn Pro Gln Leu Gln Asp Leu Asp Met Met
                420                 425                 430

Leu Thr Cys Val Glu Ile Lys Glu Gly Ala Leu Met Leu Pro His Phe
            435                 440                 445

Asn Ser Lys Ala Met Val Ile Val Val Asn Lys Gly Thr Gly Asn
450                 455                 460

Leu Glu Leu Val Ala Val Arg Lys Glu Gln Gln Gln Arg Gly Arg Arg
465                 470                 475                 480

Glu Glu Glu Glu Asp Glu Asp Glu Glu Glu Gly Ser Asn Arg Glu
                485                 490                 495

Val Arg Arg Tyr Thr Ala Arg Leu Lys Glu Gly Asp Val Phe Ile Met
            500                 505                 510

Pro Ala Ala His Pro Val Ala Ile Asn Ala Ser Ser Glu Leu His Leu
            515                 520                 525

Leu Gly Phe Gly Ile Asn Ala Glu Asn His Arg Ile Phe Leu Ala
            530                 535                 540

Gly Asp Lys Asp Asn Val Ile Asp Gln Ile Glu Lys Gln Ala Lys Asp
545                 550                 555                 560

Leu Ala Phe Pro Gly Ser Gly Glu Gln Val Glu Lys Leu Ile Lys Asn
                565                 570                 575

Gln Lys Glu Ser His Phe Val Ser Ala Arg Pro Gln Ser Gln Ser Gln
            580                 585                 590

Ser Pro Ser Ser Pro Glu Lys Glu Ser Pro Glu Lys Glu Asp Gln Glu
            595                 600                 605

Glu Glu Asn Gln Gly Gly Lys Gly Pro Leu Leu Ser Ile Leu Lys Ala
            610                 615                 620

Phe Asn
625

<210> SEQ ID NO 10
<211> LENGTH: 157
<212> TYPE: PRT
<213> ORGANISM: Arachis hypogaea

<400> SEQUENCE: 10

```
Leu Thr Ile Leu Val Ala Leu Ala Leu Phe Leu Leu Ala Ala His Ala
1               5                   10                  15

Ser Ala Arg Gln Gln Trp Glu Leu Gln Gly Asp Arg Cys Gln Ser
            20                  25                  30

Gln Leu Glu Arg Ala Asn Leu Arg Pro Cys Glu Gln His Leu Met Gln
            35                  40                  45

Lys Ile Gln Arg Asp Glu Asp Ser Tyr Glu Arg Asp Pro Tyr Ser Pro
50                  55                  60

Ser Gln Asp Pro Tyr Ser Pro Ser Pro Tyr Asp Arg Arg Gly Ala Gly
65                  70                  75                  80

Ser Ser Gln His Gln Glu Arg Cys Cys Asn Glu Leu Asn Glu Phe Glu
                85                  90                  95

Asn Asn Gln Arg Cys Met Cys Glu Ala Leu Gln Gln Ile Met Glu Asn
            100                 105                 110

Gln Ser Asp Arg Leu Gln Gly Arg Gln Gln Glu Gln Gln Phe Lys Arg
            115                 120                 125

Glu Leu Arg Asn Leu Pro Gln Gln Cys Gly Leu Arg Ala Pro Gln Arg
            130                 135                 140

Cys Asp Leu Asp Val Glu Ser Gly Gly Arg Asp Arg Tyr
145                 150                 155

<210> SEQ ID NO 11
<211> LENGTH: 20
<212> TYPE: PRT
<213> ORGANISM: Arachis hypogaea

<400> SEQUENCE: 11

Phe Gln Asn Leu Gln Asn His Arg Ile Val Gln Ile Glu Ala Lys Pro
1               5                   10                  15

Asn Thr Leu Val
            20

<210> SEQ ID NO 12
<211> LENGTH: 18
<212> TYPE: PRT
<213> ORGANISM: Arachis hypogaea

<400> SEQUENCE: 12

Ser Thr Arg Ser Ser Glu Asn Asn Glu Gly Val Ile Val Lys Val Ser
1               5                   10                  15

Lys Glu

<210> SEQ ID NO 13
<211> LENGTH: 17
<212> TYPE: PRT
<213> ORGANISM: Arachis hypogaea

<400> SEQUENCE: 13

Val Glu Ile Lys Glu Gly Ala Leu Met Leu Pro His Phe Asn Ser Lys
1               5                   10                  15

Ala

<210> SEQ ID NO 14
<211> LENGTH: 16
<212> TYPE: PRT
<213> ORGANISM: Arachis hypogaea

<400> SEQUENCE: 14
```

```
Val Phe Ile Met Pro Ala Ala His Pro Val Ala Ile Asn Ala Ser Ser
1               5                   10                  15

<210> SEQ ID NO 15
<211> LENGTH: 11
<212> TYPE: PRT
<213> ORGANISM: Arachis hypogaea
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Ala Asn Leu Arg Pro Xaa Glu Gln His Leu Met
1               5                   10

<210> SEQ ID NO 16
<211> LENGTH: 14
<212> TYPE: PRT
<213> ORGANISM: Arachis hypogaea
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 16

Glu Phe Glu Asn Asn Gln Arg Xaa Met Xaa Glu Ala Leu Gln
1               5                   10

<210> SEQ ID NO 17
<211> LENGTH: 19
<212> TYPE: PRT
<213> ORGANISM: Arachis hypogaea

<400> SEQUENCE: 17

Asn Asn Phe Gly Lys Leu Phe Glu Val Lys Pro Asp Lys Lys Asn Pro
1               5                   10                  15

Gln Leu Gln

<210> SEQ ID NO 18
<211> LENGTH: 19
<212> TYPE: PRT
<213> ORGANISM: Arachis hypogaea

<400> SEQUENCE: 18

Gly Asp Val Phe Ile Met Pro Ala Ala His Pro Val Ala Ile Asn Ala
1               5                   10                  15

Ser Ser Glu

<210> SEQ ID NO 19
<211> LENGTH: 16
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid

<400> SEQUENCE: 19

Ser Gln Leu Glu Arg Ala Asn Leu Arg Pro Xaa Glu Gln His Leu Met
1               5                   10                  15
```

```
<210> SEQ ID NO 20
<211> LENGTH: 17
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 20

Glu Leu Asn Glu Phe Glu Asn Asn Gln Arg Xaa Met Xaa Glu Ala Leu
1               5                   10                  15

Gln

<210> SEQ ID NO 21
<211> LENGTH: 10
<212> TYPE: PRT
<213> ORGANISM: Arachis hypogaea

<400> SEQUENCE: 21

Phe Gln Asn Leu Gln Asn His Arg Ile Val
1               5                   10

<210> SEQ ID NO 22
<211> LENGTH: 13
<212> TYPE: PRT
<213> ORGANISM: Arachis hypogaea

<400> SEQUENCE: 22

Arg Ile Val Gln Ile Glu Ala Lys Pro Asn Thr Leu Val
1               5                   10

<210> SEQ ID NO 23
<211> LENGTH: 13
<212> TYPE: PRT
<213> ORGANISM: Arachis hypogaea

<400> SEQUENCE: 23

Glu Asn Asn Glu Gly Val Ile Val Lys Val Ser Lys Glu
1               5                   10

<210> SEQ ID NO 24
<211> LENGTH: 13
<212> TYPE: PRT
<213> ORGANISM: Arachis hypogaea

<400> SEQUENCE: 24

Glu Val Lys Pro Asp Lys Lys Asn Pro Gln Leu Gln Asp
1               5                   10

<210> SEQ ID NO 25
<211> LENGTH: 16
<212> TYPE: PRT
<213> ORGANISM: Arachis hypogaea
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 25
```

```
Glu Phe Glu Asn Asn Gln Arg Xaa Met Xaa Glu Ala Leu Gln Gln Ile
1               5                   10                  15
```

<210> SEQ ID NO 26
<211> LENGTH: 20
<212> TYPE: PRT
<213> ORGANISM: Arachis hypogaea

<400> SEQUENCE: 26

```
Asn Asn Phe Gly Lys Leu Phe Glu Val Lys Pro Asp Lys Lys Asn Pro
1               5                   10                  15

Gln Leu Gln Asp
            20
```

<210> SEQ ID NO 27
<211> LENGTH: 19
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 27

```
Glu Leu Asn Glu Phe Glu Asn Asn Gln Arg Xaa Met Xaa Glu Ala Leu
1               5                   10                  15

Gln Gln Ile
```

<210> SEQ ID NO 28
<211> LENGTH: 19
<212> TYPE: PRT
<213> ORGANISM: Arachis hypogaea

<400> SEQUENCE: 28

```
Trp Ser Thr Arg Ser Ser Glu Asn Asn Glu Gly Val Ile Val Val Lys
1               5                   10                  15

Ser Lys Glu
```

<210> SEQ ID NO 29
<211> LENGTH: 18
<212> TYPE: PRT
<213> ORGANISM: Arachis hypogaea

<400> SEQUENCE: 29

```
Gly Asp Val Phe Ile Met Pro Ala Ala His Pro Val Ala Ile Asn Ala
1               5                   10                  15

Ser Ser
```

<210> SEQ ID NO 30
<211> LENGTH: 11
<212> TYPE: PRT
<213> ORGANISM: Arachis hypogaea

<400> SEQUENCE: 30

```
Ala Asn Leu Arg Pro Ser Glu Gln His Leu Met
1               5                   10
```

<210> SEQ ID NO 31
<211> LENGTH: 14

```
<212> TYPE: PRT
<213> ORGANISM: Arachis hypogaea

<400> SEQUENCE: 31

Glu Phe Glu Asn Asn Gln Arg Ser Met Ser Glu Ala Leu Gln
1               5                   10

<210> SEQ ID NO 32
<211> LENGTH: 16
<212> TYPE: PRT
<213> ORGANISM: Arachis hypogaea

<400> SEQUENCE: 32

Glu Phe Glu Asn Asn Gln Arg Ser Met Ser Glu Ala Leu Gln Gln Ile
1               5                   10                  15

<210> SEQ ID NO 33
<211> LENGTH: 17
<212> TYPE: PRT
<213> ORGANISM: Arachis hypogaea

<400> SEQUENCE: 33

Ala Leu Met Leu Pro His Phe Asn Ser Lys Ala Met Val Ile Val Val
1               5                   10                  15

Val

<210> SEQ ID NO 34
<211> LENGTH: 17
<212> TYPE: PRT
<213> ORGANISM: Arachis hypogaea

<400> SEQUENCE: 34

Asn Asn Phe Gly Lys Leu Phe Glu Val Lys Pro Asp Lys Lys Asn Pro
1               5                   10                  15

Gln

<210> SEQ ID NO 35
<211> LENGTH: 13
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid

<400> SEQUENCE: 35

Ser Gln Leu Glu Arg Ala Asn Leu Arg Pro Xaa Glu Gln
1               5                   10

<210> SEQ ID NO 36
<211> LENGTH: 12
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid

<400> SEQUENCE: 36

Glu Leu Asn Glu Phe Glu Asn Asn Gln Arg Xaa Met
1               5                   10

<210> SEQ ID NO 37
<211> LENGTH: 19
<212> TYPE: PRT
```

<213> ORGANISM: Arachis hypogaea

<400> SEQUENCE: 37

Glu Leu Asn Glu Phe Glu Asn Asn Gln Arg Ser Met Ser Glu Ala Leu
1               5                   10                  15

Gln Gln Ile

<210> SEQ ID NO 38
<211> LENGTH: 18
<212> TYPE: PRT
<213> ORGANISM: Arachis hypogaea

<400> SEQUENCE: 38

Asn Asn Phe Gly Lys Leu Phe Glu Val Lys Pro Asp Lys Lys Asn Pro
1               5                   10                  15

Gln Leu

<210> SEQ ID NO 39
<211> LENGTH: 14
<212> TYPE: PRT
<213> ORGANISM: Arachis hypogaea
<220> FEATURE:
<221> NAME/KEY: misc_feature
<222> LOCATION: (11)..(11)
<223> OTHER INFORMATION: Xaa can be any naturally occurring amino acid

<400> SEQUENCE: 39

Ser Gln Leu Glu Arg Ala Asn Leu Arg Pro Xaa Glu Gln His
1               5                   10

<210> SEQ ID NO 40
<211> LENGTH: 21
<212> TYPE: PRT
<213> ORGANISM: Arachis hypogaea

<400> SEQUENCE: 40

Lys Ala Met Val Ile Val Val Val Asn Lys Gly Thr Gly Asn Leu Glu
1               5                   10                  15

Leu Val Ala Val Asp
            20

<210> SEQ ID NO 41
<211> LENGTH: 14
<212> TYPE: PRT
<213> ORGANISM: Arachis hypogaea
<220> FEATURE:
<221> NAME/KEY: misc_feature
<222> LOCATION: (10)..(10)
<223> OTHER INFORMATION: Xaa can be any naturally occurring amino acid

<400> SEQUENCE: 41

Arg Glu Leu Arg Asn Leu Pro Gln Gln Xaa Gly Leu Arg Ala
1               5                   10

<210> SEQ ID NO 42
<211> LENGTH: 11
<212> TYPE: PRT
<213> ORGANISM: Arachis hypogaea

<400> SEQUENCE: 42

Lys Ala Met Val Ile Val Val Val Asn Lys Gly
1               5                   10

<210> SEQ ID NO 43

```
<211> LENGTH: 17
<212> TYPE: PRT
<213> ORGANISM: Arachis hypogaea

<400> SEQUENCE: 43

Ala Met Val Ile Val Val Asn Lys Gly Thr Gly Asn Leu Glu Leu
1               5                   10                  15

Val

<210> SEQ ID NO 44
<211> LENGTH: 16
<212> TYPE: PRT
<213> ORGANISM: Arachis hypogaea

<400> SEQUENCE: 44

Val Val Asn Lys Gly Thr Gly Asn Leu Glu Leu Val Ala Val Arg Lys
1               5                   10                  15

<210> SEQ ID NO 45
<211> LENGTH: 20
<212> TYPE: PRT
<213> ORGANISM: Arachis hypogaea

<400> SEQUENCE: 45

Phe Asp Gln Arg Ser Arg Gln Phe Gln Asn Leu Gln Asn His Arg Ile
1               5                   10                  15

Val Gln Ile Glu
            20

<210> SEQ ID NO 46
<211> LENGTH: 20
<212> TYPE: PRT
<213> ORGANISM: Arachis hypogaea

<400> SEQUENCE: 46

Asn Leu Gln Asn His Arg Ile Val Gln Ile Glu Ala Lys Pro Asn Thr
1               5                   10                  15

Leu Val Leu Pro
            20

<210> SEQ ID NO 47
<211> LENGTH: 20
<212> TYPE: PRT
<213> ORGANISM: Arachis hypogaea

<400> SEQUENCE: 47

Arg Trp Ser Thr Arg Ser Ser Glu Asn Asn Glu Gly Val Ile Val Lys
1               5                   10                  15

Val Ser Lys Glu
            20

<210> SEQ ID NO 48
<211> LENGTH: 20
<212> TYPE: PRT
<213> ORGANISM: Arachis hypogaea

<400> SEQUENCE: 48

Asp Leu Ser Asn Asn Phe Gly Lys Leu Phe Glu Val Lys Pro Asp Lys
1               5                   10                  15

Lys Asn Pro Gln
            20
```

-continued

```
<210> SEQ ID NO 49
<211> LENGTH: 20
<212> TYPE: PRT
<213> ORGANISM: Arachis hypogaea

<400> SEQUENCE: 49

Phe Glu Val Lys Pro Asp Lys Lys Asn Pro Gln Leu Gln Asp Leu Asp
1               5                   10                  15

Met Met Leu Thr
            20

<210> SEQ ID NO 50
<211> LENGTH: 20
<212> TYPE: PRT
<213> ORGANISM: Arachis hypogaea

<400> SEQUENCE: 50

Leu Thr Cys Val Glu Ile Lys Glu Gly Ala Leu Met Leu Pro His Phe
1               5                   10                  15

Asn Ser Lys Ala
            20

<210> SEQ ID NO 51
<211> LENGTH: 20
<212> TYPE: PRT
<213> ORGANISM: Arachis hypogaea

<400> SEQUENCE: 51

Ala Leu Met Leu Pro His Phe Asn Ser Lys Ala Met Val Ile Val Val
1               5                   10                  15

Val Asn Lys Gly
            20

<210> SEQ ID NO 52
<211> LENGTH: 21
<212> TYPE: PRT
<213> ORGANISM: Arachis hypogaea

<400> SEQUENCE: 52

Lys Ala Met Val Ile Val Val Asn Lys Gly Thr Gly Asn Leu Glu
1               5                   10                  15

Leu Val Ala Val Ala
            20

<210> SEQ ID NO 53
<211> LENGTH: 20
<212> TYPE: PRT
<213> ORGANISM: Arachis hypogaea

<400> SEQUENCE: 53

Lys Glu Gly Asp Val Phe Ile Met Pro Ala Ala His Pro Val Ala Ile
1               5                   10                  15

Asn Ala Ser Ser
            20

<210> SEQ ID NO 54
<211> LENGTH: 20
<212> TYPE: PRT
<213> ORGANISM: Arachis hypogaea

<400> SEQUENCE: 54

Arg Arg Cys Gln Ser Gln Leu Glu Arg Ala Asn Leu Arg Pro Cys Glu
1               5                   10                  15
```

Gln His Leu Met
         20

<210> SEQ ID NO 55
<211> LENGTH: 20
<212> TYPE: PRT
<213> ORGANISM: Arachis hypogaea

<400> SEQUENCE: 55

Ala Asn Leu Arg Pro Cys Glu Gln His Leu Met Gln Lys Ile Gln Arg
1               5                   10                  15

Asp Glu Asp Ser
         20

<210> SEQ ID NO 56
<211> LENGTH: 20
<212> TYPE: PRT
<213> ORGANISM: Arachis hypogaea

<400> SEQUENCE: 56

Glu Leu Asn Glu Phe Glu Asn Asn Gln Arg Cys Met Cys Glu Ala Leu
1               5                   10                  15

Gln Gln Ile Met
         20

<210> SEQ ID NO 57
<211> LENGTH: 20
<212> TYPE: PRT
<213> ORGANISM: Arachis hypogaea

<400> SEQUENCE: 57

Lys Arg Glu Leu Arg Asn Leu Pro Gln Gln Cys Gly Leu Arg Ala Pro
1               5                   10                  15

Gln Arg Cys Asp
         20

<210> SEQ ID NO 58
<211> LENGTH: 10
<212> TYPE: PRT
<213> ORGANISM: Arachis hypogaea

<400> SEQUENCE: 58

Arg Ile Val Gln Ile Glu Ala Lys Pro Asn
1               5                   10

<210> SEQ ID NO 59
<211> LENGTH: 19
<212> TYPE: PRT
<213> ORGANISM: Arachis hypogaea

<400> SEQUENCE: 59

Trp Ser Thr Arg Ser Ser Glu Asn Asn Glu Gly Val Ile Val Lys Val
1               5                   10                  15

Ser Lys Glu

<210> SEQ ID NO 60
<211> LENGTH: 14
<212> TYPE: PRT
<213> ORGANISM: Arachis hypogaea

<400> SEQUENCE: 60

Glu Asn Asn Glu Gly Val Ile Val Lys Val Ser Lys Glu Ala

```
<210> SEQ ID NO 61
<211> LENGTH: 10
<212> TYPE: PRT
<213> ORGANISM: Arachis hypogaea

<400> SEQUENCE: 61

Asn Asn Phe Gly Lys Leu Phe Glu Val Lys
1               5                   10

<210> SEQ ID NO 62
<211> LENGTH: 8
<212> TYPE: PRT
<213> ORGANISM: Arachis hypogaea

<400> SEQUENCE: 62

Phe Gly Lys Leu Phe Glu Val Lys
1               5

<210> SEQ ID NO 63
<211> LENGTH: 10
<212> TYPE: PRT
<213> ORGANISM: Arachis hypogaea

<400> SEQUENCE: 63

Val Glu Ile Lys Glu Gly Ala Leu Met Leu
1               5                   10

<210> SEQ ID NO 64
<211> LENGTH: 14
<212> TYPE: PRT
<213> ORGANISM: Arachis hypogaea

<400> SEQUENCE: 64

Val Glu Ile Lys Glu Gly Ala Leu Met Leu Pro His Phe Asn
1               5                   10

<210> SEQ ID NO 65
<211> LENGTH: 13
<212> TYPE: PRT
<213> ORGANISM: Arachis hypogaea

<400> SEQUENCE: 65

Glu Gly Ala Leu Met Leu Pro His Phe Asn Ser Lys Ala
1               5                   10

<210> SEQ ID NO 66
<211> LENGTH: 15
<212> TYPE: PRT
<213> ORGANISM: Arachis hypogaea

<400> SEQUENCE: 66

Leu Met Leu Pro His Phe Asn Ser Lys Ala Met Val Ile Val Val
1               5                   10                  15

<210> SEQ ID NO 67
<211> LENGTH: 11
<212> TYPE: PRT
<213> ORGANISM: Arachis hypogaea

<400> SEQUENCE: 67

Pro His Phe Asn Ser Lys Ala Met Val Ile Val
1               5                   10
```

```
<210> SEQ ID NO 68
<211> LENGTH: 9
<212> TYPE: PRT
<213> ORGANISM: Arachis hypogaea

<400> SEQUENCE: 68

Lys Ala Met Val Ile Val Val Val Asn
1               5

<210> SEQ ID NO 69
<211> LENGTH: 10
<212> TYPE: PRT
<213> ORGANISM: Arachis hypogaea

<400> SEQUENCE: 69

Ala Met Val Ile Val Val Val Asn Lys Gly
1               5                   10

<210> SEQ ID NO 70
<211> LENGTH: 7
<212> TYPE: PRT
<213> ORGANISM: Arachis hypogaea

<400> SEQUENCE: 70

Ile Val Val Val Asn Lys Gly
1               5

<210> SEQ ID NO 71
<211> LENGTH: 16
<212> TYPE: PRT
<213> ORGANISM: Arachis hypogaea

<400> SEQUENCE: 71

Ala Met Val Ile Val Val Asn Lys Gly Thr Gly Asn Leu Glu Leu
1               5                   10                  15

<210> SEQ ID NO 72
<211> LENGTH: 13
<212> TYPE: PRT
<213> ORGANISM: Arachis hypogaea

<400> SEQUENCE: 72

Val Val Asn Lys Gly Thr Gly Asn Leu Glu Leu Val Ala
1               5                   10

<210> SEQ ID NO 73
<211> LENGTH: 14
<212> TYPE: PRT
<213> ORGANISM: Arachis hypogaea

<400> SEQUENCE: 73

Val Val Asn Lys Gly Thr Gly Asn Leu Glu Leu Val Ala Val
1               5                   10

<210> SEQ ID NO 74
<211> LENGTH: 19
<212> TYPE: PRT
<213> ORGANISM: Arachis hypogaea

<400> SEQUENCE: 74

Ala Met Val Ile Val Val Val Asn Lys Gly Thr Gly Asn Leu Glu Leu
1               5                   10                  15

Val Ala Val
```

<210> SEQ ID NO 75
<211> LENGTH: 12
<212> TYPE: PRT
<213> ORGANISM: Arachis hypogaea

<400> SEQUENCE: 75

Phe Ile Met Pro Ala Ala His Pro Val Ala Ile Asn
1               5                   10

<210> SEQ ID NO 76
<211> LENGTH: 11
<212> TYPE: PRT
<213> ORGANISM: Arachis hypogaea

<400> SEQUENCE: 76

Ile Met Pro Ala Ala His Pro Val Ala Ile Asn
1               5                   10

<210> SEQ ID NO 77
<211> LENGTH: 13
<212> TYPE: PRT
<213> ORGANISM: Arachis hypogaea

<400> SEQUENCE: 77

Ser Gln Leu Glu Arg Ala Asn Leu Arg Pro Cys Glu Gln
1               5                   10

<210> SEQ ID NO 78
<211> LENGTH: 11
<212> TYPE: PRT
<213> ORGANISM: Arachis hypogaea

<400> SEQUENCE: 78

Ser Gln Leu Glu Arg Ala Asn Leu Arg Pro Cys
1               5                   10

<210> SEQ ID NO 79
<211> LENGTH: 9
<212> TYPE: PRT
<213> ORGANISM: Arachis hypogaea

<400> SEQUENCE: 79

Leu Glu Arg Ala Asn Leu Arg Pro Cys
1               5

<210> SEQ ID NO 80
<211> LENGTH: 11
<212> TYPE: PRT
<213> ORGANISM: Arachis hypogaea

<400> SEQUENCE: 80

Leu Glu Arg Ala Asn Leu Arg Pro Cys Glu Gln
1               5                   10

<210> SEQ ID NO 81
<211> LENGTH: 10
<212> TYPE: PRT
<213> ORGANISM: Arachis hypogaea

<400> SEQUENCE: 81

Glu Arg Ala Asn Leu Arg Pro Cys Glu Gln
1               5                   10

<210> SEQ ID NO 82

```
<211> LENGTH: 11
<212> TYPE: PRT
<213> ORGANISM: Arachis hypogaea

<400> SEQUENCE: 82

Ala Asn Leu Arg Pro Cys Glu Gln His Leu Met
1               5                   10

<210> SEQ ID NO 83
<211> LENGTH: 9
<212> TYPE: PRT
<213> ORGANISM: Arachis hypogaea

<400> SEQUENCE: 83

Leu Arg Pro Cys Glu Gln His Leu Met
1               5

<210> SEQ ID NO 84
<211> LENGTH: 12
<212> TYPE: PRT
<213> ORGANISM: Arachis hypogaea

<400> SEQUENCE: 84

Glu Leu Asn Glu Phe Glu Asn Asn Gln Arg Cys Met
1               5                   10

<210> SEQ ID NO 85
<211> LENGTH: 11
<212> TYPE: PRT
<213> ORGANISM: Arachis hypogaea

<400> SEQUENCE: 85

Leu Asn Glu Phe Glu Asn Asn Gln Arg Cys Met
1               5                   10

<210> SEQ ID NO 86
<211> LENGTH: 14
<212> TYPE: PRT
<213> ORGANISM: Arachis hypogaea

<400> SEQUENCE: 86

Glu Phe Glu Asn Asn Gln Arg Cys Met Cys Glu Ala Leu Gln
1               5                   10

<210> SEQ ID NO 87
<211> LENGTH: 10
<212> TYPE: PRT
<213> ORGANISM: Arachis hypogaea

<400> SEQUENCE: 87

Glu Asn Asn Gln Arg Cys Met Cys Glu Ala
1               5                   10

<210> SEQ ID NO 88
<211> LENGTH: 11
<212> TYPE: PRT
<213> ORGANISM: Arachis hypogaea

<400> SEQUENCE: 88

Asn Asn Gln Arg Cys Met Cys Glu Ala Leu Gln
1               5                   10

<210> SEQ ID NO 89
<211> LENGTH: 12
<212> TYPE: PRT
```

<213> ORGANISM: Arachis hypogaea

<400> SEQUENCE: 89

Arg Glu Leu Arg Asn Leu Pro Gln Gln Cys Gly Leu
1               5                   10

<210> SEQ ID NO 90
<211> LENGTH: 12
<212> TYPE: PRT
<213> ORGANISM: Arachis hypogaea

<400> SEQUENCE: 90

Glu Leu Arg Asn Leu Pro Gln Gln Cys Gly Leu Arg
1               5                   10

<210> SEQ ID NO 91
<211> LENGTH: 11
<212> TYPE: PRT
<213> ORGANISM: Arachis hypogaea

<400> SEQUENCE: 91

Glu Leu Arg Asn Leu Pro Gln Gln Cys Gly Leu
1               5                   10

<210> SEQ ID NO 92
<211> LENGTH: 10
<212> TYPE: PRT
<213> ORGANISM: Arachis hypogaea

<400> SEQUENCE: 92

Leu Arg Asn Leu Pro Gln Gln Cys Gly Leu
1               5                   10

<210> SEQ ID NO 93
<211> LENGTH: 9
<212> TYPE: PRT
<213> ORGANISM: Arachis hypogaea

<400> SEQUENCE: 93

Leu Arg Asn Leu Pro Gln Gln Cys Gly
1               5

<210> SEQ ID NO 94
<211> LENGTH: 14
<212> TYPE: PRT
<213> ORGANISM: Arachis hypogaea

<400> SEQUENCE: 94

Arg Glu Leu Arg Asn Leu Pro Gln Gln Cys Gly Leu Arg Ala
1               5                   10

<210> SEQ ID NO 95
<211> LENGTH: 20
<212> TYPE: PRT
<213> ORGANISM: Arachis hypogaea

<400> SEQUENCE: 95

Lys Ala Met Val Ile Val Val Asn Lys Gly Thr Gly Asn Leu Glu
1               5                   10                  15

Leu Val Ala Val
            20

<210> SEQ ID NO 96
<211> LENGTH: 9

```
<212> TYPE: PRT
<213> ORGANISM: Arachis hypogaea

<400> SEQUENCE: 96

Phe Glu Asn Asn Gln Arg Cys Met Cys
1               5

<210> SEQ ID NO 97
<211> LENGTH: 10
<212> TYPE: PRT
<213> ORGANISM: Arachis hypogaea

<400> SEQUENCE: 97

Leu Asn Glu Phe Glu Asn Asn Gln Arg Cys
1               5                   10

<210> SEQ ID NO 98
<211> LENGTH: 9
<212> TYPE: PRT
<213> ORGANISM: Arachis hypogaea

<400> SEQUENCE: 98

Leu Arg Asn Leu Pro Gln Gln Cys Gly
1               5

<210> SEQ ID NO 99
<211> LENGTH: 9
<212> TYPE: PRT
<213> ORGANISM: Arachis hypogaea

<400> SEQUENCE: 99

Leu Pro Gln Gln Cys Gly Leu Arg Ala
1               5

<210> SEQ ID NO 100
<211> LENGTH: 13
<212> TYPE: PRT
<213> ORGANISM: Arachis hypogaea

<400> SEQUENCE: 100

Ser Gln Leu Glu Arg Ala Asn Leu Arg Pro Ser Glu Gln
1               5                   10

<210> SEQ ID NO 101
<211> LENGTH: 12
<212> TYPE: PRT
<213> ORGANISM: Arachis hypogaea

<400> SEQUENCE: 101

Glu Leu Asn Glu Phe Glu Asn Asn Gln Arg Ser Met
1               5                   10

<210> SEQ ID NO 102
<211> LENGTH: 9
<212> TYPE: PRT
<213> ORGANISM: Arachis hypogaea

<400> SEQUENCE: 102

Leu Arg Pro Ser Glu Gln His Leu Met
1               5

<210> SEQ ID NO 103
<211> LENGTH: 10
<212> TYPE: PRT
<213> ORGANISM: Arachis hypogaea
```

-continued

```
<400> SEQUENCE: 103

Glu Asn Asn Gln Arg Ser Met Ser Glu Ala
1               5                   10

<210> SEQ ID NO 104
<211> LENGTH: 20
<212> TYPE: PRT
<213> ORGANISM: Arachis hypogaea

<400> SEQUENCE: 104

Ser Gln His Gln Glu Arg Cys Cys Asn Glu Leu Asn Glu Phe Glu Asn
1               5                   10                  15

Asn Gln Arg Cys
            20

<210> SEQ ID NO 105
<211> LENGTH: 16
<212> TYPE: PRT
<213> ORGANISM: Arachis hypogaea

<400> SEQUENCE: 105

Ser Gln Leu Glu Arg Ala Asn Leu Arg Pro Ser Glu Gln His Leu Met
1               5                   10                  15

<210> SEQ ID NO 106
<211> LENGTH: 17
<212> TYPE: PRT
<213> ORGANISM: Arachis hypogaea

<400> SEQUENCE: 106

Glu Leu Asn Glu Phe Glu Asn Asn Gln Arg Ser Met Ser Glu Ala Leu
1               5                   10                  15

Gln

<210> SEQ ID NO 107
<211> LENGTH: 14
<212> TYPE: PRT
<213> ORGANISM: Arachis hypogaea

<400> SEQUENCE: 107

Arg Glu Leu Arg Asn Leu Pro Gln Gln Ser Gly Leu Arg Ala
1               5                   10

<210> SEQ ID NO 108
<211> LENGTH: 13
<212> TYPE: PRT
<213> ORGANISM: Arachis hypogaea

<400> SEQUENCE: 108

Phe Glu Asn Asn Gln Arg Cys Met Cys Glu Ala Leu Gln
1               5                   10

<210> SEQ ID NO 109
<211> LENGTH: 19
<212> TYPE: PRT
<213> ORGANISM: Arachis hypogaea

<400> SEQUENCE: 109

Leu Asn Glu Phe Glu Asn Asn Gln Arg Cys Met Cys Glu Ala Leu Gln
1               5                   10                  15

Gln Ile Met
```

-continued

```
<210> SEQ ID NO 110
<211> LENGTH: 18
<212> TYPE: PRT
<213> ORGANISM: Arachis hypogaea

<400> SEQUENCE: 110

Asn Glu Phe Glu Asn Asn Gln Arg Cys Met Cys Glu Ala Leu Gln Gln
1               5                   10                  15

Ile Met

<210> SEQ ID NO 111
<211> LENGTH: 17
<212> TYPE: PRT
<213> ORGANISM: Arachis hypogaea

<400> SEQUENCE: 111

Glu Phe Glu Asn Asn Gln Arg Cys Met Cys Glu Ala Leu Gln Gln Ile
1               5                   10                  15

Met

<210> SEQ ID NO 112
<211> LENGTH: 16
<212> TYPE: PRT
<213> ORGANISM: Arachis hypogaea

<400> SEQUENCE: 112

Phe Glu Asn Asn Gln Arg Cys Met Cys Glu Ala Leu Gln Gln Ile Met
1               5                   10                  15

<210> SEQ ID NO 113
<211> LENGTH: 15
<212> TYPE: PRT
<213> ORGANISM: Arachis hypogaea

<400> SEQUENCE: 113

Glu Asn Asn Gln Arg Cys Met Cys Glu Ala Leu Gln Gln Ile Met
1               5                   10                  15

<210> SEQ ID NO 114
<211> LENGTH: 14
<212> TYPE: PRT
<213> ORGANISM: Arachis hypogaea

<400> SEQUENCE: 114

Asn Asn Gln Arg Cys Met Cys Glu Ala Leu Gln Gln Ile Met
1               5                   10

<210> SEQ ID NO 115
<211> LENGTH: 13
<212> TYPE: PRT
<213> ORGANISM: Arachis hypogaea

<400> SEQUENCE: 115

Asn Gln Arg Cys Met Cys Glu Ala Leu Gln Gln Ile Met
1               5                   10

<210> SEQ ID NO 116
<211> LENGTH: 12
<212> TYPE: PRT
<213> ORGANISM: Arachis hypogaea

<400> SEQUENCE: 116

Gln Arg Cys Met Cys Glu Ala Leu Gln Gln Ile Met
```

```
<210> SEQ ID NO 117
<211> LENGTH: 11
<212> TYPE: PRT
<213> ORGANISM: Arachis hypogaea

<400> SEQUENCE: 117

Arg Cys Met Cys Glu Ala Leu Gln Gln Ile Met
1               5                   10

<210> SEQ ID NO 118
<211> LENGTH: 10
<212> TYPE: PRT
<213> ORGANISM: Arachis hypogaea

<400> SEQUENCE: 118

Cys Met Cys Glu Ala Leu Gln Gln Ile Met
1               5                   10

<210> SEQ ID NO 119
<211> LENGTH: 9
<212> TYPE: PRT
<213> ORGANISM: Arachis hypogaea

<400> SEQUENCE: 119

Met Cys Glu Ala Leu Gln Gln Ile Met
1               5

<210> SEQ ID NO 120
<211> LENGTH: 9
<212> TYPE: PRT
<213> ORGANISM: Arachis hypogaea

<400> SEQUENCE: 120

Glu Leu Asn Glu Phe Glu Asn Asn Gln
1               5

<210> SEQ ID NO 121
<211> LENGTH: 10
<212> TYPE: PRT
<213> ORGANISM: Arachis hypogaea

<400> SEQUENCE: 121

Glu Leu Asn Glu Phe Glu Asn Asn Gln Arg
1               5                   10

<210> SEQ ID NO 122
<211> LENGTH: 11
<212> TYPE: PRT
<213> ORGANISM: Arachis hypogaea

<400> SEQUENCE: 122

Glu Leu Asn Glu Phe Glu Asn Asn Gln Arg Cys
1               5                   10

<210> SEQ ID NO 123
<211> LENGTH: 13
<212> TYPE: PRT
<213> ORGANISM: Arachis hypogaea

<400> SEQUENCE: 123

Glu Leu Asn Glu Phe Glu Asn Asn Gln Arg Cys Met Cys
1               5                   10
```

<210> SEQ ID NO 124
<211> LENGTH: 14
<212> TYPE: PRT
<213> ORGANISM: Arachis hypogaea

<400> SEQUENCE: 124

Glu Leu Asn Glu Phe Glu Asn Asn Gln Arg Cys Met Cys Glu
1               5                   10

<210> SEQ ID NO 125
<211> LENGTH: 15
<212> TYPE: PRT
<213> ORGANISM: Arachis hypogaea

<400> SEQUENCE: 125

Glu Leu Asn Glu Phe Glu Asn Asn Gln Arg Cys Met Cys Glu Ala
1               5                   10                  15

<210> SEQ ID NO 126
<211> LENGTH: 16
<212> TYPE: PRT
<213> ORGANISM: Arachis hypogaea

<400> SEQUENCE: 126

Glu Leu Asn Glu Phe Glu Asn Asn Gln Arg Cys Met Cys Glu Ala Leu
1               5                   10                  15

<210> SEQ ID NO 127
<211> LENGTH: 17
<212> TYPE: PRT
<213> ORGANISM: Arachis hypogaea

<400> SEQUENCE: 127

Glu Leu Asn Glu Phe Glu Asn Asn Gln Arg Cys Met Cys Glu Ala Leu
1               5                   10                  15

Gln

<210> SEQ ID NO 128
<211> LENGTH: 18
<212> TYPE: PRT
<213> ORGANISM: Arachis hypogaea

<400> SEQUENCE: 128

Glu Leu Asn Glu Phe Glu Asn Asn Gln Arg Cys Met Cys Glu Ala Leu
1               5                   10                  15

Gln Gln

<210> SEQ ID NO 129
<211> LENGTH: 19
<212> TYPE: PRT
<213> ORGANISM: Arachis hypogaea

<400> SEQUENCE: 129

Glu Leu Asn Glu Phe Glu Asn Asn Gln Arg Cys Met Cys Glu Ala Leu
1               5                   10                  15

Gln Gln Ile